United States Patent
Cantrell et al.

(10) Patent No.: US 6,900,353 B2
(45) Date of Patent: May 31, 2005

(54) CYCLOPENTYL SULFONAMIDE DERIVATIVES

(75) Inventors: Buddy Eugene Cantrell, Zionsville, IN (US); Winton Dennis Jones, Jr., Carmel, IN (US); Timothy Alan Shepherd, Indianapolis, IN (US); Hamideh Zarrinmayeh, Carmel, IN (US); Dennis Michael Zimmerman, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 143 days.

(21) Appl. No.: 10/380,485

(22) PCT Filed: Sep. 28, 2001

(86) PCT No.: PCT/US01/27740

§ 371 (c)(1),
(2), (4) Date: Mar. 11, 2003

(87) PCT Pub. No.: WO02/32858

PCT Pub. Date: Apr. 25, 2002

(65) Prior Publication Data

US 2004/0067984 A1 Apr. 8, 2004

Related U.S. Application Data

(60) Provisional application No. 60/294,514, filed on May 30, 2001, and provisional application No. 60/240,351, filed on Oct. 13, 2000.

(51) Int. Cl.$^7$ .......................... A61K 31/16; A61K 31/17; A61K 31/275; A61K 31/44; A61K 31/38
(52) U.S. Cl. ........................... 564/98; 546/338; 549/75; 558/389; 558/408; 558/413; 564/79; 564/82; 564/99
(58) Field of Search ........................... 546/338; 549/75; 558/389, 408, 413; 564/79, 82, 98, 99

(56) References Cited

U.S. PATENT DOCUMENTS 6,303,816 B1 * 10/2001 Arnold et al. ................ 564/82

FOREIGN PATENT DOCUMENTS

| EP | 0753506 A | 1/1997 |
|----|-----------|--------|
| WO | WO-98/33496 | 8/1998 |
| WO | WO-00/06157 | 2/2000 |
| WO | WO-01/42203 | 6/2001 |

* cited by examiner

*Primary Examiner*—Peter O'Sullivan
(74) *Attorney, Agent, or Firm*—Nelsen L. Lentz; Danica Hostettler

(57) ABSTRACT

The present invention provides compounds of formula (I): useful for potentiating glutamate receptor function in a mammal and therefore, useful for treating a wide variety of conditions, such as psychiatric and neurological disorders.

28 Claims, No Drawings

CYCLOPENTYL SULFONAMIDE DERIVATIVES

This is the national phase application, under 35 USC 371, for PCT/US01/27740 filed 28 Sep. 2001, which claims the priority of U.S. Provisional Application No. 60/240,351 filed 13 Oct. 2000 and U.S. Provisional Application No. 60/294,514 filed 30 May 2001.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44: 505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2-0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience*, September 1993, 13(9): 3904–3915 and Kathryn M. Partin, *J. Neuroscience*, Nov. 1, 1996, 16(21): 6634–6647.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron*. Vol. 11, 1069–1082, 1993.

International Patent Application Publication WO 98/33496 published Aug. 6, 1998 discloses certain sulfonamide derivatives which are useful, for example, for treating psychiatric and neurological disorders, for example cognitive disorders; neuro-degenerative disorders such as Alzheimer's disease; age-related dementias; age-induced memory impairment; movement disorders such as tardive dyskinesia, Huntington's chorea, myoclonus, and Parkinson's disease; reversal of drug-induced states (such as cocaine, amphetamines, alcohol-induced states); depression; attention deficit disorder; attention deficit hyperactivity disorder; psychosis; cognitive deficits associated with psychosis, and drug-induced psychosis.

Additional sulfonamide derivatives which potentiate glutamate receptor function, such as AMPA receptors, have also been disclosed in the following International Patent Application Publications; WO 99/43285 published Sep. 2, 1999; WO 00/06539; WO 00/06537, WO 00/06176, WO 00/06159, WO 00/06158, WO 00/06157, WO 00/06156, WO 00/06149, WO 00/06148, and WO 00/06083, all published Feb. 10, 2000, WO 00/66546, published Nov. 9, 2000, and WO 01/42203, published Jun. 14, 2001.

SUMMARY OF THE INVENTION

The present invention provides compounds of formula I:

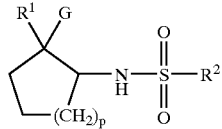

formula I wherein

G represents F or OH;

R$^1$ represents an unsubstituted or substituted aromatic group, an unsubstituted or substituted heteroaromatic group, or an unsubstituted or substituted (5–8C) cycloalkyl group;

R$^2$ represents (1–6C)alkyl, (2–6C)alkenyl, or a group of formula R$^3$R$^4$N in which R$^3$ and R$^4$ each independently represent (1–4C)alkyl; and p represents the integer 1 or 2;

or a pharmaceutically acceptable salt thereof.

The present invention further provides compounds of formula I':

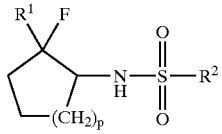

formula I' wherein

R$^1$ represents an unsubstituted or substituted aromatic group, an unsubstituted or substituted heteroaromatic group, or an unsubstituted or substituted (5–8C) cycloalkyl group;

$R^2$ represents (1–6C)alkyl, (2–6C)alkenyl, or a group of formula $R^3R^4N$ in which $R^3$ and $R^4$ each independently represent (1–4C)alkyl; and p represents the integer 1 or 2;

or a pharmaceutically acceptable salt thereof.

The present invention further provides a method of potentiating glutamate receptor function in a patient, which comprises administering to said patient an effective amount of a compound of formula I.

The present invention provides a method of treating cognitive disorders in a patient, which comprises administering to said patient an effective amount of a compound of formula I.

In addition, the present invention further provides a method of treating cognitive deficits associated with psychosis in a patient, which comprises administering to said patient an effective amount of a compound of formula I.

According to another aspect, the present invention provides the use of a compound of formula I, or a pharmaceutically acceptable salt thereof for the manufacture of a medicament for potentiating glutamate receptor function.

In addition, the present invention provides the use of a compound of formula I or a pharmaceutically acceptable salt thereof for potentiating glutamate receptor function.

The invention further provides pharmaceutical compositions comprising, a compound of formula I and a pharmaceutically acceptable diluent or carrier.

This invention also encompasses novel intermediates, and processes for the synthesis of the compounds of formula I.

DETAILED DESCRIPTION OF THE INVENTION

In this specification, the term "potentiating glutamate receptor function" refers to any increased responsiveness of glutamate receptors, for example AMPA receptors, to glutamate or an agonist, and includes but is not limited to inhibition of rapid desensitization or deactivation of AMPA receptors to glutamate.

A wide variety of conditions may be treated or prevented by compounds of formula I and their pharmaceutically acceptable salts through their action as potentiators of glutamate receptor function. Such conditions include those associated with glutamate hypofunction, such as psychiatric and neurological disorders, for example cognitive disorders and neuro-degenerative disorders such as Alzheimer's disease; age-related dementias; age-induced memory impairment; cognitive deficits due to autism, Down's syndrome and other central nervous system disorders with childhood onset, cognitive deficits post electroconvulsive therapy, movement disorders such as tardive dyskinesia, Huntington's chorea, myoclonus, dystonia, spasticity, and Parkinson's disease; reversal of drug-induced states (such as cocaine, amphetamines, alcohol-induced states); depression; attention deficit disorder; attention deficit hyperactivity disorder; psychosis; cognitive deficits associated with psychosis, drug-induced psychosis, stroke, and sexual dysfunction. Compounds of formula I may also be useful for improving memory (both short term and long term) and learning ability. The present invention provides the use of compounds of formula I for the treatment of each of these conditions.

The present invention includes the pharmaceutically acceptable salts of the compounds defined by formula I. A compound of this invention can possess a sufficiently acidic group, a sufficiently basic group, or both functional groups, and accordingly react with any of a number of organic and inorganic bases, and inorganic and organic acids, to form a pharmaceutically acceptable salt. The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. Such salts include the pharmaceutically acceptable salts listed in *Journal of Pharmaceutical Science*, 66, 2–19 (1977) which are known to the skilled artisan.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, hydrobromide, iodide, acetate, propionate, decanoate, caprate, caprylate, acrylate, ascorbate, formate, hydrochloride, dihydrochloride, isobutyrate, caproate, heptanoate, propiolate, propionate, phenylpropionate, salicylate, oxalate, malonate, succinate, suberate, sebacate, fumarate, malate, maleate, hydroxymaleate, mandelate, nicotinate, isonicotinate, cinnamate, hippurate, nitrate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydroxybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, benzenesulfonate, methanesulfonate, ethanesulfonate, propanesulfonate, hydroxyethanesulfonate, 1-naphthalenesulfonate, 2-naphthalenesulfonate, 1,5-naphthalenedisulfonate, mandelate, tartrate, and the like. Preferred pharmaceutically acceptable acid addition salts are those formed with mineral acids such as hydrochloric acid and hydrobromic acid, and those formed with organic acids such as maleic acid, oxalic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein the term "bis(pinacolato)diboron" refers to the following structure:

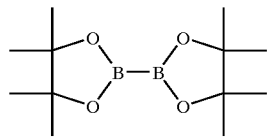

As used herein, the term "aromatic group" means the same as aryl, and includes phenyl and a polycyclic aromatic carbocyclic ring such as 1- or 2-naphthyl, 1,2-dihydronaphthyl, 1,2,3,4-tetrahydronaphthyl, and the like. Phenyl is the preferred aromatic group.

The term "heteroaromatic group" includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or another 5–6 membered ring containing one to four atoms selected from oxygen, sulfur and nitrogen. Examples of heteroaromatic groups are thienyl, furyl, oxazolyl, isoxazolyl, oxadiazoyl, pyrazolyl, thiazolyl, thiadiazolyl, isothiazolyl, imidazolyl, triazolyl, tetrazolyl, pyridyl, pyridazinyl, pyrimidyl, benzofuryl, benzothienyl, benzimidazolyl, benzoxazolyl, benzothiazolyl, indolyl, and quinolyl.

The term (5–8C)cycloalkyl includes cyclopentyl, cyclohexyl, cycloheptyl and cyclooctyl.

The term "substituted" as used in the term "substituted aromatic, heteroaromatic group, or substituted (5–8C) cycloalkyl group" herein signifies that one or more (for example one or two) substituents may be present, said substituents being selected from atoms and groups which, when present in the compound of formula I, do not prevent the compound of formula I from functioning as a potentiator of glutamate receptor function.

It is understood that when $R^1$ represents an unsubstituted or substituted (5–8C)cycloalkyl group, mixtures of cis and trans isomers may result which can be separated into the individual cis and trans isomers by one of ordinary skill in the art, using standard techniques and procedures such as reverse phase or normal phase high performance liquid chromatography or flash chromatography, with a suitable stationary phase and a suitable eluent. Examples of suitable stationary phases are silica gel, alumina, and the like. Examples of suitable eluents are ethyl acetate/hexane, ethyl acetate/toluene, methanol/dichloromethane, and the like. Such individual cis and trans isomers are included within the scope of the present invention.

Examples of substituents which may be present on a substituted aromatic group, a substituted heteroaromatic group, or a substituted (5–8)C cycloalkyl group include halogen; nitro; cyano; (1–10C) alkyl; (2–10C)alkenyl; (2–10C)alkynyl; (3–8C)cycloalkyl; hydroxy(3–8C) cycloalkyl; oxo(3–8C)cycloalkyl; halo(1–10C)alkyl; —O—(CH$_2$)$_t$CN, —O—(CH$_2$)$_t$NH$_2$, —O—(CH$_2$)$_t$NHCOR$^{10a}$, —O—(CH$_2$)$_t$NHSO$_2$R$^{10a}$ in which t is an integer of from 1 to 4; (CH$_2$)$_y$X$^1$R$^9$ in which y is 0 or an integer of from 1 to 4, X$^1$ represents O, S, NR$^{10}$, CO, COO, OCO, CONR$^{11}$, NR$^{12}$CO, NR$^{12}$COCOO, OCONR$^{13}$, R$^9$ represents hydrogen, (1–10C) alkyl, (3–10C)alkenyl, (3–10C)alkynyl, pyrrolidinyl, tetrahydrofuryl, morpholino or (3–8C)

cycloalkyl and $R^{10}$, $R^{10a}$, $R^{11}$, $R^{12}$ and $R^{12}$ each independently represent hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C)alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyl dihydrothiazolyl; (1–4C) alkoxycarbonyl dimethyl-dihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$, or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen; nitro; cyano; (1–10C) alkyl; (2–10C)alkenyl; (2–10C)alkynyl; (3–8C)cycloalkyl; 4-(1,1-dioxotetrahydro-1,2-thiazinyl); halo (1–10C)alkyl; cyano(2–10C)alkenyl; phenyl; and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $SO_2NH$, $NHSO_2NR^{17}$, $OCONR^{19}$ or $NR^{19}COO$, $R^{15}$ represents hydrogen, (1–10C)alkyl, phenyl (1–4C)alkyl, halo(1–10C)alkyl, (1–4C)alkoxycarbonyl (1–4C)alkyl, (1–4C)alkylsulfonylamino(1–4C)alkyl, N-(1–4C)alkoxycarbonyl)(1–4C)alkylsulfonylamino(1–4C)alkyl, (3–10C)alkenyl, (3–10C)alkynyl, (3–8C)cycloalkyl, camphoryl, or an aromatic or heteroaromatic group which is unsubstituted or substituted by one or two of halogen, (1–4C)alkyl, halo(1–4C)alkyl, di(1–4C)alkylamino and (1–4C)alkoxy, and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group.

The term (1–10C)alkyl refers to a straight or branched alkyl chain having from one to ten carbon atoms and includes (1–6C)alkyl and (1–4C)alkyl. Particular values are methyl, ethyl, propyl, isopropyl, butyl, isobutyl, t-butyl, pentyl, and hexyl.

The terms "halogen", "Hal" or "halide" include fluorine, chlorine, bromine and iodine unless otherwise specified.

The term (1–6C)alkoxy, refers to a straight or branched alkyl chain having from one to six carbon atoms attached to an oxygen atom and includes (1–4C)alkoxy, such as methoxy, ethoxy, propoxy, isopropoxy, isobutoxy, tert-butoxy, pentoxy, and the like.

The term (2–10C)alkenyl includes (3–10C)alkenyl, (2–8C)alkenyl, (2–6C)alkenyl and (2–4C)alkenyl. Particular values are vinyl and prop-2-enyl.

The term (2–10C)alkynyl includes (3–10C)alkynyl, (2–8C)alkynyl, (2–6C)alkynyl and (3–4C)alkynyl. A particular value is prop-2-ynyl.

The term halo(1–10C)alkyl includes fluoro(1–10C)alkyl, such as trifluoromethyl and 2,2,2-trifluoroethyl, and chloro(1–10C)alkyl such as chloromethyl.

The term (2–4C)alkylene includes ethylene, propylene and butylene. A preferred value is ethylene.

The term —(1–4C)alkyl(3–8C)cycloalkyl includes the following:

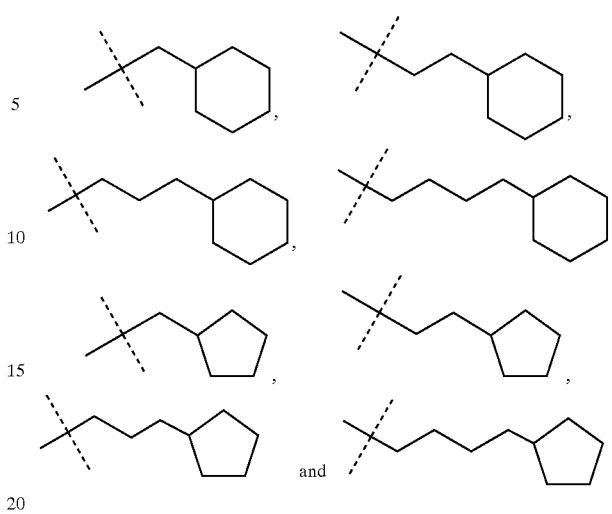

The term —(1–4C)alkylaromatic includes the following:

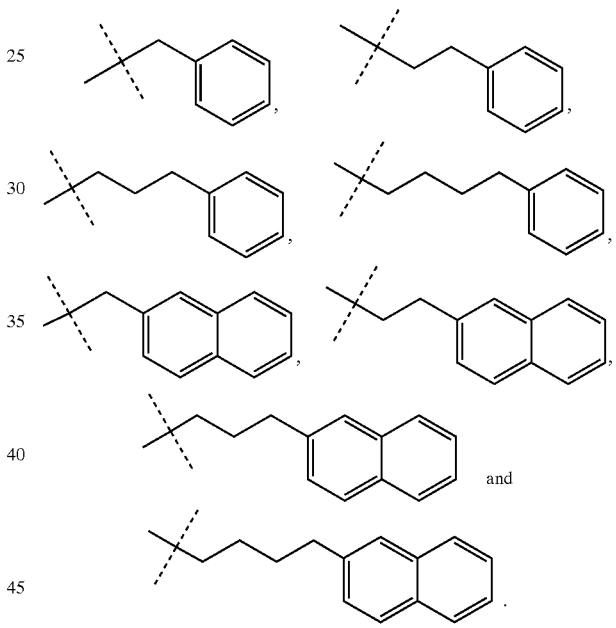

Examples of values for $R^9$ are hydrogen, methyl, ethyl, propyl, isopropyl, t-butyl, ethenyl, cyclopropyl, cyclobutyl, cyclopentyl, cyclohexyl, 2-pyrrolidinyl, morpholino or 2-tetrahydrofuryl.

$R^9$ is preferably (1–4C)alkyl, (2–4C)alkenyl, (3–6C)cycloalkyl, pyrrolidinyl, morpholino or tetrahydrofuryl.

$R^{10a}$ is preferably methyl, ethyl, propyl, 2-propyl and butyl, with methyl and 2-propyl being preferred.

Examples of values for $R^{15}$ are hydrogen, methyl, ethyl, propyl, isopropyl, butyl, t-butyl, benzyl, 2,2,2-trifluoroethyl, 2-methoxycarbonylethyl, cyclohexyl, 10-camphoryl, phenyl, 2-fluorophenyl, 3-fluorophenyl, 2-trifluoromethylphenyl, 4-trifluoromethylphenyl, 2-methoxyphenyl, 3-methoxyphenyl, 4-methoxyphenyl, 1-(5-dimethylamino)naphthyl, and 2-thienyl.

$X^1$ preferably represents O, CO, CONH or NHCO.

z is preferably 0.

Particular values for the groups $(CH_2)_yX^1R^9$ and $(CH_2)_zX^3R^{15}$ include (1–10C)alkoxy, including (1–6C)alkoxy and (1–4C)alkoxy, such as methoxy, ethoxy, propoxy, isopropoxy and isobutoxy; (3–10C)alkenyloxy, including (3–6C) alkenyloxy, such as prop-2-enyloxy; (3–10C)alkynyloxy, including (3–6C)alkynyloxy, such as prop-2-ynyloxy; and (1–6C)alkanoyl, such as formyl and ethanoyl.

Examples of particular values for y are 0 and 1.

Examples of particular values for z are 0, 1, 2 and 3.

Examples of particular values for t are 1 and 2, with 2 being preferred.

$L^a$ and $L^b$ preferably each independently represents $CH_2$.

$X^2$ preferably represents a bond, O, NH, CO, CH(OH), CONH, NHCONH or $OCH_2CONH$, with a bond, O, and CONH being especially preferred.

Preferably the group $(CH_2)_y X^1 R^9$ represents CHO; $COCH_3$, $OCH_3$; $OCH(CH_3)_2$; $NHCOR^9$ in which $R^9$ represents methyl, ethyl, isopropyl, t-butyl, ethenyl, cyclopropyl, cyclobutyl, cyclopentyl, cyclohexyl, 2-pyrolidinyl or morpholino; $CONHR^9$ in which $R^9$ represents cyclopropyl or cyclopentyl; $NHCOCOOCH3$; or 2-tetrahydrofurylmethoxy.

Preferably the group $(CH_2)_z X^3 R^{15}$ represents $NH_2$; $CH_2NH_2$; $(CH_2)_2NH_2$; $(CH_2)_3NH_2$; $CONH_2$; $CONHCH_3$; $CON(CH_3)_2$; $N(C_2H_5)_2$; $CH_2OH$; $CH(OH)CH_3$; $CH(OH)CH_2CH_2$; CHO; $COCH_3$; COOH; $COOCH_3$; $CH_2NHCOOC(CH_3)_3$; $(CH_2)_2NHCOOC(CH_3)_3$; $SO_2NH_2$; $NHSO_2CH_3$; $NHSO_2CH(CH_3)_2$; a group of formula $(CH_2)_2NHSO_2R^{15}$ in which $R^{15}$ represents $CH_3$, $CH_2CH_3$, $CH(CH_3)_2$, $(CH_2)_2CH_3$, $(CH_3)_3CH_3$, benzyl, $CH_2CF_3$, 2-methoxycarbonylethyl, cyclohexyl, 10-camphoryl, phenyl, 2-fluorophenyl, 4-fluorophenyl, 2-trifluoromethylphenyl, 4-trifluoromethylphenyl, 4-methoxyphenyl, 1-(2-dimethylamino)naphthyl or 2-thienyl; $CH(OH)CH_2NHSO_2CH_3$; $(CH_2)_3NHSO_2CH(CH_3)_2$; $COCH_2N(OCOC(CH_3)_2SO_2CH_3$; $COCH_2NHSO_2CH_3$; $(CH_2)_2NHCOR^{15}$ in which $R^{15}$ represents $CH_3$, $CH(CH_3)_2$, $CH_2CH(CH_3)_2$, phenyl, 3-fluorophenyl, 4-fluorophenyl, benzyl, 2-methoxyphenyl, 4-methoxyphenyl, 2-thienyl, CH=CH, CH=CHCN, $OCH_3$ or $O(CH_2)_3CH_3$.

Examples of particular values for $(L^a)_n—X^2—(L^b)_m$ are a bond, O, NH, S, SO, $SO_2$, CO, $CH_2$, $COCH_2$, COCONH, $CH(OH)CH_2$, CONH, NHCO, NHCONH, $CH_2O$, $OCH_2$, $OCH_2CONH$, $CH_2NH$, $NHCH_2$ and $CH_2CH_2$, with a bond, CONH, and $CH_2O$ being especially preferred.

$R^{14}$ is preferably an unsubstituted or substituted phenyl, naphthyl, furyl, thienyl, isoxazolyl, thiazolyl, tetrazolyl, pyridyl, pyrimidyl benzothienyl or benzothiazolyl group with unsubstituted or substituted phenyl being preferred.

Examples of particular values for $R^{14}$ are phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 2,3-difluoro-phenyl, 2,4-difluorophenyl, 3,5-difluorophenyl, 3,4-dichlorophenyl, 3,5-dichlorophenyl, 4-cyanophenyl, 3-nitrophenyl, 4-hydroxyiminophenyl, 2-methylphenyl, 4-methylphenyl, 4-ethylphenyl, 3-propylphenyl, 4-t-butylphenyl, 2-prop-2-enylphenyl, 4-(4-(1,1-dioxotetrahydro-1,2-thiazinyl)phenyl, 2-trifluoromethylphenyl, 3-trifluoromethylphenyl, 4-trifluoromethylphenyl, 2-bromomethylphenyl, 2-fluoro-4-trifluoromethylphenyl, 4-(2-cyanoethenyl)phenyl, 4-phenyl, 2-formylphenyl, 3-formylphenyl, 4-formylphenyl, 2-acetylphenyl, 3-acetylphenyl, 4-acetylphenyl, 2-propanoylphenyl, 2-(2-methyl-propanoyl)phenyl, 2-methoxyphenyl, 3-methoxyphenyl, 4-methoxyphenyl, 4-butoxyphenyl, 2-hydroxymethylphenyl, 4-hydroxymethylphenyl, 2-(1-hydroxyethyl)phenyl, 3-(1-hydroxyethyl)phenyl, 4-(1-hydroxyethyl)phenyl, 2-(1-hydroxypropyl)phenyl, 4-(1-hydroxypropyl)phenyl, 2-(1-hydroxy-2,2-dimethyl-propyl)phenyl, 4-trifluoromethoxyphenyl, 2-aminophenyl,4-aminophenyl, 4-N,N-diethylaminophenyl, 4-aminomethylphenyl, 4-(2-aminoethyl)phenyl, 4-(3-aminopropyl)phenyl, 4-carboxyphenyl, 4-carbamoylphenyl, 4-N-methylcarbamoylphenyl, 4-N,N-dimethylcarbamoylphenyl, 2-isopropylaminomethylphenyl, 4-t-butoxycarbonylaminomethylphenyl, 4-(2-isopropoxy-carboxamido)ethylphenyl, 4-(2-t-butoxycarboxamido)ethyl-phenyl, 4-isopropylsulfonylaminophenyl, 4-(2-methane-sulfonylamino)ethylphenyl, 4-(2-ethylsulfonylamino)ethyl-phenyl, 4-(3-isopropylsulfonylamino)propylphenyl, 4-(1-(2-(2-propane)sulfonylamino)propyl)phenyl, 4-(2-propylsulfonylamino)ethylphenyl, 4-(2-isopropylsulfonylamino)ethylphenyl, 4-(2-butylsulfonylamino)ethylphenyl, 4-(1-isopropyl-sulfonylaminomethyl)ethylphenyl, 4-(1-hydroxy-2-methane-sulfonylamino)ethylphenyl, 4-(2-(2,2,2-trifluoroethyl)sulfonylaminoethyl)phenyl, 4-(2-cyclohexylsulfonylamino)-ethylphenyl, 4-(2-(2,2,2-trifluoroethyl)sulfonylamino)-ethylphenyl, 4-(2-N,N-dimethylaminosulfonylamino)-ethylphenyl, 4-(2-phenylsulfonylaminoethyl)phenyl, 4-(2-(2-fluorophenyl)sulfonylaminoethyl)phenyl, 4-(2-(4-fluorophenyl)sulfonylaminoethyl)phenyl, 4-(2-(2-trifluoromethylphenyl)sulfonylaminoethyl)phenyl, 4-(2-(4-trifluoromethylphenyl)sulfonylaminoethyl)phenyl, 4-(2-(4-methoxyphenyl)sulfonylaminoethyl)phenyl, 4-(2-(1-(5-dimethylamino)naphthalenesulfonylamino)ethyl)phenyl, 4-(2-(2-thienyl)sulfonylamino)ethyl)phenyl, 4-(2-benzamidoethyl)-phenyl, 4-(2-(4-fluorobenzamido)ethyl)phenyl, 4-(2-(3-methoxybenzamido)ethyl)phenyl, 4-(2-(3-fluorobenzamido)-ethyl)phenyl, 4-(2-(4-methoxybenzamido)ethyl)phenyl, 4-(2-(2-methoxybenzamido)ethyl)phenyl, 4-(1-(2-(2-methoxycarbonylethanesulfonylamino)ethyl)phenyl, 4-(1-(2-(10-camphorsulfonylamino)ethyl)phenyl, 4-(1-(2-(benzylsulfonyl-amino)ethyl)phenyl, 4-(2-phenylacetamido)ethyl)phenyl, 4-methanesulfonylaminoethanoylphenyl, 4-(N-(t-butoxy-carbonyl)methanesulfonylaminoethanoyl)phenyl, 4-(2-(2-thienylcarboxamido)ethyl)phenyl, thien-2-yl, 5-hydroxy-methylthien-2-yl, 5-formylthien-2-yl, thien-3-yl, 5-hydroxymethylthien-3-yl, 5-formylthien-3-yl, 2-bromothien-3-yl, fur-2-yl, 5-nitrofur-2-yl, fur-3-yl, isoxazol-5-yl, 3-bromoisoxazol-5-yl, isoxazol-3-yl, 5-trimethylsilylisoxazol-3-yl, 5-methylisoxazol-3-yl, 5-hydroxymethylisoxazol-3-yl, 5-methyl-3-phenylisoxazol-4-yl, 5-(2-hydroxyethyl)isoxazol-3-yl, 5-acetylisoxazol-3-yl, 5-carboxyisoxazol-3-yl, 5-N-methylcarbamoylisoxazol-3-yl, 5-methoxycarbonylisoxazol-3-yl, 3-bromo[1,2,4] oxadiazol-5-yl, pyrazol-1-yl, thiazol-2-yl, 4-hydroxymethylthiazol-2-yl, 4-methoxycarbonylthiazol-2-yl, 4-carboxythiazol-2-yl, imidazol-1-yl, 2-sulfhydrylimidazol-1-yl, [1,2,4]triazol-1-yl, tetrazol-5-yl, 2-methyltetrazol-5-yl, 2-ethyltetrazol-5-yl, 2-isopropyl-tetrazol-5-yl, 2-(2-propenyl)tetrazol-5-yl, 2-benzyl-tetrazol-5-yl, pyrid-2-yl, 5-ethoxycarbonylpyrid-2-yl, pyrid-3-yl, 6-chloropyrid-3-yl, pyrid-4-yl, 5-trifluoro-methylpyrid-2-yl, 6-chloropyridazin-3-yl, 6-methylpyridazin-3-yl, 6-methoxypyrazin-3-yl, pyrimidin-5-yl, benzothien-2-yl, benzothiazol-2-yl, and quinol-2-yl.

Examples of an unsubstituted or substituted aromatic or heteroaromatic group represented by $R^1$ are unsubstituted or substituted phenyl, furyl, thienyl (such as 3-thienyl) and pyridyl (such as 3-pyridyl).

More preferably, R¹ represents 2-naphthyl or a group of formula

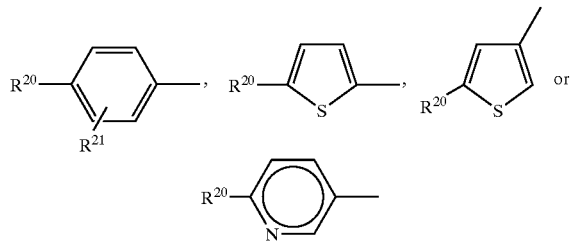

in which

R²⁰ represents halogen; nitro; cyano; (1–10C) alkyl; (2–10C)alkenyl; (2–10C)alkynyl; (3–8C)cycloalkyl; hydroxy(3–8C)cycloalkyl; oxo(3–8C)cycloalkyl; halo (1–10C)alkyl; —O—(CH₂)ₜCN, —O—(CH₂)ₜNH₂, —O—(CH₂)ₜNHCOR¹⁰ᵃ, —O—(CH₂)ₜNHSO₂R¹⁰ᵃ in which t is an integer of from 1 to 4; (CH₂)ᵧX¹R⁹ in which y is 0 or an integer of from 1 to 4, X¹ represents O, S, NR¹⁰, CO, COO, OCO, CONR¹¹, NR¹²CO, NR¹²COCOO, OCONR¹³, R⁹ represents hydrogen, (1–10C) alkyl, (3–10C)alkenyl, (3–10C)alkynyl, pyrrolidinyl, tetrahydrofuryl, morpholino or (3–8C)cycloalkyl and R¹⁰, R¹⁰ᵃ, R¹¹, R¹² and R¹³ each independently represents hydrogen or (1–10C)alkyl, or R⁹ and R¹⁰, R¹¹, R¹² or R¹³ together with the nitrogen atom to which they are attached form an azetidinyl, pyrrolidinyl, piperidinyl or morpholino group; N-(1–4C)alkylpiperazinyl; N-phenyl(1–4C)alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyl dihydrothiazolyl; (1–4C)alkoxycarbonyl dimethyl-dihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula R¹⁴—(Lᵃ)ₙ—X²—(Lᵇ)ₘ in which X² represents a bond, O, NH, S, SO, SO₂, CO, CH(OH), CONH, NHCO, NHCONH, NHCOO, COCONH, OCH₂CONH, or CH=CH, Lᵃ and Lᵇ each represent (1–4C) alkylene, one of n and m is 0 or 1 and the other is 0, and R¹⁴ represents a phenyl or heteroaromatic group which is unsubstituted or substituted by one or two of halogen; nitro; cyano; (1–10C) alkyl; (2–10C)alkenyl; (2–10C)alkynyl; (3–8C) cycloalkyl; 4-(1,1-dioxotetrahydro-1,2-thiazinyl); halo (1–10C)alkyl; cyano(2–10C)alkenyl; phenyl; and (CH₂)ᵤX³R¹⁵ in which z is 0 or an integer of from 1 to 4, X³ represents O, S, NR¹⁶, CO, CH(OH), COO, OCO, CONR¹⁷, NR¹⁸CO, NHSO₂, SO₂NH, NHSO₂NR¹⁷, OCONR¹⁹ or NR¹⁹COO, R¹⁵ represents hydrogen, (1–10C)alkyl, phenyl (1–4C)alkyl, halo(1–10C)alkyl, (1–4C)alkoxycarbonyl (1–4C)alkyl, (1–4C)alkylsulfonylamino(1–4C)alkyl, N-(1–4C)alkoxycarbonyl)(1–4C)alkylsulfonylamino(1–4C) alkyl, (3–10C)alkenyl, (3–10C)alkynyl, (3–8C)cycloalkyl, camphoryl, or an aromatic or heteroaromatic group which is unsubstituted or substituted by one or two of halogen, (1–4C)alkyl, halo(1–4C)alkyl, di(1–4C)alkylamino and (1–4C)alkoxy, and R¹⁶, R¹⁷, R¹⁸ and R¹⁹ each independently represents hydrogen or (1–10C)alkyl, or R¹⁵ and R¹⁶, R¹⁷, R¹⁸ or R¹⁹ together with the nitrogen atom to which they are attached form an azetidinyl, pyrrolidinyl, piperidinyl or morpholino group; and R²¹ represents a hydrogen atom, a halogen atom, a (1–4C)alkyl group or a (1–4C)alkoxy group.

Examples of particular values for R²⁰ are fluorine, chlorine, bromine, cyano, hydroxyimino, methyl, ethyl, propyl, 2-propyl, butyl, 2-methylpropyl, 1,1-dimethylethyl, cyclopentyl, cyclohexyl, 3-hydroxycyclopentyl, 3-oxocyclopentyl, methoxy, ethoxy, propoxy, 2-propoxy, acetyl, acetylamino, ethylcarboxamido, propylcarboxamido, 1-butanoylamino, t-butylcarboxamido, acryloylamido, 2-pyrrolidinylcarboxamido, 2-tetrahydrofurylmethoxy, morpholinocarboxamido, methyloxalylamido, cyclopropylcarboxamido, cyclobutylcarboxamido, cyclopentylcarboxamido, cyclohexylcarboxamido, cyclopropylcarbamoyl, cyclopentylcarbamoyl, pyrrolidin-1-yl, morpholino, piperidin-1-yl, N-methylpiperazinyl, N-benzylpiperazinyl, 2-thienyl, 3-thienyl, 2-furyl, 3-furyl, isoxazol-3-yl, thiazol-2-yl, tetrazol-5-yl, pyrid-2-yl, pyrid-3-yl, pyrid-4-yl, pyrimidin-5-yl, 4,5-dihydrothiazol-2-yl, 4,5-dihydro-4-methoxycarbonylthiazol-2-yl, 4,5-dihydro-4-methoxy-carbonyl-5,5-dimethylthiazol-2-yl, benzothien-2-yl, benzothiazol-2-yl, phenyl, 2-fluorophenyl, 3-fluorophenyl, 2,3-difluorophenyl, 4-chlorophenyl, 3,4-dichlorophenyl, 3,5-dichlorophenyl, 3-nitrophenyl, 4-cyanophenyl, 2-methylphenyl, 4-methylphenyl, 4-(4-(1,1-dioxotetrahydro-1,2-thiazinyl)phenyl, 3-trifluoromethylphenyl, 4-trifluoro-methylphenyl, 4-(2-cyanoethenyl)phenyl, 2-formylphenyl, 3-formylphenyl, 4-formylphenyl, 3-acetylphenyl, 4-acetylphenyl, 4-carboxyphenyl, 2-methoxyphenyl, 4-methoxyphenyl, 2-hydroxymethylphenyl, 4-hydroxymethylphenyl, 3-(1-hydroxyethyl)phenyl, 4-(1-hydroxyethyl)phenyl, 4-(1-hydroxypropyl)phenyl, 2-aminophenyl, 4-aminophenyl, 4-N,N-diethylaminophenyl, 4-aminomethylphenyl, 4-(2-aminoethyl)-phenyl, 4-(3-aminopropyl)phenyl, 4-(2-acetylaminoethyl)-phenyl, 4-t-butoxycarboxylaminoethyl) phenyl, 4-(2-t-butoxycarboxylaminoethyl)phenyl, benzylsulfonylamino, 4-isopropylsulfonylaminophenyl, 4-(2-methanesulfonylaminoethyl)phenyl, 4-(2-ethylsulfonylaminoethyl)phenyl, 4-(2-propylsulfonylaminoethyl)phenyl, 4-(2-butylsulfonylaminoethyl)phenyl, 4-(2-isopropylsulfonylaminoethyl) phenyl, 4-(1-hydroxy-2-methanesulfonylaminoethyl) phenyl, 4-(2-dimethylaminosulfonylaminoethyl)phenyl, 4-(1-(2-(2-propyl)sulfonylaminopropyl)phenyl, 4-(2-(2,2,2-trifluoroethyl)sulfonylaminoethyl)phenyl, 4-(2-cyclohexylsulfonyl-aminoethyl)phenyl, 4-(2-phenylsulfonylaminoethyl)phenyl, 4-(2-(2-fluorophenyl) sulfonylaminoethyl)phenyl, 4-(2-(4-fluorophenyl) sulfonylaminoethyl)phenyl, 4-(2-(2-trifluoromethylphenyl) sulfonylaminoethyl)phenyl, 4-(2-(4-trifluoromethylphenyl) sulfonylaminoethyl)phenyl, 4-(2-(4-methoxyphenyl) sulfonylaminoethyl)phenyl, 4-(2-(1-(5-dimethylamino) naphthalenesulfonylamino)ethyl)phenyl, 4-(2-(2-thienyl) sulfonylamino)ethyl)phenyl, 4-(2-benzamidoethyl)-phenyl, 4-(2-(4-fluorobenzamido)ethyl)phenyl, 4-(2-(3-methoxybenzamido)ethyl)phenyl, 4-(2-(3-fluorobenzamido)-ethyl)phenyl, 4-(2-(4-methoxybenzamido)ethyl)phenyl, 4-(2-(2-methoxybenzamido)ethyl)phenyl, 4-(2-(2-thienylcarboxamido)ethyl)phenyl, 4-carbamoylphenyl, 4-methylcarbamoylphenyl, 4-dimethylcarbamoylphenyl, 4-(2-(2-methylpropaneamido)ethyl)phenyl, 4-(2-(3-methylbutaneamido)ethyl)phenyl, benzoylmethyl, benzamido, 2-fluorobenzamido, 3-flurobenzamido, 4-fluorobenzamido, 2,4-difluorobenzamido, 3-chlorobenzamido, 4-chlorobenzamido, 4-bromobenzamido, 4-iodobenzamido, 4-cyanobenzamido, 3-methylbenzamido, 4-methylbenzamido, 4-ethylbenzamido, 4-propylbenzamido, 4-t-butylbenzamido, 4-vinylbenzamido, 2-trifluoromethylbenzamido, 3-trifluoromethylbenzamido, 4-trifluoromethylbenzamido, 2-fluoro-4-trifluoromethylbenzamido, 2-methoxybenzamido, 3-methoxybenzamido, 4-methoxybenzamido, 4-butoxybenzamido, 4-phenylphenyl-carboxamido, 4-benzylcarboxamido, 4-phenoxymethyl-carboxamido, 2-fluorobenzylamino, benzyloxy, 2-fluorobenzyloxy, 2-hydroxy-2-phenylethyl, 2-fluorophenylcarbamoyl, 4-(1-(2-(2-methoxycarbonylethanesulfonylamino)ethyl)phenyl, 4-(1-(2-(10-camphorsulfonylamino)ethyl)phenyl, 4-(1-(2-(benzylsulfonylamino)ethyl)phenyl, 4-(2-phenylacetamido)-ethyl)phenyl, 4-(methanesulfonylaminoethanoyl)phenyl, 4-(N-t-butoxycarbonyl)methanesulfonylaminoethanoyl)phenyl, 2-thienylcarboxamido, 2-furylcarboxamido, 3-(5-methyl-isoxazolyl)carboxamido, 5-isoxazolylcarboxamido, 2-benzothienylcarboxamido, 4-(5-methyl-3-phenylisoxazolyl)-carboxamido, 4-pyridylcarboxamido, 2-(5-nitrofuryl)-carboxamido, 2-pyridylcarboxamido, 6-chloro-2-pyridyl-carboxamido, 2-thienylsulfonamido, 2-thienylmethylamino, 3-thienylmethylamino, 2-furylmethylamino, 3-furylmethylamino, 3-acetylureido and 2-(2-thienyl)ethylureido.

Examples of particular values for $R^{21}$ are hydrogen and chlorine with hydrogen being preferred. $R^{21}$ is preferably ortho to $R^{20}$.

Examples of particular values for $R^1$ are 2-naphthyl, 4-bromophenyl, 4-cyanophenyl, 4-benzamidophenyl, 4-methylphenyl, 4-isopropyl-phenyl, 4-isobutylphenyl, 4-t-butylphenyl, 4-methoxyphenyl, 4-isopropoxyphenyl, 4-cyclopentylphenyl, 4-cyclohexylphenyl, 4-(2-hydroxymethylphenyl)phenyl, 4-(4-hydroxymethylphenyl)-phenyl, 4-(2-furyl)phenyl, 4-(3-furyl)phenyl, 4-(2-thienyl)phenyl, 4-(3-thienyl)phenyl, 4-(pyrrolidin-1-yl)phenyl, 4-(piperidin-1-yl)phenyl, 3-chloro-4-piperidin-1-ylphenyl, 4-benzyloxyphenyl, 4-(2-fluorophenyl)phenyl, 4-(3-fluorophenyl)phenyl, 4-(2-formylphenyl)phenyl, 4-(3-formylphenyl)-phenyl, 4-(4-formylphenyl)phenyl, 4-(4-methylphenyl)phenyl, and 4-(2-methoxyphenyl)phenyl. Additional examples of particular values for $R^1$ are shown in table 1 below.

TABLE 1

A 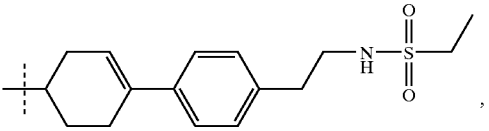

B 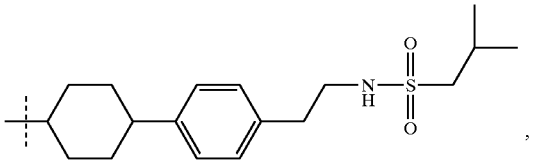

C 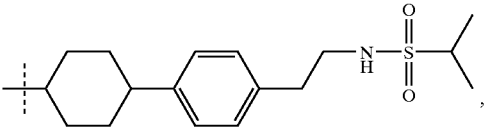

TABLE 1-continued

D 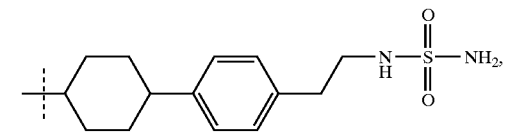

E 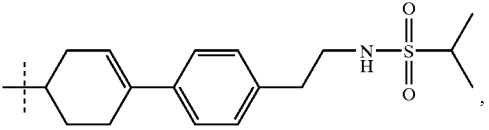

F 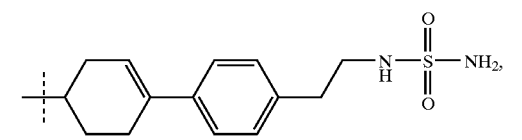

G 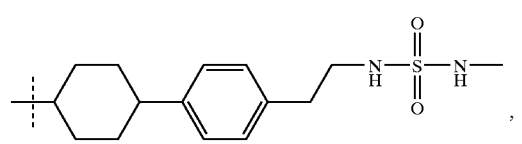

H 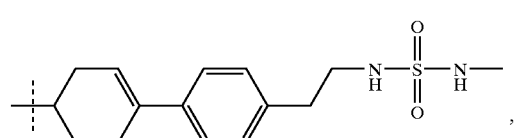

I 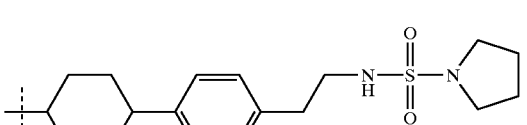

J 

K 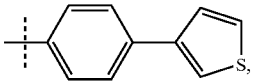

L 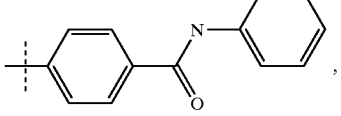

M 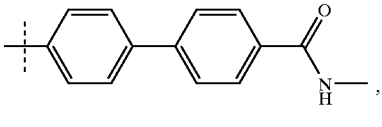

N 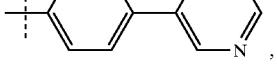

O 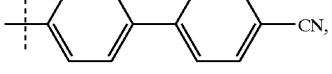

TABLE 1-continued

| Label | Structure |
|---|---|
| P | 4-hydroxy-4-(thiophen-2-yl)cyclohexyl |
| Q | 4-(2,4-difluorobenzamido)phenyl |
| R | 4'-(2-methanesulfonamidoethyl)biphenyl-4-yl |
| T | 4-(isonicotinamido)phenyl |
| U | 4-(6-chloronicotinamido)phenyl |
| V | trans-4-hydroxy-4-(thiophen-3-yl)cyclohexyl |
| W | 4-iodophenyl |
| X | biphenyl-4-yl |
| Y | 4'-carboxybiphenyl-4-yl |
| Z | 4-(3,5-difluorobenzamido)phenyl |
| Aa | 4'-sulfamoylbiphenyl-4-yl |
| Ab | 3'-(methanesulfonamido)biphenyl-4-yl |
| Ac | 3'-aminobiphenyl-4-yl |
| Ad | 3'-(methanesulfonamido)biphenyl-4-yl |
| Ae | 4-((3,5-difluorobenzyl)oxy)phenyl |
| Af | 4-(benzyloxy)phenyl |
| Ag | 4-((4-cyanobenzyl)oxy)phenyl |
| Ah | 4-((2-cyanobenzyl)oxy)phenyl |
| Ai | 4-phenoxyphenyl |
| Aj | 4-methoxyphenyl |
| Ak | 4-hydroxyphenyl |
| Al | 4-fluorophenyl |

TABLE 1-continued

| Am | 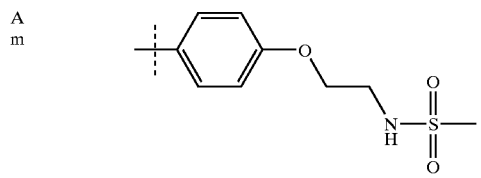 |

TABLE 1-continued

| Ap | 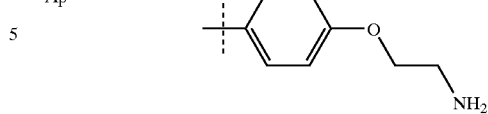 |

The compounds of formula I can be prepared by one of ordinary skill in the art, for example, following the procedures set forth below in Schemes I–VII. The reagents and starting materials are readily available to one of ordinary skill in the art. All substituents, unless otherwise specified are as previously defined.

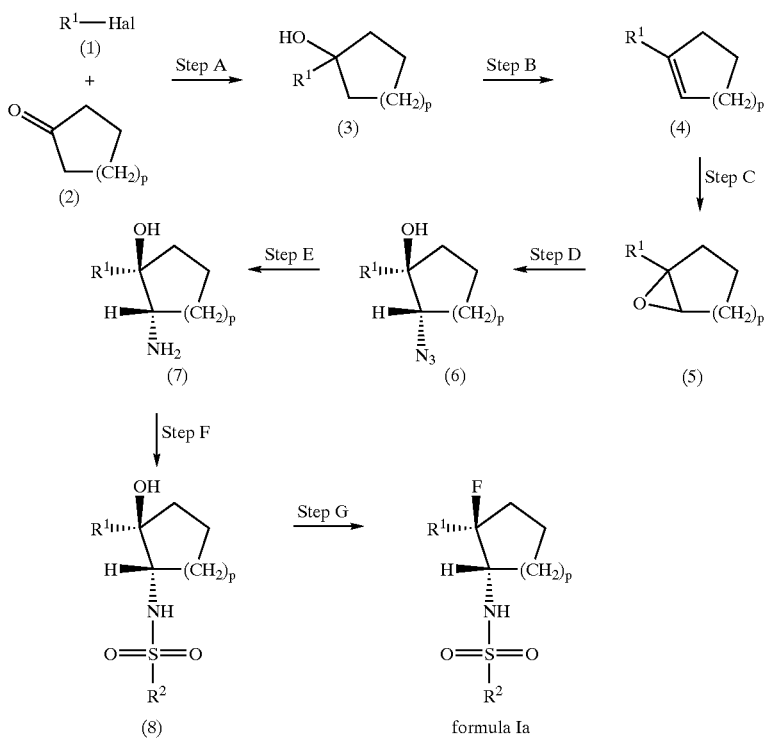

TABLE 1-continued

| An | 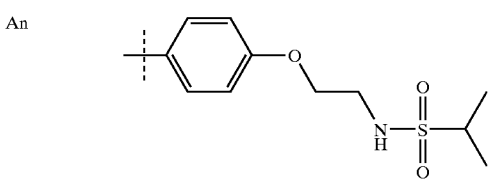 |
| Ao | 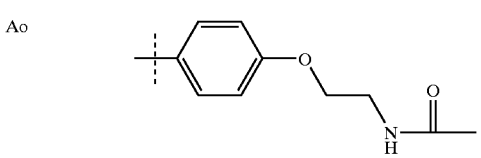 |

In Scheme I, step A, the compound of structure (1) is combined with the ketone of structure (2) under standard Grignard conditions well known in the art to provide the alcohol (3), for example see Jerry March, "*Advanced Organic Chemistry: Reaction, Mechanisms, and Structure*," Fourth Edition, John Wiley & Sons, (1992) pages 920–929. More specifically, for example, magnesium turnings are added to a suitable organic solvent, such as anhydrous THF under an atmosphere of nitrogen. A small amount of compound (1) is added along with an iodine crystal and a catalytic amount of dibromoethane. The reaction is heated with vigorous stirring to initiate the Grignard formation. A total of about 1.1 equivalents of compound (1) is added dropwise to the reaction. The reaction is then allowed to cool to room temperature and about 1.06 equivalents of ketone (2) is added dropwise to the reaction. The reaction mixture is then heated at reflux for about 2 hours and allowed to cool to room temperature overnight. The alcohol (3) is then isolated using standard techniques. For example, saturated ammonium chloride is added to precipitate the salts. The organic layer is decanted off and the remaining salts are rinsed with ether which is combined with the first organic layer. The combined organics are concentrated under vacuum and the residue is taken up in a suitable organic solvent, such as ethyl acetate, dried over potassium carbonate, filtered, and concentrated under vacuum to provide crude alcohol (3). The crude material can then be purified using standard techniques, such as chromatography on silica gel with a suitable eluent, such as hexane/ethyl acetate to provide purified alcohol (3).

In Scheme I, step B the alcohol (3) is dehydrated under standard conditions to provide the compound (4). For example, the alcohol (3) is dissolved in a suitable organic solvent, such as toluene and treated with p-toluenesulfonic acid. The reaction mixture is heated at reflux for about 4 hours and water is removed using a Dean-Stark trap. The reaction mixture is then allowed to cool to room temperature and concentrated under vacuum. The crude residue is taken up in a suitable organic solvent, such as methylene chloride, washed with water, dried over potassium carbonate, filtered, and concentrated under vacuum. The crude product (4) can be purified by chromatography on silica gel with a suitable eluent, such as hexane/methylene chloride.

In Scheme I, step C the compound (4) is epoxidized under conditions well known in the art to provide the epoxide (5). For example, about 3 equivalents m-chloroperbenzoic acid is added portionwise to about 5 equivalents of sodium fluoride in a suitable organic solvent, such as methylene chloride. The reaction mixture is allowed to stir for about 30 minutes at room temperature and compound (4) is added to the mixture in one portion. The reaction mixture is then allowed to stir for about 2 to 4 hours at room temperature, and then is filtered. The filtrate is washed with 1 N sodium hydroxide, water, dried over potassium carbonate, filtered, and concentrated under vacuum to provide the crude epoxide (5). This crude material can be purified using silica gel chromatography with a suitable eluent, such as hexane/methylene chloride to provide the purified epoxide (5).

In Scheme I, step D, the epoxide (5) is opened under standard conditions to provide the azide (6). For example, 1.08 equivalents of epoxide (5) dissolved in a suitable organic solvent, such as DMF, is added dropwise at room temperature to a mixture of sodium azide in water. The reaction is heated at 90° C. with stirring for about 8 to 12 hours. The mixture is then poured into water and extracted with a suitable organic solvent, such as ether. The organic layer is washed with water, dried over potassium carbonate, filtered, and concentrated under vacuum to provide the azide (6).

In Scheme I, step E, the azide (6) is converted to the amine (7) under conditions well known in the art. For example, azide (6) is dissolved in a suitable organic solvent, such as toluene and added dropwise to a suitable reducing agent, such as Red-Al® (available from Aldrich Chemical Company, Milwaukee, Wis.) under a nitrogen atmosphere at room temperature. The reaction mixture is allowed to stir for 1 to 4 hours and then is poured into water. The aqueous is extracted with a suitable organic solvent, such as ethyl acetate. The organic extracts are combined, rinsed with water, dried over anhydrous potassium carbonate, filtered, and concentrated under vacuum to provide the crude amine (7). This crude material can be purified by chromatography on silica gel with a suitable eluent, such as methylene chloride/methanol to provide purified amine (7).

In Scheme I, step F, the amine (7) is converted to the sulfonamide of compound (8) under conditions well known in the art. For example, amine (7) is dissolved in a suitable organic solvent. Examples of suitable organic solvents include methylene chloride, tetrahydrofuran, and the like. The solution is treated with a slight excess of a suitable base, and then cooled to about −78° C. to about 0° C. Examples of suitable bases include triethylamine, pyridine, 1,8-diazabicyclo[5.4.0]undec-7-ene (DBU), and the like. To the stirring solution is added one equivalent of $LgSO_2R^2$. The term "Lg" as used herein refers to a suitable leaving group. Examples of suitable leaving groups include, Cl, Br, and the like. Cl is the preferred leaving group. The reaction mixture is stirred at about 0° C. to about 50° C. for about 0.5 hours to about 16 hours. The sulfonamide (8) is then isolated and purified by techniques well known in the art, such as extraction techniques and chromatography. For example, the mixture is washed with 10% sodium bisulfate, the layers separated and the aqueous extracted with several times with a suitable organic solvent, such as methylene chloride. The organic extracts are combined, dried over anhydrous sodium sulfate, filtered and concentrated under vacuum. The residue is then purified by flash chromatography on silica gel with a suitable eluent such as ethyl acetate/hexane to provide the sulfonamide (8).

In Scheme I, step G, the sulfonamide (8) is converted to compound of formula Ia under standard conditions well known in the art. For example, compound (8) is dissolved in a suitable organic solvent, such as methylene chloride and the solution is cooled to about −78° C. under an inert atmosphere, such as nitrogen. To this solution is added slowly, about one equivalent of diethylaminosulfur trifluoride (DAST) dissolved in a suitable organic solvent, such as methylene chloride with stirring. The reaction is then allowed to warm to room temperature and the compound of formula Ia is then isolated and purified using techniques and procedures well known in the art, such as extraction techniques and chromatography. For example, the reaction is diluted with water and methylene chloride. The layers are separated and the organic layer is washed with water, dried over anhydrous sodium sulfate, filtered and concentrated under vacuum to provide the crude compound of formula Ia. This crude material can then be purified by standard techniques, such as recrystallization from a suitable eluent, or flash chromatography or radial chromatography on silica gel, with a suitable eluent, such as hexane/ethyl acetate or methylene chloride to provide purified compound of formula Ia.

Scheme IA

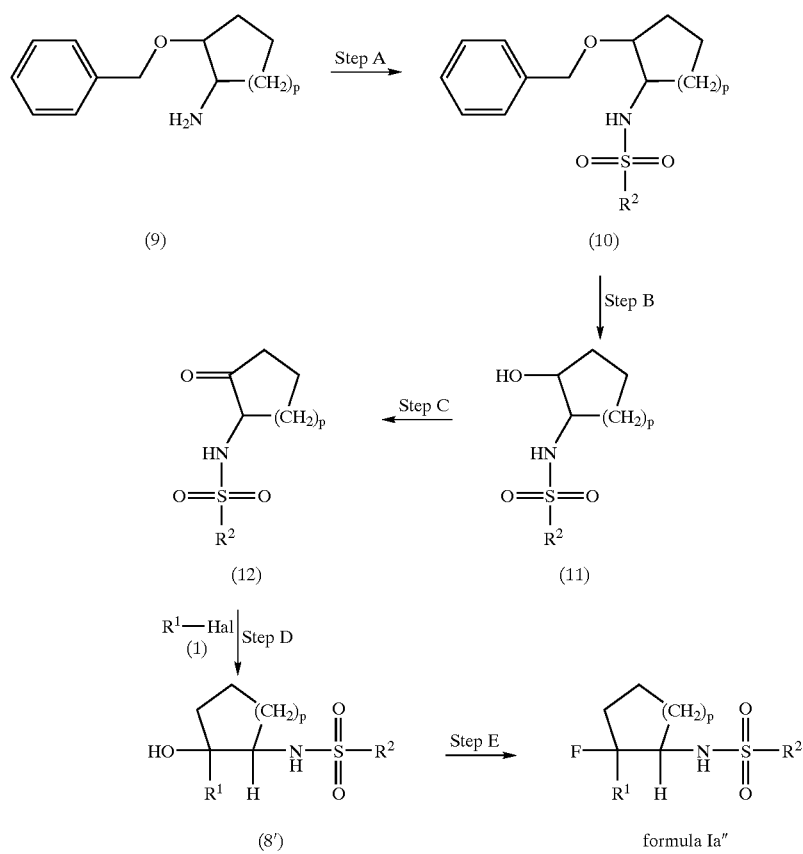

In Scheme IA, step A, the compound of structure (9) is amidated to provide the sulfonamide of structure (10) in a manner analogous to the procedure set forth in Scheme I, step F.

In Scheme IA, step B, the sulfonamide (10) is deprotected under standard conditions to provide the alcohol of structure (11). For example, the sulfonamide (10) is dissolved in a suitable organic solvent, such as ethanol, treated with a suitable hydrogenation catalyst, such as palladium on carbon and placed under a hydrogen atmosphere at about 60 psi for about 8 to 16 hours. The reaction mixture is then filtered and the filtrate is concentrated under vacuum to provide the alcohol (11).

In Scheme IA, step C, the alcohol (11) is oxidized under conditions well known in the art to provide the ketone of structure (12). For example, the alcohol (11) dissolved in a suitable organic solvent, such as methylene chloride and treated with about 1.1 to 1.5 equivalents of a suitable oxidizing reagent, such as pyridinium chlorochromate (PCC). The reaction mixture is allowed to stir for about 2 to 8 hours and is then filtered through Celte®. The filtrate is washed with water, dried over potassium carbonate, filtered, and concentrated under vacuum to provide the crude ketone (12). The ketone (12) can be purified by chromatography on silica gel with a suitable eluent, such as methylene chloride/ethyl acetate to provide the purified ketone (12).

In Scheme IA, step D, the ketone (12) is combined with the compound of structure (1) under standard Grignard conditions in a manner analogous to the procedure set forth in Scheme I, step A above to provide the alcohol of structure (8'). It is understood by one of ordinary skill in the art that a mixture of cis/trans isomers will be obtained in this reaction. These isomers can be separated using standard separation techniques well known in the art such as chromatography on silica gel with a suitable eluent, such as ethyl acetate/hexane. Alternatively, the cis/trans mixture can be carried on to step E below and the mixture can then be separated.

In Scheme IA, step E, the alcohol (8') is fluorinated in a manner analogous to the procedure set forth in Scheme I, step G above to provide the compounds of formula Ia".

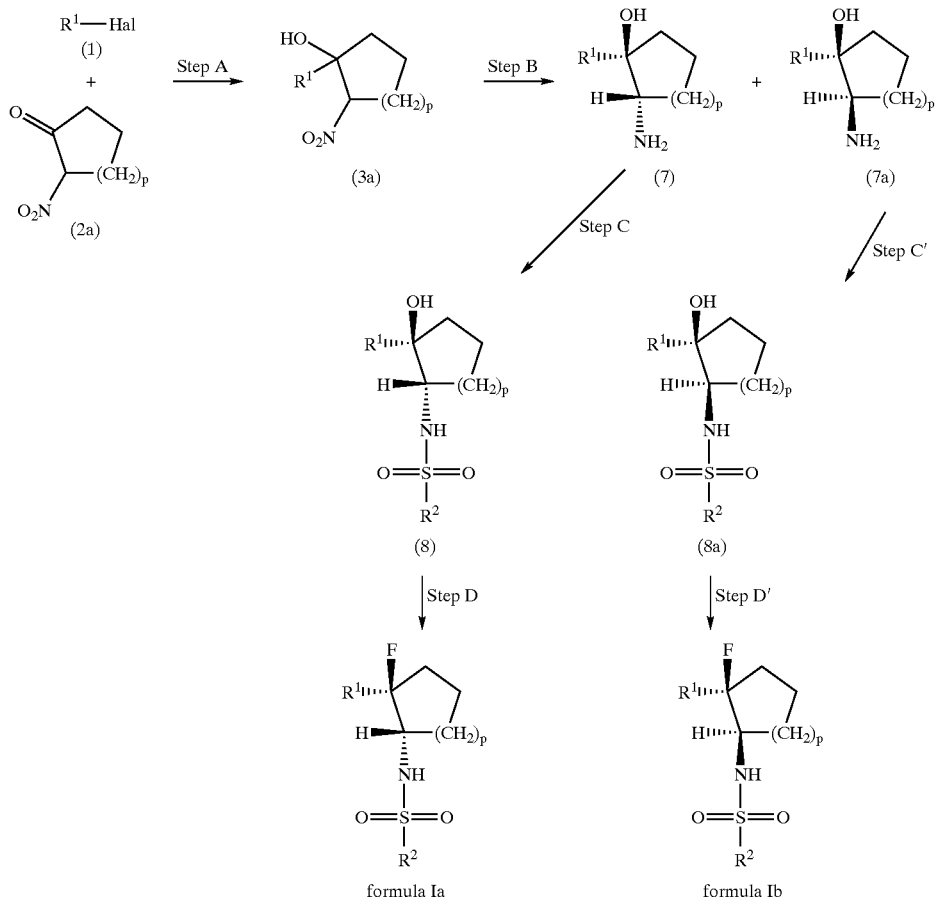

In Scheme II, step A the compound (1) is combined with compound (2a) under standard Grignard conditions well known in the art to provide the alcohol (3) as described above in Scheme I, step A.

In Scheme II, step B, the compound (2a) is reduced under conditions well known in the art to provide the amines (7) and (7a). For example, compound (2) is dissolved in a suitable organic solvent, such as ethanol, a catalytic amount of a suitable catalyst, such as palladium on carbon is added, and the reaction mixture is placed under hydrogen at about 60 psi for about 8 to 12 hours. The reaction mixture is then filtered through Celite® and the filtrate is concentrated under vacuum to provide the crude mixture of (7) and (7a). The compounds (7) and (7a) can then be separated by chromatography on silica gel with a suitable eluent, such as methanol/methylene chloride.

In Scheme II, step C, amine (7) is sulfonylated in a manner analogous to the procedure set forth in Scheme I, step F, to provide the sulfonamide (8).

In Scheme II, step C', amine (7a) is sulfonylated in a manner analogous to the procedure set forth in Scheme I, step F, to provide the sulfonamide (8a).

In Scheme II, step D, sulfonamide (8) is fluorinated in a manner analogous to the procedure set forth in Scheme I, step G to provide the compound of formula Ia.

In Scheme II, step D', sulfonamide (8a) is fluorinated in a manner analogous to the procedure set forth in Scheme I, step G to provide the compound of formula Ib.

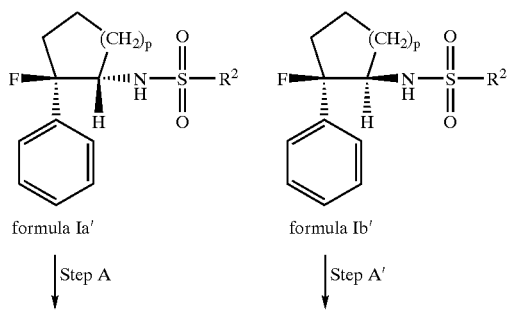

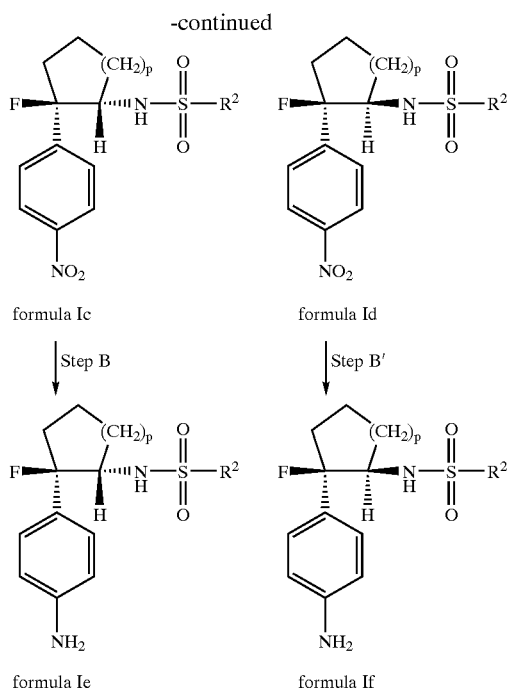

formula Ic formula Id

Step B

Step B' formula Ie formula If

In Scheme III, steps A or A', compounds of formula Ia' and Ib' are nitrated under conditions well known in the art to provide the nitro derivatives of formulas Ic and Id. For example, the compound of formula Ia' or Ib' is combined with trifluoroacetic acid in a suitable organic solvent mixture, such as methylene chloride and heptane. The mixture is cooled to about −5° C. and about 1.2 equivalents of 98% fuming nitric acid is added to the mixture. The reaction is then stirred at about −5° C. to 5° C. for about 3 to about 5 hours and then warmed to room temperature. The reaction mixture is then diluted with methylene chloride and water, and mixed for about 15 minutes. The aqueous phase is then separated and extracted with methylene chloride. The organic phase and organic extracts are combined, treated with water and aqueous base, such as 10% sodium hydroxide. The pH is adjusted to about 6.5 to about 7.5 with saturated sodium carbonate. The mixture is stirred for about 10 to 15 minutes and the organic layer is separated. The organic layer is then concentrated under vacuum to provide p-nitro derivative of formula Ic or Id which is carried on directly to step F.

In Scheme III, steps B and B', the compounds of formula Ic and I d are reduced under standard conditions to provide the amino derivatives of formulas Ie and If. For example, the crude p-nitro derivative of formula Ic or Id is dissolved in ethanol, treated with a suitable hydrogenation catalyst, such as palladium on carbon and placed under hydrogen at a pressure sufficient to effect reduction, of the p-nitro derivative to the p-amino derivative. The reaction is filtered and the filtrate is concentrated under vacuum. The residue can then be purified using standard techniques well known in the art, such as flash chromatography on silica gel with a suitable eluent, such as ethyl acetate/hexanes to provide the amino derivatives of formulas Ie or If.

Scheme IV

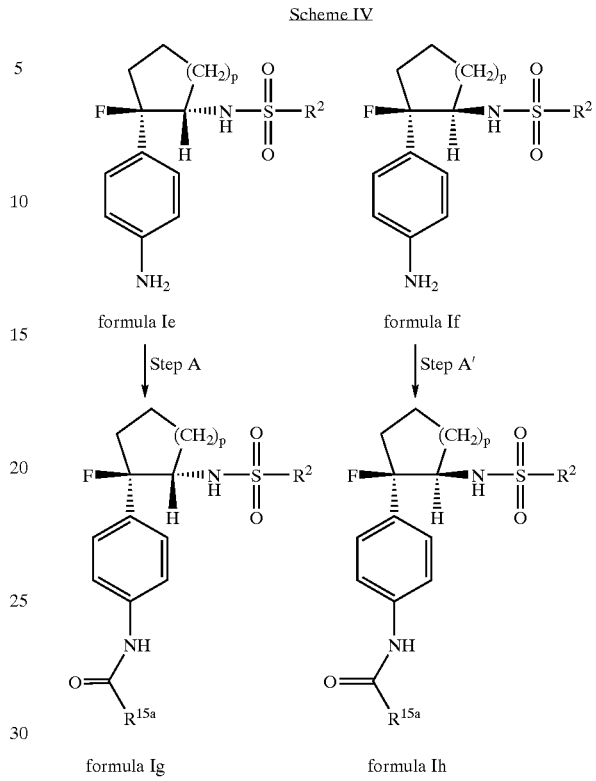

formula Ie formula If

Step A

Step A' formula Ig formula Ih

In Scheme IV, the compounds of formula Ie and If are amidated under conditions well known in the art to provide the compounds of formulas Ig and Ih wherein $R^{15a}$ represents (1–6C)alkyl, fluoro(1–4C)alkyl, or phenyl which is unsubstituted or substituted by one or two of halogen, (1–4C)alkyl, halo(1–4C) alkyl, and (1–4C)alkoxy. For example, amide formation can be carried out using standard peptide coupling procedures well known in the art, such as the azide method, the mixed carbonic acid anhydride (isobutyl chloroformate) method, or the carbodiimide (dicyclohexylcarbodiimide, diisopropylcarbodiimide, or water-soluble carbodiimide) method. Some of these methods, such as the carbodiimide method, can be enhanced by adding 1-hydroxybenzotriazole. More specifically, for example, the amine of formula Ie or If is dissolved in a suitable organic solvent, such as methylene chloride under an atmosphere of nitrogen, and treated with an excess of a suitable organic base, such as triethylamine. The solution is cooled to about 0° C. and treated with about 1.1 to about 1.5 equivalents of an acid chloride of formula $ClCOR^{15a}$. After addition is complete, the reaction mixture is allowed to warm to room temperature and stirred for about 8 to 16 hours. The reaction is then quenched with water and dried over anhydrous sodium sulfate, filtered, and concentrated under vacuum to provide the crude amide of formula Ig or Ih. This crude material can then be purified by flash chromatography on silica gel with a suitable eluent, such as ethyl acetate/hexane.

Scheme V

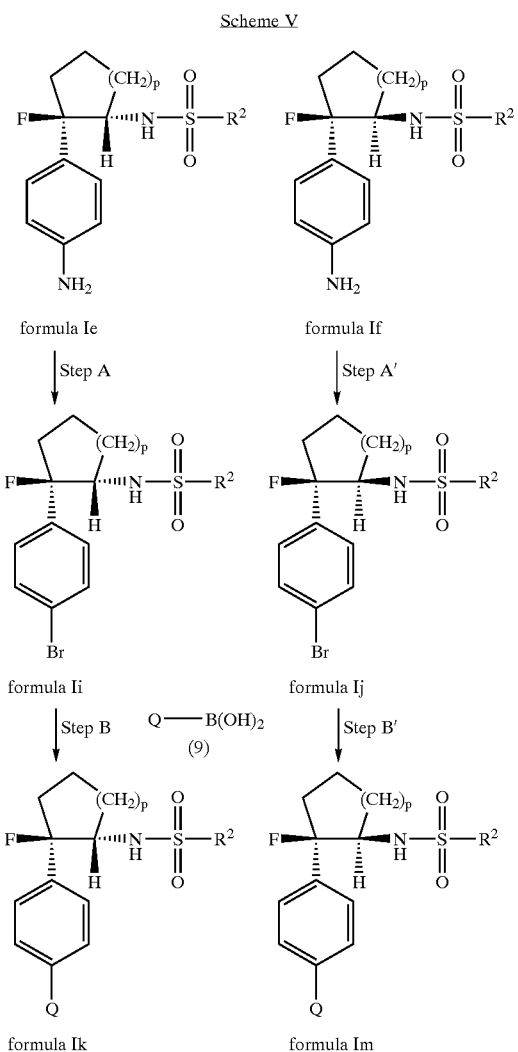

formula Ie / formula If / formula Ii / formula Ij / formula Ik / formula Im

In Scheme V, Steps A and A', the compounds of formulas Ie and If are converted to the bromide derivatives of formulas Ii and Ij under conditions well known in the art, such as those disclosed by Wu and Mosher, *J. Org. Chem.*, 51, 1904 (1986).

In Scheme V, steps B and B', the compound of formulas Ii and Ij are coupled with compound of structure (9) under standard Suzuki coupling conditions, which are well known in the art, to provide the compounds of formulas Ik and Im. See Suzuki, A., *Journal of Organometallic Chemistry*, 576, 147–168 (1999), and Miyaura and Suzuki, *Chemical Reviews*, 95, 2457–2483 (1995) for examples of Suzuki-type coupling reactions and conditions. Q in structure (9) represents a phenyl or heteroaromatic group which is unsubstituted or substituted by one or two of halogen; nitro; cyano; (1–10C)alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $SO_2NH$, $NHSO_2NR^{17}$, $OCONR^{19}$ or $NR^{19}COO$, $R^{15}$ represents hydrogen, (1–10C)alkyl, phenyl (1–4C)alkyl, halo(1–10C)alkyl, (1–4C)alkoxycarbonyl (1–4C)alkyl, (1–4C)alkylsulfonylamino(1–4C)alkyl, N-(1–4C)alkoxycarbonyl)(1–4C)alkylsulfonylamino(1–4C)alkyl, (3–10C)alkenyl, (3–10C)alkynyl, (3–8C)cycloalkyl, camphoryl, or an aromatic or heteroaromatic group which is unsubstituted or substituted by one or two of halogen, (1–4C)alkyl, halo(1–4C)alkyl, di(1–4C)alkylamino and (1–4C)alkoxy, and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group.

For example, compound of formula Ii or Ij is combined with about 1.5 equivalents of compound (9), about 1.5 equivalents of potassium carbonate, and about 0.06 equivalents of tetrakis(triphenyl phosphine)palladium(0) in a suitable solvent or solvent mixture, such as dioxane/water (3:1). The mixture is then heated at about 100° C. for about 18 hours. The reaction is then cooled and the product is isolated and purified using standard techniques and procedures, such as extraction techniques and chromatography. For example, the reaction mixture is extracted with a suitable organic solvent, such as ethyl acetate, the organic extracts are combined, washed with water, dried over anhydrous sodium sulfate, filtered, and concentrated under vacuum. The crude material is then purified by chromatography on silica gel with a suitable eluent, such as hexane/ethyl acetate to provide purified compound of formula Ik or Im.

Scheme VI

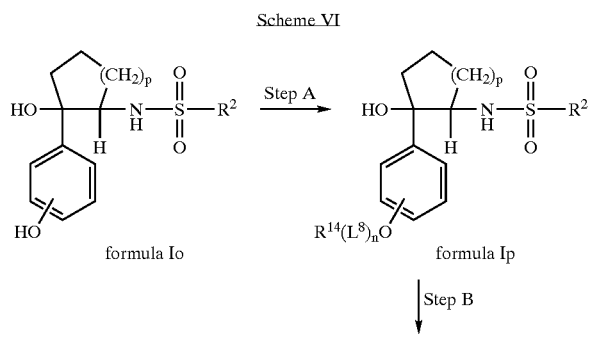

formula Io / formula Ip

Step B

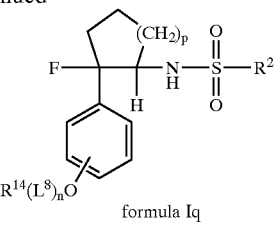

formula Iq

In Scheme VI, step A the compound of formula Io is alkylated under conditions well known in the art to provide the compound of formula Ip. For example, the compound of formula Io is dissolved with a suitable organic solvent, such as acetone and treated with about 1.1 to about 1.5 equivalents of a compound of formula $R^{14}(L_a)_n$—Lg wherein "Lg" refers to a suitable leaving group. Examples of suitable leaving groups include, Cl, Br, and the like. About 1.1 to about 1.5 equivalents of a suitable base, such as potassium carbonate are added and the reaction mixture is stirred at about 20° C. to about 40° C. for about 4 to 14 hours. The reaction is then filtered and the filtrated concentrated under vacuum to provide the crude compound of formula Ip. This crude material can then be purified by chromatography on silica gel with a suitable eluent, such as methylene chloride/ethyl acetate.

In Scheme VI, step B the compound of formula Ip is converted to the fluoro derivative of formula Iq in a manner analogous to the procedure set forth in Scheme I, step G.

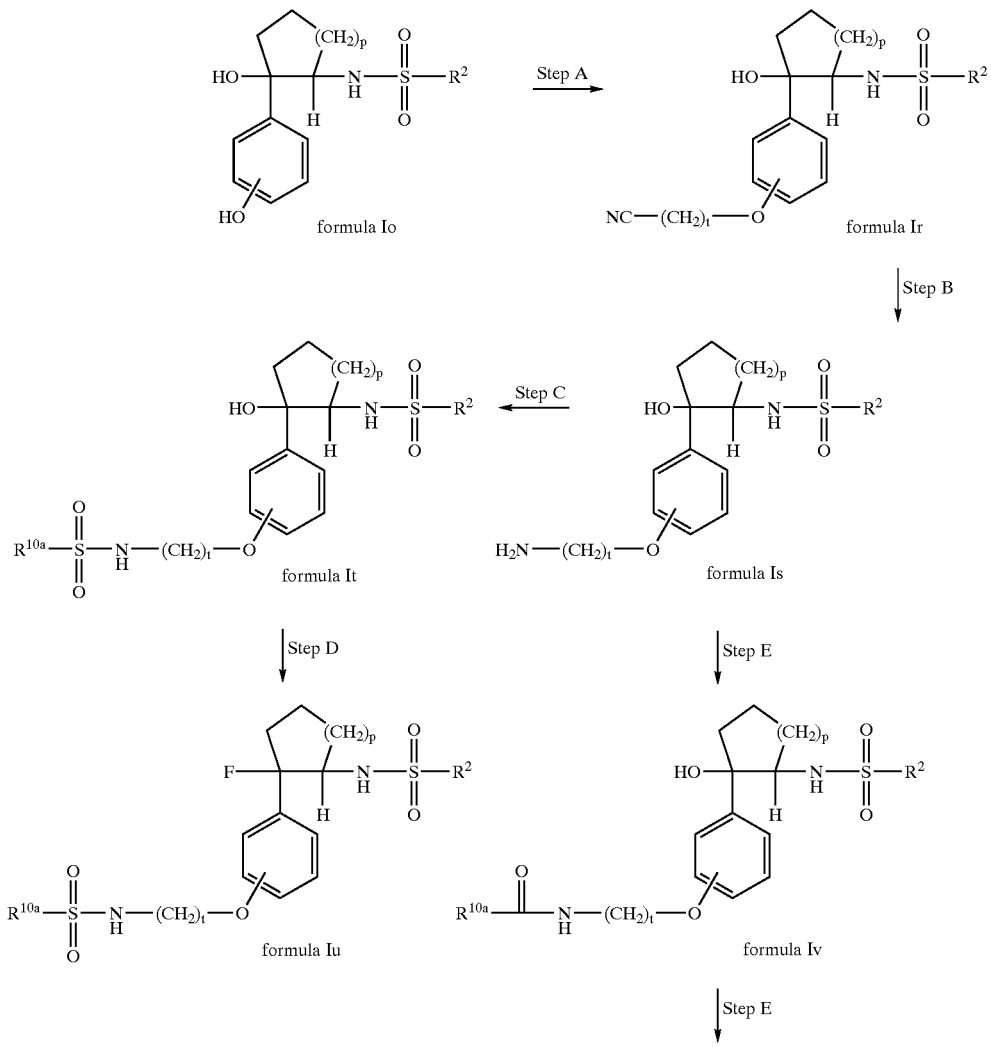

Scheme VII

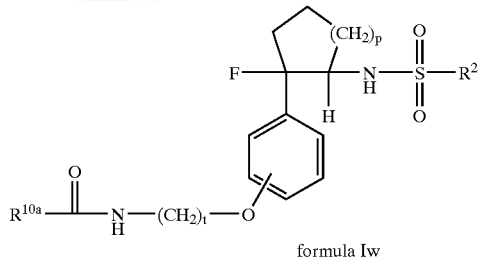

formula Iw

In Scheme VII, step A the compound of formula Io is alkylated under conditions well known in the art to provide the compound of formula Ir. For example, the compound of formula Io is dissolved in a suitable organic solvent, such as acetone and then treated with about 1.1 to about 1.5 equivalents of a compound of formula $NC(CH_2)_r$—Lg wherein "Lg" refers to a suitable leaving group. Examples of suitable leaving groups include, Cl, Br, and the like. The solution is then treated with about 1.1 to about 1.5 equivalents of a suitable base, such as potassium carbonate and the reaction mixture is stirred at about 20° C. to about 40° C. for about 4 to 14 hours. The reaction is then filtered and the filtrated concentrated under vacuum to provide the crude compound of formula Ir. This crude material can then be purified by chromatography on silica gel with a suitable eluent, such as methylene chloride/ethyl acetate.

In Scheme VII, step B compound of formula Ir is reduced under standard conditions to provide the compound of formula Is. For example, compound of formula Ir is dissolved in a suitable organic solvent, such as THF and treated with a slight excess of a suitable reducing agent, such as borane-THF. The reaction mixture is then stirred at room temperature for about 4 to 14 hours and then quenched with methanol. The reaction is then concentrated under vacuum and the residue purified by chromatography on silica gel with a suitable eluent, such as methylene chloride/ethyl acetate to provide the purified compound of formula Is.

In Scheme VII, step C, the compound of formula Is is sulfonylated in a manner analogous to the procedure set forth in Scheme I, step F to provide the compound of formula It.

In Scheme VII, step D, the compound of formula It is converted to the fluoro derivative of formula Iu in a manner analogous to the procedure set forth in Scheme I, step G.

In Scheme VII, step E the compound of formula Is is acylated under conditions well known in the art to provide the compound of formula Iv. For example, the compound of formula Is is dissolved in a suitable organic solvent, such as methylene chloride and cooled to about 0° C. To this cooled solution is added about 1.5 equivalents of a suitable base, such as triethylamine and about 1.1 to about 1.5 equivalents of a compound of formula $R^{10a}CO$—Lg wherein "Lg" refers to a suitable leaving group. Examples of suitable leaving groups include, Cl, Br, and the like. The reaction mixture is allowed to warm to room temperature and stir for about 2 to 4 hours. It is then diluted with methylene chloride, washed with water, the organic phase is dried over anhydrous sodium sulfate, filtered, and concentrated under vacuum to provide the crude compound of formula Iv. This crude material can then be purified by chromatography on silica gel with a suitable eluent, such as hexanes/ethyl acetate.

In Scheme VII, step E, the compound of formula Iv is converted to the fluoro derivative of formula Iw in a manner analogous to the procedure set forth in Scheme I, step G.

The following examples further illustrate the invention and represent typical syntheses of the compounds of formula I as described generally above. The reagents and starting materials are readily available to one of ordinary skill in the art. For example, see International Patent Application Publications: WO 98/33496 published Aug. 6, 1998; WO99/43285 published Sep. 2, 1999; and WO 00/06159, WO 00/06158, and WO 00/06148 all published Feb. 10, 2000. As used herein the term "Chromatotron®" (Harrison Research Inc., 840 Moana Court, Palo Alto, Calif. 94306) is recognized by one of ordinary skill in the art as an instrument which is used to perform centrifugal thin-layer chromatography. As used herein, the following terms have the meanings indicated: "eq" refers to equivalents; "g" refers to grams; "mg" refers to milligrams; "kPa" refers to kilopascals; "L" refers to liters; "mL" refers to milliliters; "μL" refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "PTSA" refers to p-toluenesulfonic acid: "THF" refers to tetrahydrofuran; "DMF" refers to N,N-dimethylformamide; "DMSO" refers to methyl sulfoxide; "LDA" refers to lithium diisopropylamide; "EtOAc" refers to ethyl acetate; "aq" refers to aqueous; "iPrOAc" refers to isopropyl acetate; "$PdCl_2(dppf)$" refers to [1,1'bis(diphenylphosphino)-ferrocene} dichloropalladium (II); "Ph" refers to phenyl; "$PPh_3$" refers to triphenylphosphine; "DEAD" refers to diethyl azodicarboxylate; "methyl DAST" refers to dimethylaminosulfur trifluoride, "DAST" refers to diethylaminosulfur trifluoride, "DBU" refers to 1,8-diazabicyclo[5.4.0]undec-7-ene; "TFA" refers to trifluoroacetic acid; "DME" refers to dimethoxyethane; "9-BBN" refers 9-borabicyclo[3.3.1]nonane; and "RT" refers to room temperature.

EXAMPLE 1

Preparation of Trans-[2-fluoro-2-(4-phenylphenyl)cyclohexyl][(methylethyl)sulfonyl]amine

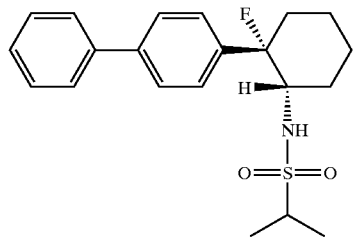

Preparation of 1-(4-phenylphenyl)cyclohexan-1-ol

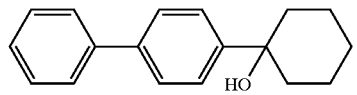

Scheme I, step A: Into a flame dried 250 mL 3 neck flask that was fitted with a thermometer and condenser, magnesium turnings (683 mg, 28.1 mmol) were placed in anhydrous THF (15 mL). While stirring at room temperature under a nitrogen atmosphere, a small amount of 4-diphenylbromide added dropwise along with one iodine crystal and dibromoethane (0.01 mL). This mixture was stirred vigorously and heated with a heat gun. Grignard was initiated as foaming was observed from metal turnings. The addition of 4-diphenylbromide was continued dropwise, keeping the temperature above 50° C. After the addition of 4-diphenylbromide (8.00 g, 31.7 mmol, total), the reaction was heated at reflux for 45 minutes to insure complete Grignard formation. The reaction was let cool to room temperature, and cyclohexanone (2.94 g, 30.0 mmol) in THF (30 mL) was added dropwise. After addition, reaction was refluxed for an additional 2 hours and then stirred overnight at room temperature. In the morning, enough saturated ammonium chloride in water was added to precipitate salts nicely and the organic layer was decanted off. The remaining salts were washed two times with ether and the combined organic layers were concentrated under reduced vacuum. The resulting semi-solid was taken into ethyl acetate, washed once with water, dried over potassium carbonate, filtered, and concentrated under reduced vacuum to yield 8.41 g as a semi-solid. This material was purified via silica gel chromatography employing the Water's Prep 2000 and eluting with a solvent of hexane/ethyl acetate 19:1 to yield the intermediate title compound (4.93 g, 62%) as a white solid. Fd M.S. 252.2 (M*).

Calculated for $C_{18}H_{20}O$: Theory: C 85.67, H 7.99. Found: C 86.35, H 8.16.

Preparation of 1-cyclohex-1-enyl-4-phenylbenzene

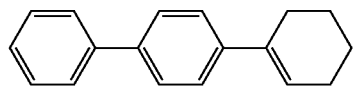

Scheme I, step B: 1-(4-Phenylphenyl)cyclohexan-1-ol (6.30 g, 24.9 mmol), p-toluenesulfonic acid (500 mg) and toluene (200 mL) were mixed together in a 500 mL 3 neck flask fitted with a thermometer and dean stark trap and stirred at reflux for 4 hours under a nitrogen atmosphere. The reaction was then let cool to room temperature and concentrated under reduced vacuum. The resulting semi-solid was taken into methylene chloride, washed once with water, dried over potassium carbonate, filtered, and concentrated under reduced vacuum to yield 6.13 g as a solid. This material was purified via silica gel chromatography employing the Water's Prep 2000 and eluting with a solvent of hexane/methylene chloride 9:1 to yield the intermediate title compound (5.80 g, 99%) as a white solid. Fd M.S. 234.2 (M*).

Calculated for $C_{18}H_{18}$: Theory: C 92.26, H 7.74. Found: C 91.98, H 7.37.

Preparation of 7-oxa-1-(4-phenylphenyl)bicyclo[4.1.0]heptane

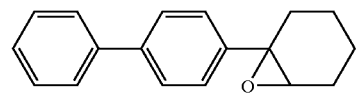

Scheme I, step C: Into a 500 mL 3 neck flask fitted with a stirrer, m-chloroperbenzoic acid (4.32 g, 3 equivalents) was added portion wise to sodium fluoride (1.78 g, 5 equivalents) in methylene chloride (250 mL) while stirring at room temperature under a nitrogen atmosphere. After 0.5 hour at this temperature, 1-cyclohex-1-enyl-4-phenylbenzene (2.00 g, 8.54 mmol) was added in one portion and the mixture was stirred for an additional 2.5 hours at this temperature. The mixture was then filtered and the filtrate was washed once with 1.0 N NaOH, once with water, dried over potassium carbonate, filtered, and concentrated under reduced vacuum to yield 2.1 g as an oil. This material was purified via silica gel chromatography employing the Water's Prep 2000 and eluting with a solvent of hexane/methylene chloride 7:3 to yield the intermediate title compound (1.37 g, 64%) as a clear oil. Fd M.S. 250.0 (M*). IR (C—O stretch at 1190 cm$^{-1}$).

Preparation of Trans-2-azido-1-(4-phenylphenyl)cyclohexan-1-ol (A) and Trans-2-azido-2-(4-phenylphenyl)cyclohexan-1-ol (B).

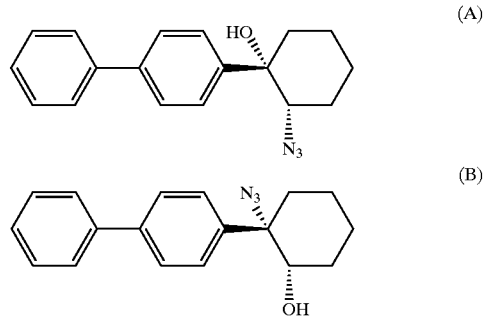

Scheme I, step D: Into a 100 mL 3 neck flask fitted with a stirrer and thermometer, sodium azide (1.66 g, 5 equivalents) in water (10 mL) was added dropwise to a stirred solution of 7-oxa-1-(4-phenylphenyl)bicyclo[4.1.0]heptane (1.35 g, 5.40 mmol) in DMF (40 mL) at room temperature. The reaction was then heated at 90° C. overnight. In the morning, the mixture was poured into water and the isomeric mix was extracted into ether. The organic layer was washed once with water, dried over potassium carbonate, filtered, and concentrated under reduced vacuum to yield 1.31 g as a brown oil. This material was used without further purification. Yield=Quantitative. Fd M.S. 292.9 (M*).IR (C—N stretch at 2100 cm$^{-1}$).

Preparation of Trans-2-amino-2-(4-phenylphenyl) cyclohexan-1-ol (Isomer 1) and Trans-2-amino-1-(4-phenylphenyl)cyclohexan-1-ol (isomer 2).

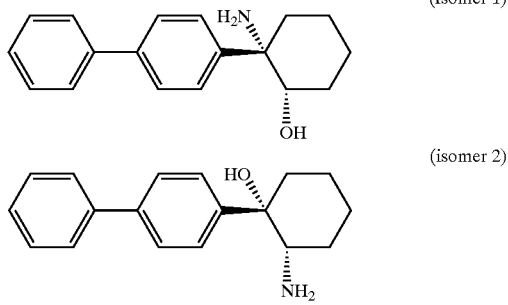

Scheme I, step E: Into a 100 mL 3 neck flask fitted with a stirrer and thermometer, the mixture of Trans-2-azido-1-(4-phenylphenyl)cyclohexan-1-ol (A) and Trans-2-azido-2-(4-phenylphenyl)cyclohexan-1-ol (1.30 g total) in toluene (20 mL) was added dropwise to a stirred solution of Red-Al® (5 mL, excess, Aldrich) at room temperature under a nitrogen atmosphere. The reaction was stirred for 1.0 hour. The mixture was poured into water and the desired isomeric mix was extracted into ethyl acetate. The organic layer was washed once with water, dried over potassium carbonate, filtered, and concentrated under reduced vacuum to yield 1.01 g as an oil. The two spot material (by thin layer chromatography) was purified via silica gel chromatography employing the Water's prep. 2000 while eluting with a solvent of methylene chloride/methanol 9:1 to yield the intermediate title compound (335 mg, the top spot, isomer 2) as a white solid. Ion spray M.S. 268.0 (M*+1).

Preparation of Trans-[2-hydroxy-2-(4-phenylphenyl) cyclohexyl][(methylethyl)sulfonyl]amine

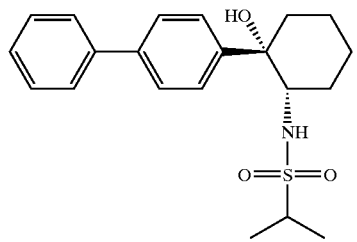

Scheme I, step F: In a 100 mL 3 neck flask fitted with a stirrer and thermometer, propanesulfonyl chloride (1.96 mg, 1.1 equivalents) was added dropwise to Trans-2-amino-1-(4-phenylphenyl)cyclohexan-1-ol (330 mg, 1.24 mmol) and DBU (226 mg, 1.2 equivalents) in methylene chloride (150 mL) while stirring at 0° C. under a nitrogen atmosphere. The reaction was allowed to warm to room temperature and stirred overnight at this temperature. In the morning, the reaction was diluted with methylene chloride (50 mL) and the organic layer was washed two times with water, dried over sodium sulfate, filtered, and concentrated under reduced vacuum to yield 412 mg of a viscous oil. This material was purified via silica gel chromatography employing the Chromatotron®, using a 4000 micron rotor and eluting with a solvent of methylene chloride/ethyl acetate 4:1 to yield the intermediate title compound (52 mg, 11%) as a white solid. Ion spray M.S. 372 (M*−1).

Preparation of Final Title Compound

Scheme I, step G: Into a 50 mL, 3 neck flask fitted with a stirrer and thermometer, Trans-[2-hydroxy-2-(4-phenylphenyl)cyclohexyl][(methylethyl)sulfonyl]amine (35 mg, 0.1 mmol) in methylene chloride (5 mL) was added dropwise to DAST (0.01 mL, excess) in methylene chloride (50 mL) while stirring at −78° C. under a nitrogen atmosphere. The reaction was allowed to warm to room temperature and diluted with methylene chloride (20 mL). This organic layer was washed with water, dried over sodium sulfate, filtered, and concentrated under reduced vacuum to yield 35.1 mg as an oil. This material was purified via silica gel chromatography employing the Chromatotron® and using a 1000 micron rotor while eluting with a solvent of methylene chloride to yield the final title compound (22.3 mg, 59%) as a white foam. Ion spray M.S. 374 (M*−1).

Calculated for $C_{21}H_{26}NO_2SF$: Theory: C 66.17, H 6.98, N 3.73. Found: C 66.61, H 6.86, N 3.76.

EXAMPLE 2

Preparation of Cis-[2-fluoro-2-(phenylphenyl) cyclohexyl][(methylethyl)sulfonyl]amine

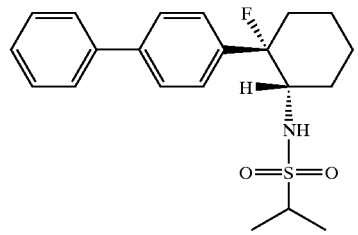

Preparation of 2-nitro-1-(4-phenylphenyl) cyclohexan-1-ol

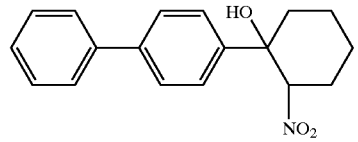

Scheme II, step A: Into a flame dried 500 mL 3 neck flask that was fitted with a thermometer and condenser, magnesium turnings (1.37 g, 56.2 mmol) were placed anhydrous THF (20 mL). While stirring at room temperature under a nitrogen atmosphere, a small amount of 4-diphenylbromide was added dropwise along with one iodine crystal and dibromoethane (0.01 mL). This mixture was stirred vigorously and heated with a heat gun. The Grignard was initiated as foaming was observed from metal turnings. The addition of 4-diphenylbromide was continued dropwise, keeping the temperature above 50° C. After the addition of 4-diphenylbromide (16.00 g, 63.4 mmol), the reaction was heated at reflux for 45 minutes to insure complete Grignard formation. The reaction was allowed to cool to room temperature, and 2-nitrocyclohexanone (8.58 g, 60 mmol) was added dropwise. After addition, reaction was refluxed for an additional 2 hours and then stirred overnight at room temperature. In the morning, enough saturated ammonium chloride in water was added to precipitate salts nicely and the organic layer was decanted off. The remaining salts were washed two times with ether and the combined organic layers were concentrated under reduced vacuum. The resulting semi-solid was taken into ethyl acetate, washed once with water, dried over potassium carbonate, filtered, and concentrated under reduced vacuum to yield 18.41 g as an oil. This material was purified via silica gel chromatography employing the Water's Prep 2000 and eluting with a solvent of hexane/ethyl acetate 19:1 to yield the intermediate title compound (4.01 g, 21%) as a white solid. Fd M.S. 296.2 (M*−1).

Preparation of Cis-2-amino-1-(4-phenylphenyl)cyclohexan-1-ol (A) and Trans-2-amino-1-(4-phenylphenyl)cyclohexan-1-ol (B)

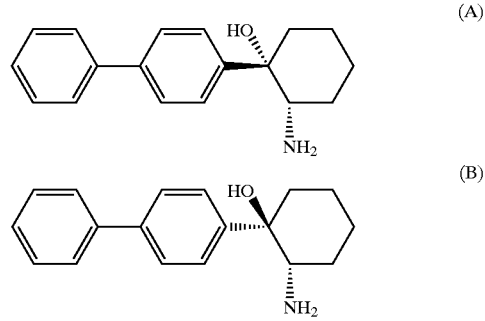

Scheme II, step B: 2-Nitro-1-(4-phenylphenyl)cyclohexan-1-ol (1.75 g, 5.89 mmol) was combined with ethanol (200 mL) and palladium on carbon (219 mg, 1.1 equivalents), and placed on the power shaker under a hydrogen atmosphere at 60 psi overnight. In the morning, the solution was filtered over a Celte® mat and the resulting filtrate was concentrated under reduced vacuum to yield 1.81 g as a viscous oil. The resulting isomeric mixture can then be separated via silica gel chromatography employing the Water's prep. 2000 and a solvent of methylene chloride/methanol to provide isomer A and isomer B.

Preparation of Cis-[2-hydroxy-2-4-phenylphenyl)cyclohexyl][(methylethyl)sulfonyl]amine

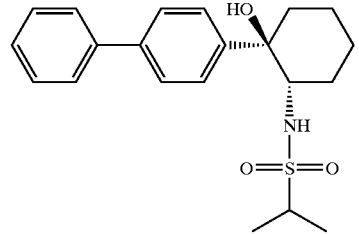

Scheme II, step C': In a 100 mL 3 neck flask fitted with a stirrer and thermometer, propanesulfonyl chloride (196 mg, 1.1 equivalents) is added dropwise to Cis-2-amino-1-(4-phenylphenyl)cyclohexan-1-ol (330 mg, 1.24 mmol) and DBU (226 mg, 1.2 equivalents) in methylene chloride (150 mL) while stirring at 0° C. under a nitrogen atmosphere. The reaction is allowed to warm to room temperature and stirred overnight at this temperature. In the morning, reaction is diluted with methylene chloride (50 mL) and the organic layer is washed two times with water, dried over sodium sulfate, filtered, and concentrated under reduced vacuum. This material can be purified via silica gel chromatography employing the Chromatotron®, using a 4000 micron rotor to provide the intermediate title compound.

Preparation of Final Title Compound

Scheme II, step D': Into a 50 mL, 3 neck flask fitted with a stirrer and thermometer, Cis-[2-hydroxy-2-(4-phenylphenyl)cyclohexyl][(methylethyl)sulfonyl]amine (35 mg, 0.1 mmol) in methylene chloride (5 mL) is added dropwise to DAST (0.01 mL, excess) in methylene chloride (50 mL) while stirring at −78° C. under a nitrogen atmosphere. The reaction is allowed to warm to room temperature and diluted with methylene chloride (20 mL). This organic layer is washed with water, dried over sodium sulfate, filtered, and concentrated under reduced vacuum. This material is purified via silica gel chromatography employing the Chromatotron® using a 1000 micron rotor to provide the final title compound.

EXAMPLE 3

Preparation of Trans-[2-fluoro-2-(4-phenylphenyl)cyclopentyl][(methylethyl)sulfonyl]amine

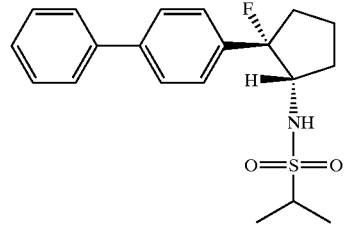

Preparation of 1(4-phenylphenyl)cyclopentan-1-ol

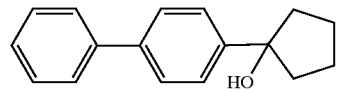

Scheme I, step A: Into a flame dried 500 mL 3n-flask that was fitted with a thermometer and condenser, magnesium turnings (1.36 g, 56.2 mmol) were placed in anhydrous THF (20 mL). While stirring at room temperature under a nitrogen atmosphere, a small amount of 4-diphenylbromide was added dropwise along with one iodine crystal and dibromoethane (0.01 mL). This mixture was stirred vigorously and heated with a heat gun. Grignard was initiated as foaming was observed from metal turnings. The addition of 4-diphenylbromide was continued dropwise, keeping the temperature above 50° C. After the addition of 4-diphenylbromide (16.00 g, 63.4 mmol, total), the reaction was heated at reflux for 45 minutes to insure complete Grignard formation. The reaction was allowed cool to room temperature, cyclopentanone (5.05, 60.0 mmol) was added dropwise. After addition, the reaction was heated at reflux for an additional 2 hours and then stirred overnight at room temperature. In the morning, enough saturated ammonium chloride in water was added to precipitate salts nicely and the organic layer was decanted off. The remaining salts were washed two times with ether and the combined organic layers were concentrated under reduced vacuum. The resulting semi-solid was taken into ethyl acetate, washed once with water, dried over potassium carbonate, filtered, and concentrated under reduced vacuum to yield 16.50 g as an oil. This material was purified via silica gel chromatography employing the Water's Prep 2000 and eluting with a solvent of hexane/ethyl acetate 4:1 to yield the intermediate title compound (7.50 g, 50%) as a yellow solid. Fd M.S. 221 (M*—OH).

Calculated for $C_{17}H_{18}O$: Theory: C 85.67, H 7.61. Found: C 85.61, H 7.61.

Preparation of 1-cyclopent-1-enyl-4-phenylbenzene

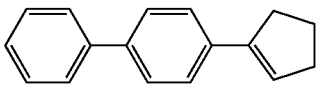

Scheme I, step B: 1-(4-Phenylphenyl)cyclopentan-1-ol (7.50 g, 31.5 mmol), p-toluenesulfonic acid (650 mg) and toluene (200 mL) were mixed together in a 500 mL 3 neck flask fitted with a thermometer and Dean Stark trap and stirred at reflux for 4 hours under a nitrogen atmosphere. The reaction was then allowed to cool to room temperature and concentrated under reduced vacuum. The resulting semi-solid was taken into methylene chloride, washed once with water, dried over potassium carbonate, filtered, and concentrated under reduced vacuum to yield 7.73 g as a solid. This material was purified via silica gel chromatography employing the Water's Prep 2000 and eluting with a solvent of hexane/methylene chloride 4:1 to yield the intermediate title compound (4.71 g, 68%) as a white solid. Fd M.S. 220.1 (M*).

Calculated for $C_{17}H_{16}$: Theory: C 92.68, H 7.32. Found: C 92.52, H 7.18.

Preparation of 6-oxa-1-(4-phenylphenyl)bicyclo [3.1.0]hexane

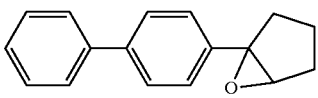

Scheme I, step C: Into a 1000 mL 3 neck flask fitted with a stirrer, m-chloroperbenzoic acid (12.50 g, 3 equivalents) was added portion wise to sodium fluoride (5.14 g, 5 equivalents) in methylene chloride (700 mL) while stirring at room temperature under a nitrogen atmosphere. After 0.5 hour at this temperature, 1-cyclopent-1-enyl-4-phenylbenzene (5.44 g, 24.7 mmol) was added in one portion and the mixture was stirred for an additional 2.5 hours at this temperature. The mixture was then filtered and the filtrate was washed once with 1.0 N NaOH, once with water, dried over potassium carbonate, filtered, and concentrated under reduced vacuum to yield 5.65 g as an oil. This material was purified via silica gel chromatography employing the Water's Prep 2000 and eluting with a solvent of hexane/methylene chloride 7:3 to yield the intermediate title compound (3.50 g, 60%) as a slowly crystallizing oil. Fd M.S. 237.1 (M*+1).

Calculated for $C_{17}H_{16}O$: Theory: C 86.41, H 6.82. Found: C 85.56, H 6.62.

Preparation of Trans-2-azido-1-(4-phenylphenyl) cyclopentan-1-ol (A) and Trans-2-azido-2-(4-phenylphenyl)cyclopentan-1-ol (B)

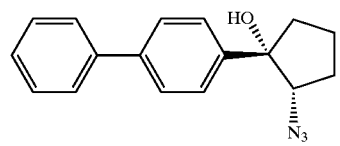

(A)

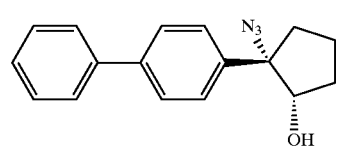

(B)

Scheme I, step D: Into a 100 mL 3 neck flask fitted with a stirrer and thermometer, sodium azide (1.66 g, 5 equivalents) in water (10 mL) is added dropwise to a stirred solution of 6-oxa-1-(4-phenylphenyl)bicyclo[3.1.0]hexane. (1.35 g, 5.70 mmol) in DMF (40 mL) at room temperature. The reaction is then heated at 90° C. overnight. In the morning, the mixture is poured into water and the isomeric mixture is extracted into ether. The organic layer is washed once with water, dried over potassium carbonate, and is concentrated under reduced vacuum. This material can be used without further purification.

Preparation of Trans-2-amino-2-(4-phenylphenyl) cyclopentan-1-ol (Isomer 1) and Trans-2-amino-1-(4-phenylphenyl)cyclopentan-1-ol (isomer 2)

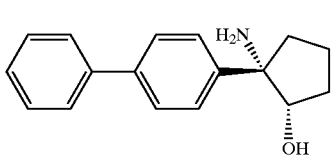

(Isomer 1)

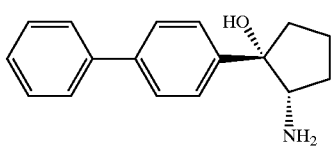

(isomer 2)

Scheme I, step E: Into a 100 mL 3 neck flask fitted with a stirrer and thermometer, trans-2-azido-1-(4-phenylphenyl) cyclopentan-1-ol (A) and trans-2-azido-2-(4-phenylphenyl) cyclopentan-1-ol (B) (1.35 g) in toluene (20 mL) is added dropwise to a stirred solution of 5 mL of Red-Al® at room temperature under a nitrogen atmosphere. The reaction is stirred for 1.0 hour. The mixture is then poured into water and the isomeric mix is extracted into ethyl acetate. The organic layer is washed once with water, dried over potassium carbonate, filtered, and concentrated under reduced vacuum. This crude material is purified and the isomers are separated via silica gel chromatography employing the Water's prep. 2000 to obtain each of the intermediate title compounds.

Preparation of Trans-[2-hydroxy-2-(4-phencyclopentyl][(methylethyl)sulfonyl]amine

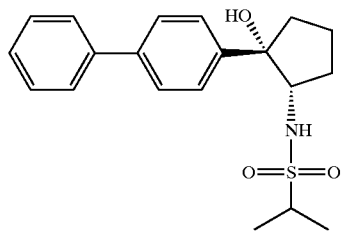

Scheme I, step F: In a 100 mL 3 neck flask fitted with a stirrer and thermometer propanesulfonyl chloride (196 mg, 1.1 equivalents) is added dropwise to trans-2-(4-phenylphenyl)cyclopentan-1-ol (330 mg, 1.30 mmol) and DBU (226 mg, 1.2 equivalents) in methylene chloride (150 mL) while stirring at 0° C. under a nitrogen atmosphere. The reaction is allowed to warm to room temperature and stirred overnight at this temperature. In the morning, reaction is diluted with methylene chloride (50 mL) and the organic layer is washed two times with water, dried over sodium sulfate, filtered, and concentrated under reduced vacuum. This material is purified via silica gel chromatography employing the Chromatotron® using a 4000 micron rotor and eluting with a solvent of methylene chloride/ethyl acetate 4:1. Cis-[2-hydroxy-2-(4-phenylphenyl)cyclopentyl][(methylethyl)sulfonyl]amine is prepared in an analogous manner.

Preparation of Final Title Compound

Scheme I, step G: Into a 50 mL 3 neck flask fitted with a stirrer and thermometer, trans-[2-hydroxy-2-(4-phenylphenyl)cyclopentyl][(methylethyl)sulfonyl]amine (35 mg, 0.1 mmol) in methylene chloride (5 mL) is added dropwise to DAST (0.01 mL, excess) in methylene chloride (50 mL) while stirring at −78° C. under a nitrogen atmosphere. The reaction is allowed to warm to room temperature and diluted with methylene chloride (20 mL). This organic layer is washed with water, dried over sodium sulfate, filtered, and concentrated under reduced vacuum. This material is purified via silica gel chromatography employing the Chromatotron® and using a 1000 micron rotor and eluting with a solvent of methylene chloride to yield the final title compound. Cis-[2-fluoro-2-(4-phenylphenyl)cyclopentyl][(methylethyl)sulfonyl]amine is prepared in an analogous manner.

EXAMPLE 4

Preparation of Trans-[(dimethylamino)sulfonyl][2-fluoro-2-(4-phenylphenyl)cyclohexyl]amine

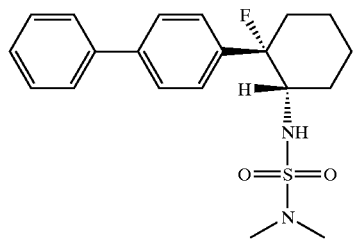

Scheme I, Step F: In a 500 mL 3 neck flask fitted with a stirrer and thermometer, dimethylsulfamoyl chloride (35 mg) is added dropwise to trans-2-amino-1-(4-phenylphenyl)cyclohexan-1-ol (500 mg, intermediate prepared in example 1) and 380 mg of DBU (380 mg) in THF (125 mL) while stirring at 0° C. under a nitrogen atmosphere. The reaction is allowed to warm to room temperature and stirred overnight at this temperature. In the morning, the reaction is concentrated under reduced vacuum. The crude residue is taken into ethyl acetate and the organic layer is washed two times with water, dried over Na$_2$SO$_4$, filtered, and concentrated under reduced vacuum. This material can be purified via silica gel chromatography employing the Chromatotron® and using a 2000 micron rotor while eluting with a solvent of hexane/ethyl acetate 3:1 to yield [(dimethylamino)sulfonyl][2-hydroxy-2-(4-phenylphenyl)cyclopentyl]amine.

Preparation of Final Title Compound

Scheme I, Step G: Into a 50 mL 3 neck flask fitted with a stirrer and thermometer, [(dimethylamino)sulfonyl][2-hydroxy-2-(4-phenylphenyl)cyclopentyl]amine (200 mg) in methylene chloride (10 mL) is added dropwise to DAST (0.08 mL) in methylene chloride (10 mL) while stirring at −78° C. under a nitrogen atmosphere. The reaction is allowed to warm to room temperature and diluted with methylene chloride (25 mL). This organic layer is washed with water, dried over Na$_2$SO$_4$, filtered, and concentrated under reduced vacuum. This crude material can be purified via silica gel chromatography employing the Chromatotron® and using a 2000 micron rotor while eluting with a solvent of hexane/ethyl acetate 3:1 to provide the final title compound.

EXAMPLE 5

Preparation of Trans-(2-fluoro-2-phenylcyclohexyl)[(methylethyl)sulfonyl]amine

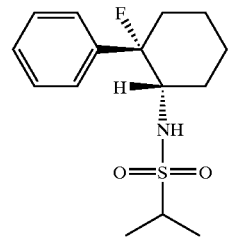

Preparation of 1-phenylcyclohexan-1-ol

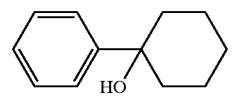

Scheme I, step A: Into a flame dried 250 mL 3 neck flask fitted with a thermometer and condenser, magnesium turnings (683 mg, 28.1 mmol) are placed in anhydrous THF (15 mL). While stirring at room temperature under a nitrogen atmosphere, a small amount of phenylbromide is added dropwise along with one iodine crystal and dibromoethane (0.01 mL). This mixture is stirred vigorously and heated with a heat gun. Grignard is initiated when foaming is observed from metal turnings. The addition of phenylbromide is continued dropwise, keeping the temperature above 50° C. After the addition of phenylbromide (31.7 mmol, total), the reaction is heated at reflux for about 45 minutes to insure complete Grignard formation. The reaction is then allowed to cool to room temperature, and cyclohexanone (2.94 g, 30.0 mmol) is added dropwise. After addition, the reaction is refluxed for an additional 2 hours and then stirred overnight at room temperature. In the morning, enough saturated ammonium chloride in water is added to precipitate salts nicely and the organic layer is decanted off. The remaining salts are washed two times with ether and the combined organic layers are concentrated under reduced vacuum. The resulting semi-solid is taken into ethyl acetate, washed once with water, dried over potassium carbonate, filtered, and concentrated under reduced vacuum. The crude material can then be purified via silica gel chromatography employing the Water's Prep 2000 and eluting with a solvent of hexane/ethyl acetate 19:1 to yield the intermediate title compound.

Preparation of Cyclohex-1-enylbenzene

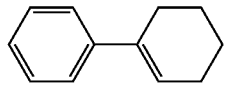

Scheme I, step B: 1-phenylcyclohexan-1-ol (24.9 mmol), p-toluenesulfonic acid (500 mg) and toluene (200 mL) are mixed together in a 500 mL 3 neck flask fitted with a thermometer and Dean Stark trap and stirred at reflux for 4 hours under a nitrogen atmosphere. The reaction is then allowed to cool to room temperature and concentrated under reduced vacuum. The crude material is then taken into methylene chloride, washed once with water, dried over potassium carbonate, filtered, and concentrated under reduced vacuum. This material can then be purified via silica gel chromatography employing the Water's Prep 2000 and eluting with a solvent of hexane/methylene chloride 9:1 to yield the intermediate title compound.

Preparation of 7-Oxa-1-phenylbicyclo[4.1.0]heptane

Scheme I, step C: Into a 500 mL 3 neck flask fitted with a stirrer, m-chloroperbenzoic acid (4.32 g, 3 equivalents) is added portion wise to sodium fluoride (1.78 g, 5 equivalents) in methylene chloride (250 mL) while stirring at room temperature under a nitrogen atmosphere. After 0.5 hour at this temperature, cyclohex-1-enylbenzene (8.54 mmol) is added in one portion and the mixture is stirred for an additional 2.5 hours at this temperature. The mixture is then filtered and the filtrate is washed once with 1.0 N NaOH, once with water, dried over potassium carbonate, filtered, and concentrated under reduced vacuum. The crude material can be purified via silica gel chromatography employing the Water's Prep 2000 and eluting with a solvent of hexane/methylene chloride 7:3 to yield the intermediate title compound.

Preparation of Trans-2-azido-1-phenylcyclohexan-1-ol (A) and Trans-2-azido-2-phenylcyclohexan-1-ol (B)

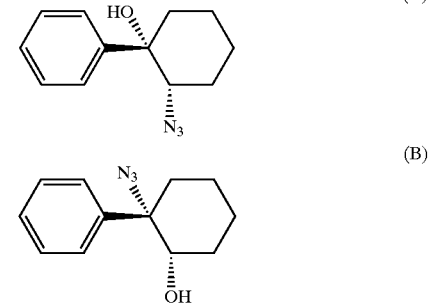

Scheme I, step D: Into a 100 mL 3 neck flask fitted with a stirrer and thermometer, sodium azide (1.66 g, 5 equivalents) in water (10 mL) is added dropwise to a stirred solution of 7-oza-1-phenylbicyclo[4.1.0]heptane (5.40 mmol) in DMF (40 mL) at room temperature. The reaction is then heated at 90° C. overnight. In the morning, the mixture is poured into water and the isomeric mix is extracted into ether. The organic layer is washed once with water, dried over potassium carbonate, filtered, and concentrated under reduced vacuum to yield material that can be used in the next step without further purification.

Preparation of Trans-2-amino-2-phenylcyclohexan-1-ol (Isomer 1) and Trans-2-amino-1-phenylcyclohexan-1-ol (Isomer 2)

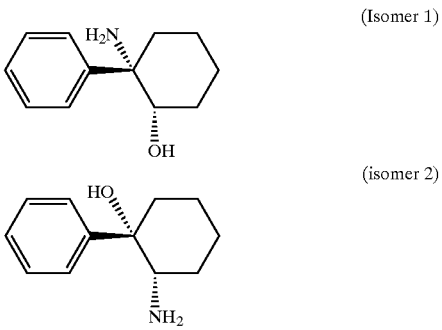

Scheme I, step E: Into a 100 mL 3 neck flask fitted with a stirrer and thermometer, the mixture of Trans-2-azido-1-phenylcyclohexan-1-ol (A) and Trans-2-azido-2-phenylcyclohexan-1-ol (B) (1.30 g total) in toluene (20 mL) is added dropwise to a stirred solution of Red-Al® (5 mL, excess, Aldrich) at room temperature under a nitrogen atmosphere. The reaction is stirred for 1.0 hour. The mixture is poured into water and the desired isomeric mix is extracted into ethyl acetate. The organic layer is washed once with water, dried over potassium carbonate, filtered, and concentrated under reduced vacuum. The crude material is purified via silica gel chromatography employing the Water's prep. 2000 while eluting with a solvent of methylene chloride/methanol 9:1 to yield the intermediate title compound as a white solid.

Preparation of Trans-(2-hydroxy-2-phenylcyclohexyl)[(methylethyl)sulfonyl]amine

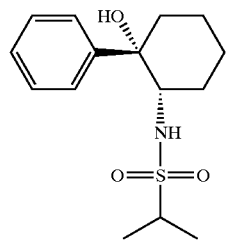

Scheme I, step F: Into a 100 mL 3 neck flask fitted with a stirrer and thermometer, propanesulfonyl chloride (1.96 mg, 1.1 equivalents) is added dropwise to Trans-2-amino-1-phenylcyclohexan-1-ol (isomer 2) (1.24 mmol) and DBU (226 mg, 1.2 equivalents) in methylene chloride (150 mL) while stirring at 0° C. under a nitrogen atmosphere. The reaction is allowed to warm to room temperature and stirred overnight at this temperature. In the morning, the reaction is diluted with methylene chloride (50 mL) and the organic layer is washed two times with water, dried over sodium sulfate, filtered, and concentrated under reduced vacuum. The material is purified via silica gel chromatography employing the Chromatotron®, using a 4000 micron rotor and eluting with a solvent of methylene chloride/ethyl acetate 4:1 to provide the intermediate title compound.

Preparation of Final Title Compound

Scheme I, step G: Into a 50 mL, 3 neck flask fitted with a stirrer and thermometer, Trans-(2-hydroxy-2-phenylcyclohexyl)[(methylethyl)sulfonyl]amine (0.1 mmol) in methylene chloride (5 mL) is added dropwise to DAST (0.01 mL, excess) in methylene chloride (50 mL) while stirring at −78° C. under a nitrogen atmosphere. The reaction is allowed to warm to room temperature and diluted with methylene chloride (25 mL). This organic layer is washed with water, dried over $Na_2SO_4$, filtered, and concentrated under reduced vacuum. This crude material can be purified via silica gel chromatography employing the Chromatotron® and using a 2000 micron rotor while eluting with a solvent of hexane/ethyl acetate 3:1 to provide the final title compound.

EXAMPLE 6

Preparation of [2-Fluoro-2-(4-nitrophenyl)cyclohexyl][(methylethyl)sulfonyl]amine

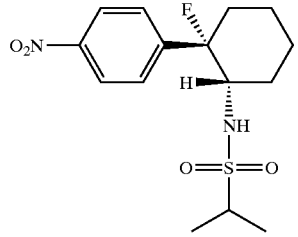

Scheme III, step A: To a round-bottom flask equipped with stir rod, thermocouple and nitrogen purge at 25° C., is charged Trans-(2-fluoro-2-phenylcyclohexyl)[(methylethyl)sulfonyl]amine (0.0207 mol), trifluoroacetic acid (15 mL), dichloromethane (1.2 mL) and heptane (8 mL). The reaction mixture is cooled to −5° C. and 98% fuming nitric acid (1.60 g, 0.0249 mol) is added dropwise. The reaction mixture is stirred at −5 to +5° C. for 3–5 hours and then warmed to 20–25° C. The reaction is allowed to stir for an additional 3 to 6 hours.

The reaction mixture is then diluted with dichloromethane (20 mL) and deionized water (20 mL), and the mixture is transferred to a suitably sized 3-neck bottom outlet round-bottom flask. The mixture is stirred for 10–15 minutes. The aqueous phase is then separated, extracted with dichloromethane (1×20 mL), and the organic phases are combined. To the organic phase is added water (15 mL), 10% NaOH (10 mL), and the pH is adjusted to 6.5–7.5 with saturated sodium carbonate. After 10–15 minutes of stirring, the organic layer is separated and concentrated under reduced pressure to provide the title compound.

EXAMPLE 7

Preparation of [2-Fluoro-2-(4-aminophenyl)cyclohexyl][(methylethyl)sulfonyl]amine

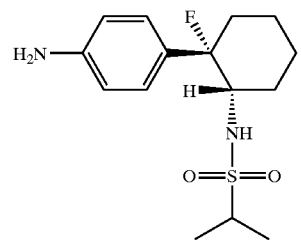

Scheme III, step B: [2-Fluoro-2-(4-nitrophenyl)cyclohexyl][(methylethyl)sulfonyl]amine (prepared in example 6) is diluted with ethanol and was transferred to a Parr bottle containing 1.25 g of 5% Pd on C (rinsed in with 5 mL of THF) under nitrogen (total ethanol=45 mL). The reaction mixture is then hydrogenated for 16–20 hours at 20–25° C. The reaction mixture is then filtered and the filtrate concentrated under vacuum. The residue can then be purified by flash chromatography on silica gel with ethyl acetate/hexanes to provide the final title compound.

EXAMPLE 8

Preparation of (3,5-Difluorophenyl)-N-[4-(1-fluoro-2-{[(methylethyl)sulfonyl]amino}cyclohexyl)phenyl]carboxamide

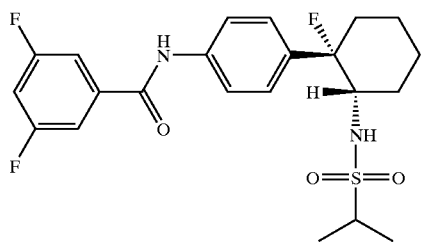

Scheme IV: To a 0° C. solution of [2-fluoro-2-(4-aminophenyl)cyclohexyl][(methylethyl)sulfonyl]amine (0.0838 mol, from example 7) and triethylamine (9.75 g, 13.4 mL, 0.0964 mol) in $CH_2Cl_2$ (86 mL) is added 3,5-difluorobenzoyl chloride (16.3 g, 0.0922 mol) dropwise over 30 min. After the addition is complete, the reaction mixture is allowed to stir at 20° C. for 1 hour. The reaction mixture is washed with deionized water (2×100 mL) and 0.1 N HCl (2×100 mL). The organic phase is diluted with acetone (50 mL) to ensure complete dissolution of the product and the organic phase is washed with saturated $K_2CO_3$ (100 mL), 0.1 N HCl (100 mL), dried ($MgSO_4$, 3 g), filtered and concentrated under vacuum. The residue can then be purified by flash chromatography on silica gel with a suitable eluent, such as ethyl acetate/hexane to provide the title compound.

EXAMPLE 9

Preparation of [2-Fluoro-2-(4-bromophenyl)cyclohexyl][(methylethyl)sulfonyl]amine

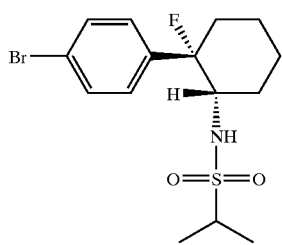

The title compound can be prepared in a manner analogous to the procedure disclosed by Wu and Mosher, *J. Org. Chem.*, 51, 1904 (1986). For example, a 50 mL, 3-neck flask is charged with [2-fluoro-2-(4-aminophenyl)cyclohexyl][(methylethyl)sulfonyl]amine (1.24 mmoles, from example 7) followed by 6N HCl (4.9 mL, 29.3 mmoles). The solution is then cooled to 0° C. and is stirred for about 15 to 30 minutes and a solution comprised of sodium nitrite (102 mg, 1.48 mmoles) in water (2 mL) is added dropwise to the reaction mixture. After about 15 minutes, urea (97 mg, 1.6 mmoles) is added to destroy excess nitrite and the solution is stirred for an additional 30 minutes.

The mixture is then transferred to a 0° C. acetone solution (20 mL) within another 50 mL 3-neck round-bottom flask. To this solution is added a mixture of CuBr (265 mg, 1.85 mmoles) and LiBr (172 mg, 1.98 moles) in two portions. The mixture is allowed to stir for an hour at 0° C. The reaction mixture is then concentrated under vacuum, diluted with ethyl acetate and washed with water (2×50 mL), aqueous sodium bicarbonate (1×50 mL) and brine (1×50 mL). The organic phase is separated, dried over magnesium sulfate, filtered, and concentrated to provide the title compound.

EXAMPLE 10

Preparation of {2-Fluoro-2-[4-(4-{2-[(methylsulfonyl)amino]ethyl}phenyl)phenyl]cyclohexyl}[(methylethyl)sulfonyl]amine

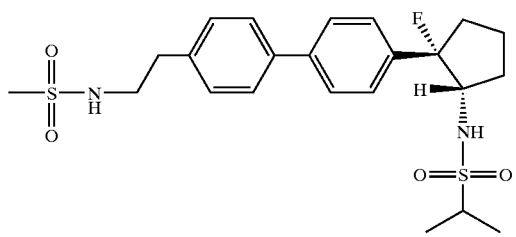

Preparation of (Methylsulfonyl)(2-phenylethyl)amine

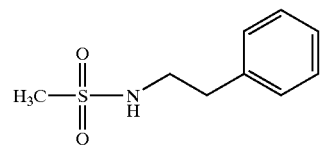

To a 10° C. solution of phenethylamine (12.1 g, 0.100 mol) and triethylamine (11.1 g, 0.110 mol) in $CH_2Cl_2$ (50 mL) was added methanesulfonyl chloride (12.6 g, 0.110 mol) dropwise over 10 min. The solution was stirred at room temperature for 1.5 h and was then washed with 1 N HCl (5×20 mL). The organic phase was directly concentrated to provide the intermediate title compound, (methylsulfonyl)(2-phenylethyl)amine, (21.2 g, 93.3%) as an oil. $^1$H NMR ($CDCl_3$, 300 MHz) δ7.32 (m, 2H), 7.23 (m, 3H), 4.30 (br s, 1H), 3.40 (t, 2H, J=3.9), 2.88 (t, 2H, J=4.2), 2.81 (s, 3H).

Preparation of [2-(4-Iodophenyl)ethyl](methylsulfonyl)amine

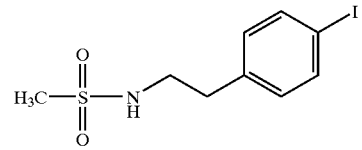

To a stirring room temperature solution of (methylsulfonyl)(2-phenylethyl)amine (205 g, 1.03 moles), water (200 mL), 95% sulfuric acid (111 g, 1.08 moles) in acetic acid (1 L), was added iodine (111 g, 0.438 mol) and periodic acid ($H_5IO_6$, 45.6 g, 0.206 mol). The reaction mixture was warmed to 70–75° C. for 3 h. The heat was removed and the dark violet reaction mixture was allowed to proceed overnight at room temperature. Potassium hydroxide pellets (85%, 143 g, 2.16 moles) were added to neutralized the sulfuric acid and then enough saturated aqueous sodium sulfite was added to decolorize the mixture to afford a white suspension. The suspension was cooled to 15° C. and filtered. The filter cake was triturated thoroughly with water and was then dissolved in $CH_2Cl_2$ (1 L) and extracted with additional water (2×200 mL). The organic phase was concentrated under reduced pressure to provide the intermediate title compound, [2-(4-iodophenyl)ethyl](methylsulfonyl)amine, (201 g, 60.2%) as a white powder. $^1$H NMR ($CDCl_3$, 300 MHz) δ 7.64 (d, 2H, J=4.8), 6.97 (d, 2H, J=5.1), 4.37 (br t, 1H, J=4), 3.36 (app. q, 2H, J=3.9), 2.85 (s, 3H), 2.82 (t, 2H, J=3.9).

Preparation of (Tert-butoxy)-N-[2-(4-iodophenyl) ethyl]-N-(methylsulfonyl)carboxamide

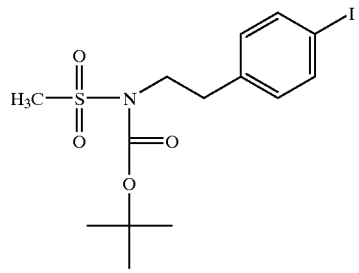

A room temperature solution of [2-(4-iodophenyl)ethyl] (methylsulfonyl)amine (201 g, 0.618 mol), 4-dimethylaminopyridine (3.8 g, 0.031 mol) and di-tert-butyl dicarbonate (162 g, 0.744 mol) in $CH_2Cl_2$ (1 L), was allowed to stir overnight. The reaction mixture was washed with water (2×400 mL) and the organic phase was concentrated to about 600 mL and hexanes (400 mL) was added. This combined solution was washed again with water (400 mL) and was concentrated to a solid that was suspended in hexanes (600 mL) and filtered. The collected solids were dried under reduced pressure to afford the intermediate title compound, (tert-butoxy)-N-[2-(4-iodophenyl)ethyl]-N-(methylsulfonyl)carboxamide (241.5 g, 91.5%) as a white solid. $^1H$ NMR ($CDCl_3$, 300 MHz) δ 7.63 (d, 2H, J=7.8), 6.98 (d, 2H, J=7.8), 3.88 (t, 2H, J=6.9), 3.10 (s, 3H), 2.88 (t, 2H, J=6.9), 1.51 (s, 9H).

Preparation of (Tert-butoxy)-N-(methylsulfonyl)-N-{2-[4-(4,4,5,5-tetramethyl(1,3,2-dioxaborolan-2-yl) phenyl]ethyl}carboxamide

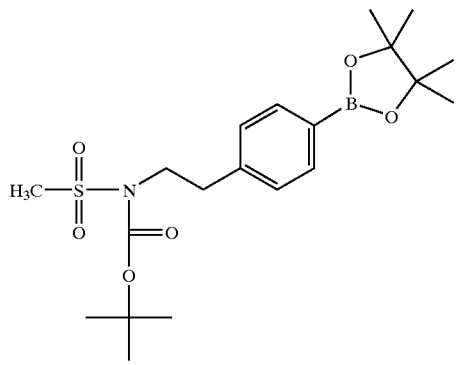

To a degassed solution of (tert-butoxy)-N-[2-(4-iodophenyl)ethyl]-N-(methylsulfonyl)carboxamide (128 g, 0.300 mol), triethylamine (91.1 g, 0.900 mol), and 1,1'-bis (diphenylphosphino) ferrocenedichloropalladium (II)—$CH_2Cl_2$ complex (2.9 g, 0.0035 mol) in acetonitrile (600 mL) was added pinacolborane (50 g, 0.391 mol) dropwise. The mixture was stirred at 70–74° C. for 8 h and then was cooled to room temperature. The reaction mixture was concentrated to a fluid oil that was partitioned between MTBE (500 mL) and water (500 mL). The organic phase was separated and washed with water (2×200 mL) and concentrated to a residue that was partially dissolved with heptane (1 L). The heptane soluble fraction was filtered through Celite® 521 and concentrated to an oil (95 g). The residue was dissolved in acetone (600 mL) and heptane (600 mL) and filtered through Celite® 521. The combined filtrates were concentrated to 95 g of a mixture of a 3:1 molar ratio ($^1H$ NMR, 81.0% by weight) of intermediate title compound, (tert-butoxy)-N-(methylsulfonyl)-N-{2-[4-(4,4,5,5-tetramethyl(1,3,2-dioxaborolan-2-yl))phenyl] ethyl}carboxamide, (60.3% potency corrected yield) and protio derivative. $^1H$ NMR ($CDCl_3$, 300 MHz) δ 7.75 (d, 2H, J=7.8), 7.23 (d, 2H, J=8.1), 3.87 (t, 2H, J=8.1), 2.99 (s, 3H), 2.90 (t, 2H, J=7.5), 1.53 (s, 9H), 1.33 (s, 6H), 1.27 (s, 6H).

Preparation of (Methylsulfonyl){2-[4-(4,4,5,5-tetramethyl(1,3,2-dioxaborolan-2-yl)phenyl] ethyl}amine

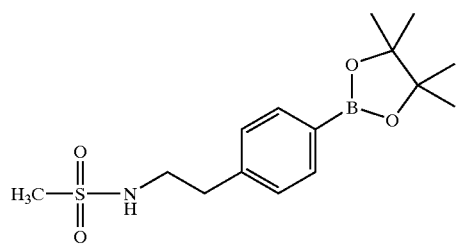

To a 2 L flask charged with a stirring solution of (tert-butoxy)-N-(methylsulfonyl)-N-{2-[4-(4,4,5,5-tetramethyl (1,3,2-dioxaborolan-2-yl))phenyl]ethyl}carboxamide (98.7 g, 0.232 mol) in $CH_2Cl_2$ (500 mL) was added trifluoroacetic acid (82 mL, 121.4 g, 1.06 moles) dropwise from an addition funnel. No exotherm was observed and the reaction solution was allowed to stir at room temperature for 18 h.

HPLC analysis indicated 98% completion so the cooled (5° C.) reaction mixture was neutralized by the slow addition of 5N NaOH (175 mL). The pH of the aqueous phase was 10.5. The phases were separated and the aqueous phase was extracted with $CH_2Cl_2$ (50 mL). The combined $CH_2Cl_2$ phases were washed with brine (2×100 mL) and water (1×100 mL). The $CH_2Cl_2$ phase was diluted with heptane (300 mL) and was concentrated under reduced pressure to afford a suspension that was isolated by filtration. The collected solids were washed with pentane (2×100 mL) and dried under vacuum to provide the intermediate title compound (methylsulfonyl){2-[4-(4,4,5,5-tetramethyl(1,3,2-dioxaborolan-2-yl))phenyl]ethyl}amine, (69.0 g, 91.4%) as a white powder. $^1H$ NMR ($CDCl_3$, 300 MHz) δ 7.77 (d, 2H, J=8.1), 7.22 (d, 2H, J=7.8), 4.26 (br t, 1H, J=6), 3.40 (q, 2H, J=6.9), 2.89 (t, 2H, J=6.6), 2.82 (s, 3H), 1.34 (s, 12H).

Preparation of 4-{2-[(Methylsulfonyl)amino] ethyl}benzene Boronic Acid

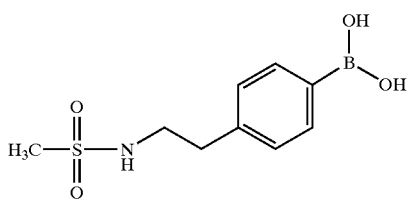

(Methylsulfonyl){2-[4-(4,4,5,5-tetramethyl(1,3,2-dioxaborolan-2-yl))phenyl]ethyl}amine (68.0 g, 0.209 mol) was placed into a 2L flask and combined with acetone (600 mL), 1N ammonium acetate (600 mL), and $NaIO_4$ (168.1 g, 0.786 mol). This mixture was stirred at room temperature overnight. The reaction mixture was filtered to remove insoluble matter to afford filtrate A. The collected solids were washed with acetone (2×100 mL) and this filtrate was combined with filtrate A. The combined filtrates were concentrated under reduced pressure to 600 mL to afford a precipitate that was recovered by filtration. The collected solids were air-dried to give 110 g of crude material. This crude material was suspended in water (100 mL) and 5N NaOH was added until the pH was 12.5. The resulting suspension was filtered and the filtrate was treated with decolorizing carbon (Darco 6-60). The mixture was filtered and the filtrate was diluted with 10N $H_2SO_4$ until the pH was 5.0 to precipitate the intermediate title compound. This precipitate was collected by filtration and dried under reduced pressure to provide the intermediate title compound, 4-{2-[(methylsulfonyl)amino]ethyl}benzene boronic acid, (41.9 g, 82.5%) as a white powder. $^1$H NMR (acetone-$d_6$, 300 MHz) δ 7.82 (d, 2H, J=8.4), 7.27 (d, 2H, J=7.8), 7.11 (s, 2H), 6.03 (m, 1H), 3.36 (m, 2H), 2.91 (m, 2H), 2.84 (s, 3H).

Preparation of Final Title Compound

Scheme V, step B: An aqueous solution of potassium formate is prepared in the following manner. To 15 mL of water is added KOH (85% flakes, 6.73 g, 0.102 mol), then 98% formic acid (4.70 g, 0.102 mol). Alternatively, one may use commercially available potassium formate. To this solution is then added $K_2CO_3$ (2.76 g, 0.0210 mol), 4-{2-[(methylsulfonyl)amino]ethyl}benzene boronic acid (4.62 g, 0.190 mol), 1-propanol (100 mL), and [2-fluoro-2-(4-bromophenyl)cyclohexyl][(methylethyl)sulfonyl]amine (0.200 mol, prepared in example 9). This mixture is deoxygenated via about three vacuum/$N_2$-refill cycles. Palladium black (0.0215 g, 0.0002 mol) is added and the mixture is again deoxygenated via three vacuum/$N_2$-refill cycles. The reaction flask is heated in a preheated oil bath at 88° C. and the mixture is stirred overnight.

The mixture is then diluted with ethyl acetate and filtered through Celite® to remove palladium. The mixture is concentrated under reduced pressure and the resulting residue is partitioned between ethyl acetate and water. The organic phase is concentrated and the crude residue is purified by flash chromatography on silica gel with a suitable eluent, such as ethyl acetate/hexanes, or recrystallized from a suitable solvent mixture such as acetone/water to provide the purified final title compound.

EXAMPLE 11

Preparation of [2-Fluoro-2-(4-phenylphenyl)cyclopentyl][(methylethyl)sulfonyl]amine

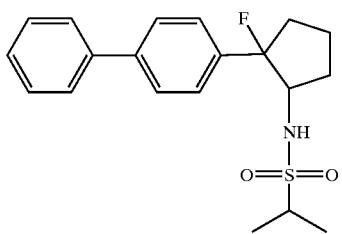

Preparation of [(Methylethyl)sulfonyl][2-(phenylmethoxy)cyclopentyl]amine

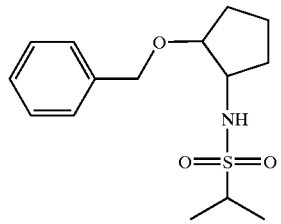

Scheme IA, step A: In a 250 mL 3 neck flask fitted with a stirrer and thermometer, propanesulfonyl chloride (4.47 g, 1.2 eq) was added dropwise to (1S,2S)-2-benzyloxycyclopentylamine (5.00 g, 10 mmol) and DBU (5.98 g, 1.5 eq) in $CH_2Cl_2$ (100 mL) while stirring at 0° C. under a nitrogen atmosphere. The reaction was allowed to warm to room temperature and stirred overnight at this temperature. In the morning, the reaction was diluted with $CH_2Cl_2$ (100 mL) and the organic layer was washed two times with $H_2O$, dried over $Na_2SO_4$, filtered, and concentrated under reduced vacuum to yield 10.13 g as a viscous oil. This material was purified via silica gel chromatography employing the Water's Prep. 2000 and eluting with a solvent of hexane/ethyl acetate 4:1 to yield the intermediate title compound (8.0 g, 95%) as a white solid. Ion spray M.S. 296 (M*−1). Analysis calculated for $C_{15}H_{23}NO_3S$: Theory: C, 60.58; H, 7.80; N, 4.71. Found: C, 60.39; H, 7.79; N, 4.73.

Preparation of (2-Hydroxycyclopentyl)[(methylethyl)sulfonyl]amine

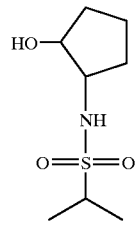

Scheme IA, step B: [(Methylethyl)sulfonyl][2-(phenylmethoxy)cyclopentyl]amine (2.00 g, 6.72 mmol), palladium on carbon (250 mg) and ethanol (50 mL) were combined and placed on the power shaker under a hydrogen atmosphere at 60 psi's overnight. In the morning, the solution was filtered over a Celite® mat and the resulting filtrate was concentrated under reduced vacuum to yield 1.50 g as a viscous oil. TLC showed material was very pure and was used without further purification. Yield= Quantitative. Ion spray M.S. 206 (M*−1). Analysis calculated for $C_8H_{17}NO_3S$: Theory: C, 46.35; H, 8.26; N, 6.75. Found: C, 46.27; H, 7.97; N, 6.70.

53
Preparation of 2-{[(Methylethyl)sulfonyl]amino}cyclopentan-1-one

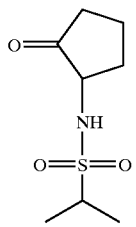

Scheme IA, step C: Into a 250 mL single neck flask, (2-hydroxycyclopentyl)[(methylethyl)sulfonyl]amine (1.5 g, 7.24 mmol), pyridinium chlorochromate (2.34 g, 1.5 eq) and methylene chloride (100 mL) were mixed together and stirred for 4 hours at room temperature under a nitrogen atmosphere. The solution was then filtered over a Celite® mat and the resulting filtrate was washed once with water, dried over potassium carbonate, and concentrated under reduced vacuum to yield 1.31 g as an oil. This material was purified via silica gel chromatography employing the Chromatotron® and using a 4000 micron rotor while eluting with a solvent of methylene chloride/ethyl acetate 4:1 to yield the intermediate title compound (450 mg, 30%) as a slowly crystallizing oil. Ion spray M.S. 204 (M*−1). Analysis calculated for $C_8H_{15}NO_3S$: Theory: C, 46.81; H, 7.37; N, 6.82. Found: C, 46.08; H, 7.12; N, 6.58.

Alternative Preparation of 2-{[(Methylethyl)sulfonyl]amino}cyclopentan-1-one

Scheme IA, step C: Into a flame dried 500 mL 3 neck flask fitted with a thermometer and magnetic stirrer, DMSO (6.16 mL) in methylene chloride (20 mL) was added dropwise to oxalyl chloride (3.80 mL) in methylene chloride (100 mL) while stirring at −55° C. under a nitrogen atmosphere. After 2 minutes, (2-hydroxycyclopentyl)[(methylethyl)sulfonyl]amine (8.00 g, 38.6 mmol) in methylene chloride (45 mL) was added dropwise at this temperature and the reaction was stirred for an additional 15 minutes. Triethylamine (25.5 mL) was then added dropwise and the reaction was allowed to warm to room temperature. 180 mL of water was added at room temperature and the layers were separated. The organic layer was washed once with water, dried over potassium carbonate, filtered, and concentrated under reduced vacuum to yield 7.83 g as a dark oil. This material was purified via silica gel chromatography employing the Water's Prep. 2000 and eluting with a solvent of methylene chloride/ethyl acetate 9:1 to provide the intermediate title compound (5.76 g, 73%) as a yellow oil. Ion Spray M.S. 204.1 (M*−1). Calculated for $C_8H_{15}NO_3S$: Theory: C, 46.81; H, 7.37; N, 6.82. Found: C, 46.56; H, 7.32; N, 6.77.

54
Preparation of [2-Hydroxy-2-(4-phenylphenyl)cyclopentyl][(methylethyl)sulfonyl]amine

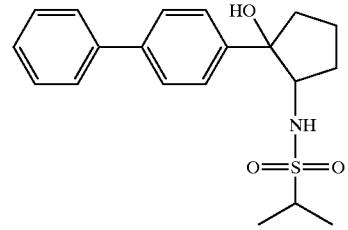

Scheme IA, step D: Into a flame dried 250 mL 3 neck flask that is fitted with a thermometer and condenser, are placed magnesium turnings (683 mg, 28.1 mmol) in anhydrous THF (15 mL). While stirring at room temperature under a nitrogen atmosphere, a small amount of 4-bromo-dibenzene is added dropwise along with one iodine crystal and dibromoethane (0.01 mL). This mixture is stirred vigorously and heated with a heat gun until the Grignard is initiated. The addition of 4-bromo-dibenzene is continued dropwise, keeping the temperature above 50° C. After the addition of 4-bromo-dibenzene (8.00 g, 30 mmol, total amount) is complete, the reaction is heated at reflux for 45 minutes to ensure complete Grignard formation. The reaction is allowed to cool to room temperature and 2-{[(methylethyl)sulfonyl]amino}cyclopentan-1-one (4.94 g, 24.1 mmol) is added dropwise. After addition is complete, the reaction is heated at reflux for an additional 2 hours and then stirred overnight at room temperature. In the morning, enough saturated ammonium chloride in water is added to precipitate salts nicely and the organic layer is decanted off. The remaining salts are washed two times with ether and the combined organic layers are concentrated under reduced vacuum. The resulting material is taken into ethyl acetate, washed once with water, dried over potassium carbonate, filtered, and concentrated under reduced vacuum. This isomeric mixture can be separated and purified via silica gel chromatography employing the Water's Prep 2000.

Additional Preparation of [2-Hydroxy-2-(4-phenylphenyl)cyclopentyl][(methylethyl)sulfonyl]amine Scheme IA, step D: Into a flame dried 250 mL 3 neck flask that was fitted with a thermometer and condenser, magnesium turnings (683 mg, 28.1 mmol) were placed in 15 mL anhydrous THF. While stirring at room temperature under a nitrogen atmosphere, a small amount of 4-bromo-dibenzene in THF (50 mL) was added dropwise along with one iodine crystal and 0.01 mL of dibromoethane. This mixture was stirred vigorously and heated with a heat gun until the Grignard was initiated as foaming was observed from metal turnings. The addition of 4-bromo-dibenzene was continued dropwise, keeping the temperature above 50° C. After the addition of 4-bromobiphenyl (8.00 g, 30 mmol), the reaction was heated at reflux for 45 minutes to insure complete Grignard formation. This reaction produced 60 mL of 0.032 M of di-bromobiphenyl magnesium bromide. The reaction was let cool to room temperature. Into a flame dried 100 mL 3 neck flask that was fitted with a thermometer and condenser, 2-{[(methylethyl)sulfonyl]amino}cyclopentan-1-one (500 mg, 2.44 mmol) in THF (35 mL) was added dropwise to 10 mL of the above synthesized Grignard. After addition, reaction was refluxed for 2 hours and then stirred overnight at room temperature. In the morning, enough saturated ammonium chloride in water was added to precipitate salts nicely and the organic layer was decanted off. The remaining salts were washed two times with ether and the combined organic layers were concentrated under reduced vacuum. The resulting material was taken into ethyl acetate, washed once with water, dried over potassium carbonate, filtered, and concentrated under reduced vacuum to yield 1.21 g of 2 spot material as a yellow solid. This isomeric mixture was separated and purified via silica gel chromatography employing the Water's Prep 2000 while eluting with a solvent of methylene chloride/ethyl acetate 9:1 to provide the intermediate title compound (130 mg, Cis) as a white solid (the top spot by TLC). FD M.S. 360.1 (M*).

Preparation of Final Title Compound

Scheme IA, step E: Into a 50 mL 3 neck flask fitted with a stirrer and thermometer, [2-hydroxy-2-(4-phenylphenyl)cyclopentyl][(methylethyl)sulfonyl]amine (35 mg, 0.1 mmol) in methylene chloride (5 mL) is added dropwise to 0.01 mL DAST (0.01 mL, excess) in methylene chloride (50 mL) while stirring at −78° C. under a nitrogen atmosphere. The reaction is allowed to warm to room temperature and diluted with methylene chloride (20 mL). This organic layer is washed with water, dried over sodium sulfate, filtered, and concentrated under reduced vacuum. The crude material is then purified via silica gel chromatography employing the Chromatotron® and using a 1000 micron rotor to provide the purified final title compound.

Additional Preparation of Final Title Compound

Scheme IA, step E: Into a 50 3 neck flask fitted with a stirrer and thermometer, [2-hydroxy-2-(4-phenylphenyl)cyclopentyl][(methylethyl)sulfonyl]amine (108 mg, 0.1 mmol) in $CH_2Cl_2$ (5 mL) was added dropwise to 0.1 mL DAST in $CH_2CL_2$ (15 mL) while stirring at −78° C. under a nitrogen atmosphere. The reaction was allowed to warm to room temperature and diluted with $CH_2Cl_2$ (20 mL). The organic layer was washed with $H_2O$, dried over $Na_2SO_4$, filtered, and concentrated under reduced vacuum to yield 117 mg as an oil. This two spot material was purified via silica gel chromatography employing the Chromatotron® and using a 2000 micron rotor while eluting with a solvent of methylene chloride to provide the final title compound (100 mg, quantitative yield) as an oil. Ion Spray M.S. 360.2 (M*−1). Calculated for $C_{20}H_{24}NO_2SF$: Theory: C, 66.46; H, 6.69; N, 3.88. Found: C, 66.76; H, 6.55; N, 4.02.

The compounds listed in Table 2 can be prepared by one of ordinary skill in the art from readily available reagents and starting materials in a manner analogous to the procedures disclosed herein. The compounds listed in Table 2 are preferred compounds in addition to those disclosed in the above examples.

TABLE 2

| Example | Compound Structure |
| --- | --- |
| 12 | 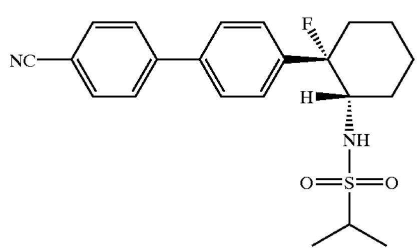 |
| 13 | 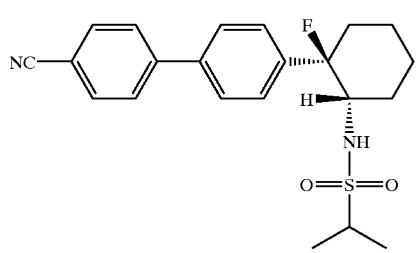 |
| 14 | 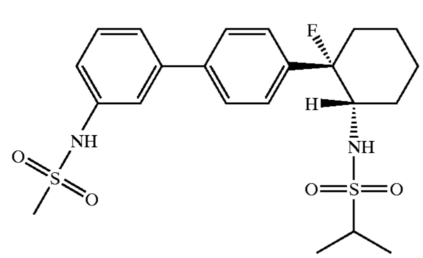 |

TABLE 2-continued

| Example | Compound Structure |
|---------|-------------------|
| 15 | 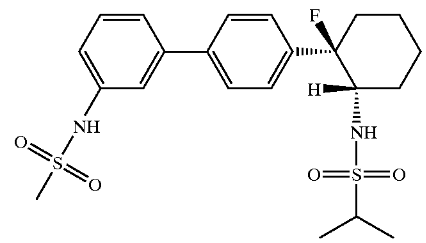 |
| 16 | 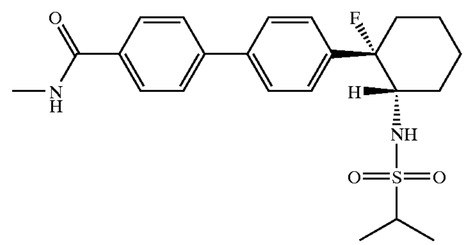 |
| 17 | 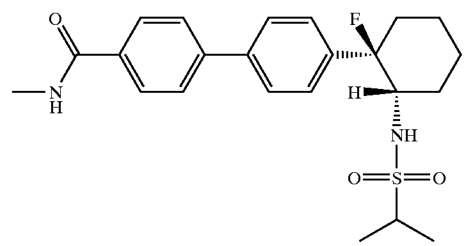 |
| 18 | 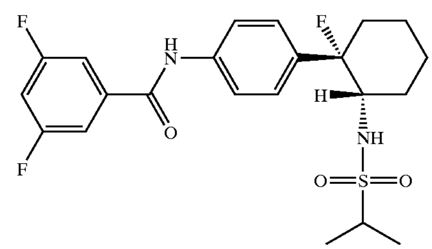 |
| 19 | 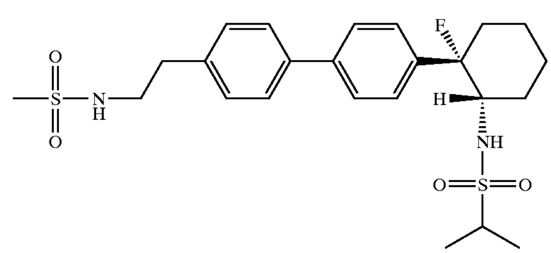 |
| 20 | 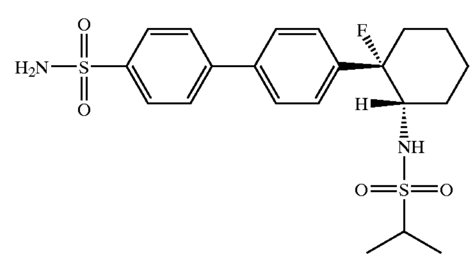 |

TABLE 2-continued

| Example | Compound Structure |
|---|---|
| 21 | 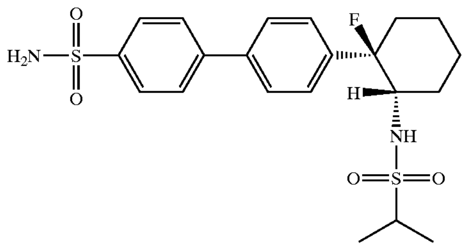 |
| 22 | 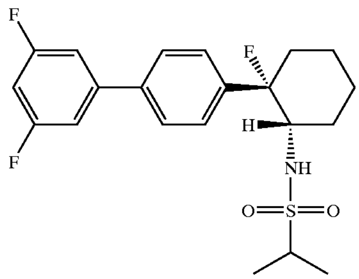 |
| 23 | 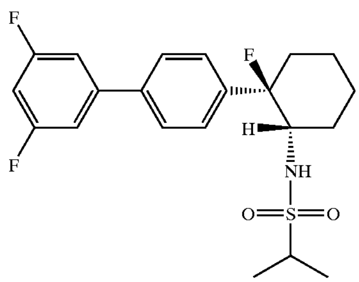 |
| 24 | 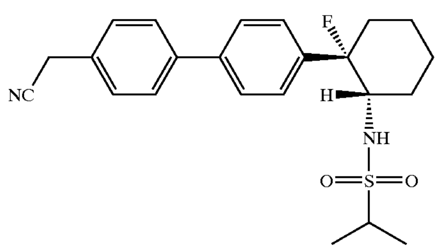 |
| 25 | 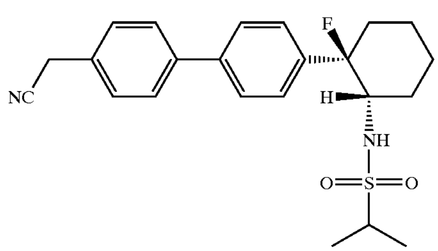 |
| 26 | 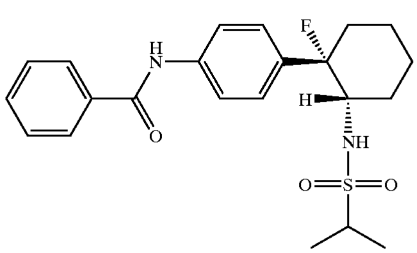 |

TABLE 2-continued

| Example | Compound Structure |
|---|---|
| 27 | 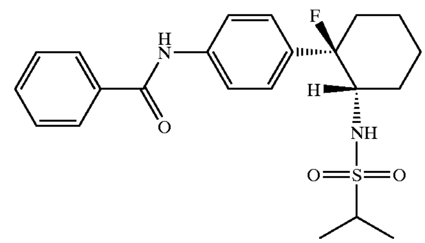 |
| 28 | 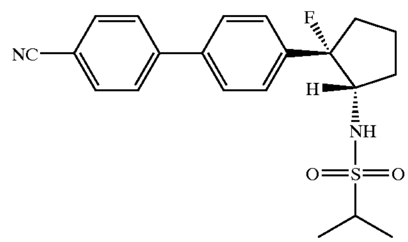 |
| 29 | 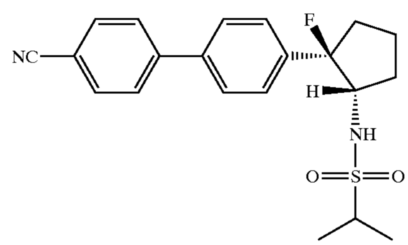 |
| 30 | 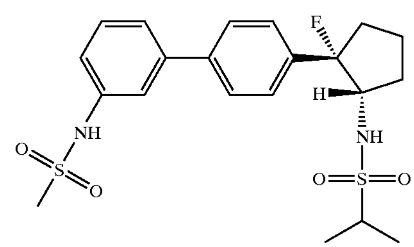 |
| 31 | 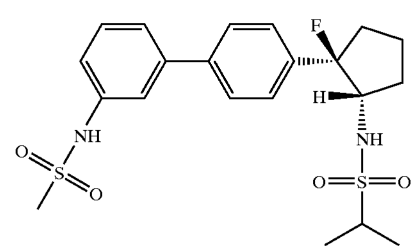 |
| 32 | 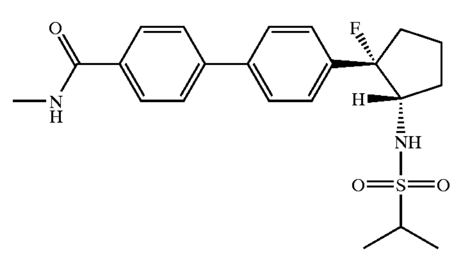 |

TABLE 2-continued

| Example | Compound Structure |
|---|---|
| 33 | 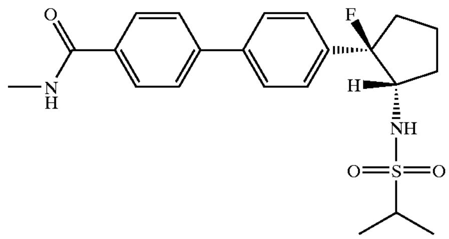 |
| 34 | 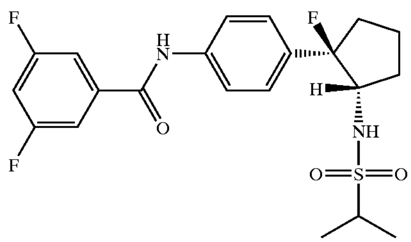 |
| 35 | 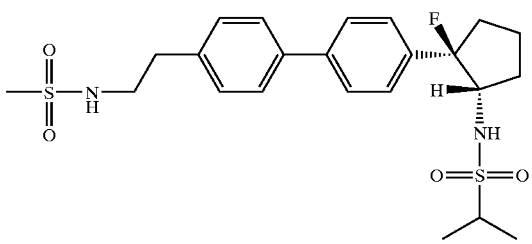 |
| 36 | 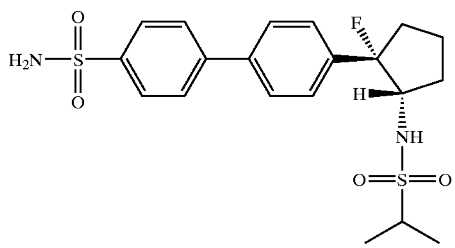 |
| 37 | 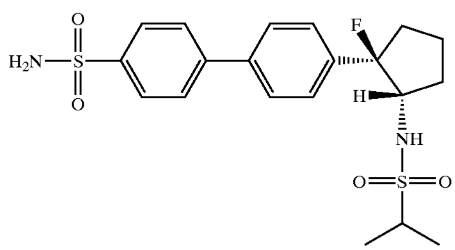 |
| 38 | 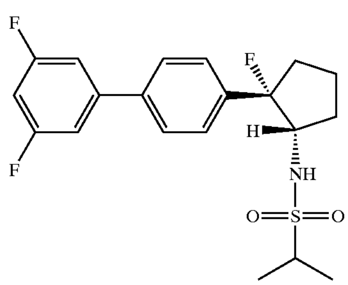 |

TABLE 2-continued

| Example | Compound Structure |
|---|---|
| 39 | 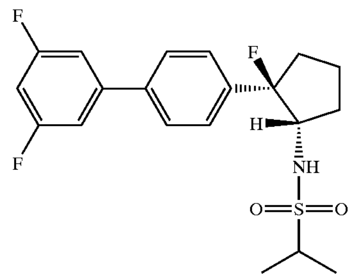 |
| 40 | 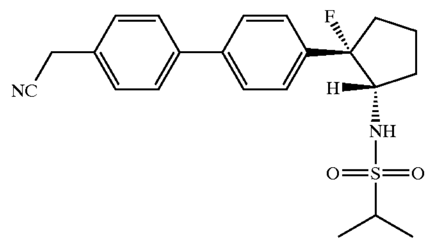 |
| 41 | 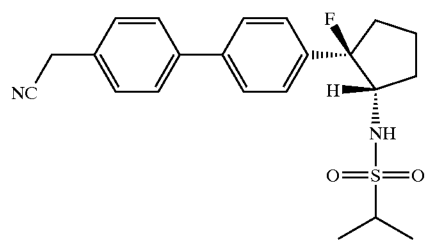 |
| 42 | 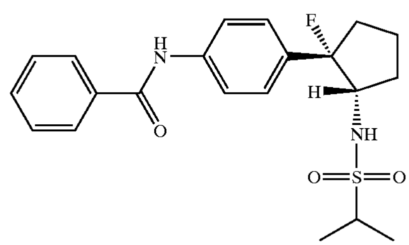 |
| 43 | 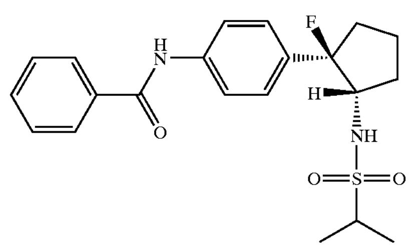 |

EXAMPLE 44

Preparation of [2-(4-Fluorophenyl)-2-hydroxycyclopentyl][(methylethyl)sulfonyl]amine

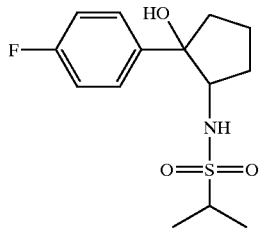

Scheme IA, step D: Into a flame dried 100 mL 3 neck flask that was fitted with a thermometer and condenser, 2-{[(methylethyl)sulfonyl]amino}cyclopentan-1-one (1.10 g, 5.36 mmol) in THF (25 mL) was added dropwise to 4-fluorophenylmagnesium bromide (3 mL, 2M solution in diethyl ether) while stirring at room temperature under a nitrogen atmosphere and keeping the temperature above 25° C. After the addition was complete, the reaction was refluxed for 2 hours and then stirred overnight at room temperature. In the morning, enough saturated ammonium chloride in water was added to precipitate the salts and the organic layer was decanted off. The remaining salts were washed two times with ether and the combined organic layers were concentrated under reduced vacuum. The resulting material was taken into ethyl acetate, washed once with water, dried over potassium carbonate, filtered, and concentrated under reduced vacuum to yield 930 mg of a dark oil. This isomeric mixture was purified via silica gel chromatography employing the Chromatotron® and using a 4000 micron rotor while eluting with a solvent of hexane/ethyl acetate 7:3 to provide the title compound (787 mg, 49%) as an oil. Ion Spray M.S. 300.1 (M*-1). Calculated for $C_{14}H_{20}NO_3SF—½H_2O$: Theory: C, 54.16; H, 6.82; N, 4.51. Found: C, 54.39; H, 6.61; N, 4.69.

EXAMPLE 45

Preparation of 2-Fluoro-2-(4-fluorophenyl)cyclopentyl][(methylethyl)sulfonyl]amine

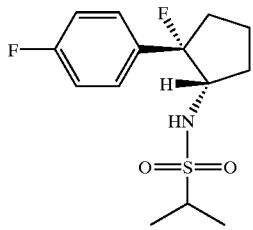

Scheme IA, step E: Into a 50 mL 3 neck flask fitted with a stirrer and thermometer, [2-(4-fluorophenyl)-2-hydroxycyclopentyl][(methylethyl)sulfonyl]amine (250 mg, 0.83 mmol) in $CH_2Cl_2$ (5 mL) was added dropwise to 0.1 mL DAST in $CH_2CL_2$ (10 mL) while stirring at −78° C. under a nitrogen atmosphere. The reaction was allowed to warm to room temperature and diluted with $CH_2Cl_2$ (20 mL). The organic layer was washed with $H_2O$, dried over $Na_2SO_4$, filtered, and concentrated under reduced vacuum to yield 196 mg as an orange oil. This two spot material was separated and purified via silica gel chromatography employing the Chromatotron® and using a 2000 micron rotor while eluting with a solvent of methylene chloride to provide the title compound (120 mg) as a viscous oil (top spot). Ion Spray M.S. 302.2 (M*-1). Calculated for $C_{14}H_{19}NO_3SF$: Theory: C, 55.42; H, 6.31; N, 4.61. Found: C, 55.58; H, 5.92; N, 4.56.

EXAMPLE 46

Preparation of Trans-{2-hydroxy-2-[4-(phenylmethoxy)phenyl]cyclopentyl}[(methylethyl)sulfonyl]amine and Cis-{2-hydroxy-2-[4-(phenylmethoxy)phenyl]cyclopentyl}[(methylethyl)sulfonyl]amine

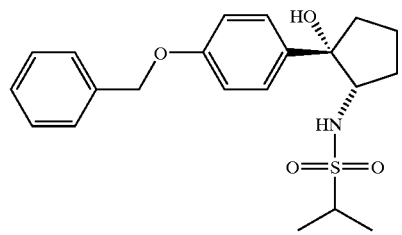

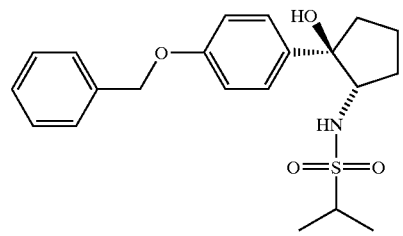

Into a flame dried 500 mL 3 neck flask that was fitted with a thermometer and condenser, magnesium turnings (899 mg, 38 mmol) were placed in anhydrous THF (15 mL). While stirring at room temperature under a nitrogen atmosphere, a small amount of 4-benzoxyphenyl bromide in THF (100 mL) was added dropwise along with one iodine crystal and 0.01 mL of dibromomethane. This mixture was stirred vigorously and heated with a heat gun until the Grignard was initiated as foaming was observed from metal turnings. The addition of 4-benzoxyphenyl bromide was continued dropwise, keeping the temperature above 50° C. After the addition of 4-benzoxyphenyl bromide (10.54 g, 40 mmol), the reaction was heated at reflux for 45 minutes to insure complete Grignard formation. The reaction was allowed to cool to room temperature. 2-{[(Methylethyl)sulfonyl]amino}cyclopentan-1-one (5.70 g, 27.8 mmol) in THF (35 mL) was added dropwise. After addition was complete, the reaction was heated at reflux for 2 hours and then stirred overnight at room temperature. Enough saturated ammonium chloride in water was then added to precipitate salts and the organic layer was decanted off. The remaining salts were washed two times with ether and the combined organic layers were concentrated under reduced vacuum. The resulting material was taken into ethyl acetate, washed once with water, dried over potassium carbonate, filtered, and concentrated under reduced vacuum to yield 11.51 g of a 2 spot material (TLC) as a dark oil. This isomeric mixture was separated and purified via silica gel chromatography employing the Water's Prep 2000 while eluting with a gradient solvent of methylene chloride/ethyl acetate 19:1 to methylene chloride/ethyl acetate 9:1 to provide the trans isomer of title compound (1.35 g) as an oil (top spot). Ion Spray M.S. 388.2 (M*−1). Continued elution afforded 250 mg of a mixture as an oil. Ion Spray M.S. 388.2 (M*−1). Final elution afforded the cis isomer of the title compound (200 mg) as a slowly crystallizing oil (bottom spot). Ion Spray M.S. 388.2 (M*−1). Calculated for $C_{21}H_{27}NO_4S$: Theory: C, 64.76; H, 6.99; N, 3.60. Found: C, 64.77; H, 6.91; N, 3.56.

EXAMPLE 47

Preparation of [2-Hydroxy-2-(4-hydroxyphenyl)cyclopentyl][(methylethyl)sulfonyl]amine

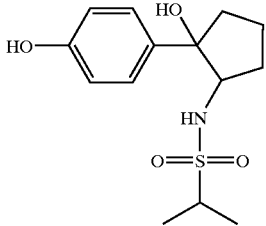

Cis/trans-{2-Hydroxy-2-[4-(phenylmethoxy)phenyl]cyclopentyl}[(methylethyl)sulfonyl]amine (1.44 mg, 3.70 mmol, prepared in example 46) was combined with 5% palladium on carbon (1.70 mg) in ethyl acetate (150 mL) and placed on the power shaker under a hydrogen atmosphere at 45 psi's for 4 hours. The solution was filtered over a Celite® mat and the resulting filtrate was concentrated under reduced vacuum to yield 1.2 g as a white foam. This material was purified via silica gel chromatography employing the Chromatotron® using a 4000 micron rotor while eluting with a gradient solvent of methylene chloride/methanol 9:1 to methylene chloride/methanol 1:1 to provide the title compound (710 mg, 65%) as a white foam. Yield=65%. Ion Spray M.S. 298.2 (M*−1). Calculated for $C_{14}H_{21}NO_4S$: Theory: C, 56.17; H, 7.07; N, 4.68. Found: C, 55.94; H, 6.98; N, 4.51.

EXAMPLE 48

Preparation of Trans-(2-{4-[(3,5-difluorophenyl)methoxy]phenyl}-2-hydroxycyclopentyl)[(methylethyl)sulfonyl]amine and Cis-(2-{4-[(3,5-difluorophenyl)methoxy]phenyl}-2-hydroxycyclopentyl)[(methylethyl)sulfonyl]amine

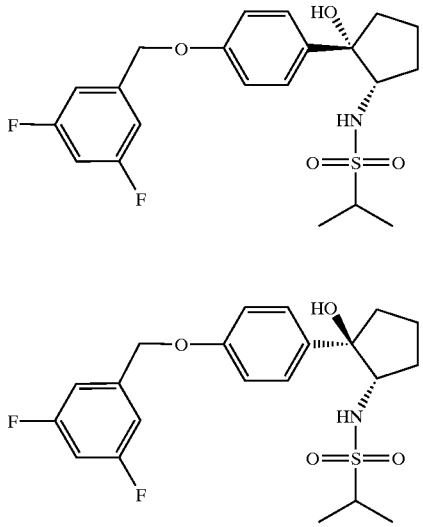

[2-Hydroxy-2-(4-hydroxyphenyl)cyclopentyl][(methylethyl)sulfonyl]amine (200 mg, 0.67 mmol), 3,5-difluorobenzyl bromide (153 mg, 1.1 eq) and potassium carbonate (111 mg, 1.2 eq) were combined in acetone (20 mL) and stirred overnight at room temperature under a nitrogen atmosphere. The solution was then filtered and the filtrate was concentrated under reduced vacuum to yield 339 mg as an oil. This two spot material (TLC) was separated and purified via silica gel chromatography employing the Chromatotron® and using a 4000 micron rotor while eluting with a solvent of methylene chloride/ethyl acetate 9:1 to yield isomer #1 (17 mg) as a white foam (top spot). Fd M.S. 425.2 (M*). Continued elution afforded 203 mg of a mixture as an oil. Fd M.S. 425.2 (M*). Calculated for $C_{21}H_{25}NO_4SF_2 \cdot \tfrac{1}{2}H_2O$: Theory: C, 58.05; H, 6.03; N, 3.22. Found: C, 58.23; H, 5.80; N, 3.07. Final elution afforded isomer #2 (200 mg) as an oil (bottom spot). Fd M.S. 425.2 (M*).

EXAMPLE 49

Preparation of [2-Hydroxy-2-(4-phenoxyphenyl)cyclopentyl][(methylethyl)sulfonyl]amine

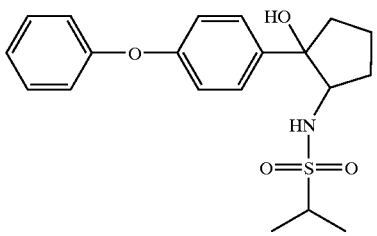

Into a flame dried 250 mL 3 neck flask that was fitted with a thermometer and condenser, and while stirring at room temperature under a nitrogen atmosphere, 2-{[(methylethyl)sulfonyl]amino}cyclopentan-1-one (1.00 g, 4.9 mmol) in THF (40 mL) was added dropwise to 15 mL of 0.5 M 4-phenoxyphenylmagnesium bromide. The addition of 2-{[(methylethyl)sulfonyl]amino}cyclopentan-1-one was continued dropwise, keeping the temperature above 35° C. After the addition of 2-{[(methylethyl)sulfonyl]amino}cyclopentan-1-one was complete, the reaction was stirred overnight at room temperature. Enough saturated ammonium chloride in water was then added to precipitate salts and the organic layer was decanted off. The remaining salts were washed two times with ether and the combined organic layers were concentrated under reduced vacuum. The resulting semi-solid was taken into ethyl acetate, washed once with water, dried over potassium carbonate, filtered, and concentrated under reduced vacuum to yield 2.14 g of as a dark oil. This material was purified via silica gel chromatography employing the Water's Prep. 2000 while eluting with a solvent of hexane/ethyl acetate 7:3 to provide the title compound (540 mg) as a white solid. Ion spray M.S. 374.1 (M*-1). Calculated for $C_{20}H_{25}NO_4S$: Theory: C, 63.98; H, 6.71; N, 3.73. Found: C, 63.70; H, 6.77; N, 3.55.

EXAMPLE 50

Preparation of Trans-[2-fluoro-2-(4-phenoxyphenyl)cyclopentyl][(methylethyl)sulfonyl]amine and Cis-[2-fluoro-2-(4-phenoxyphenyl)cyclopentyl][(methylethyl)sulfonyl]amine

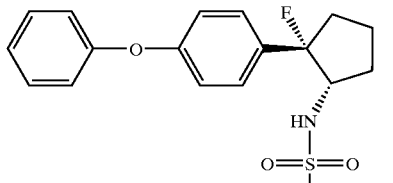

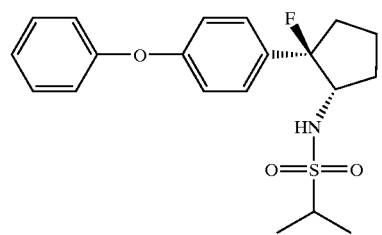

Into a 50 mL 3 neck flask fitted with a stirrer and thermometer [2-hydroxy-2-(4-phenoxyphenyl)cyclopentyl][(methylethyl)sulfonyl]amine (500 mg, 1.30 mmol) in $CH_2Cl_2$ (5 mL) was added dropwise to 0.1 mL DAST in $CH_2CL_2$ (15 mL) while stirring at −78° C. under a nitrogen atmosphere. The reaction was allowed to warm to room temperature and diluted with $CH_2Cl_2$ (20 mL). This organic layer was washed with $H_2O$, dried over $Na_2SO_4$, filtered, and concentrated under reduced vacuum to yield 490 mg of a 2 spot material (TLC) as an oil. This material was separated and purified via silica gel chromatography employing the Chromatotron® and using a 4000 micron rotor while eluting with a solvent of hexane/ethyl acetate 7:3 to provide the trans isomer of the title compound (97 mg) as a solid (top spot). Ion spray M.S. 376.4 (M*-1) Calculated for $C_{20}H_{24}NO_3SF$: Theory: C, 63.64; H, 6.41; N, 3.71. Found: C, 63.82; H, 6.36; N, 3.66. Continued elution afforded 271 mg of the 2 spot mixture as a semi-solid. Fd M.S. 376.4 (M*-1). Final elution afforded the cis isomer of the title compound (31 mg) as an oil (bottom spot). Ion spray M.S. 376.4 (M*-1).

EXAMPLE 51

Preparation of [2-Hydroxy-2-(4-{2-[(methysulfonyl)amino]ethoxy}phenyl)cyclopentyl][(methylethyl)sulfonyl]amine

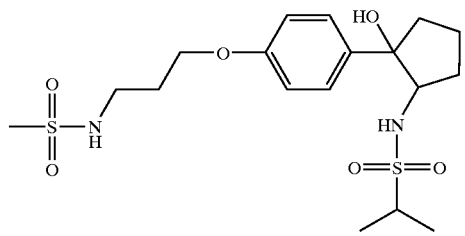

Preparation of 2-[4-(1-Hydroxy-2-{[(methylethyl)sulfonyl]amino}cyclopentyl)phenoxy]ethanenitrile

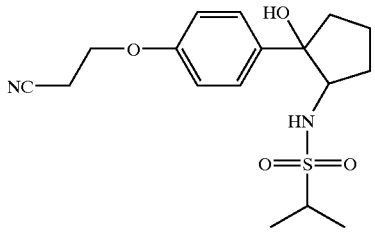

[2-Hydroxy-2-(4-hydroxyphenyl)cyclopentyl][(methylethyl)sulfonyl]amine (650 mg, 2.17 mmol, prepared in example 47), bromoacetonitrile (292 mg, 1.1 eq), and potassium carbonate (360 mg, 1.2 eq) were combined with acetone (40 mL) and stirred overnight at room temperature under a nitrogen atmosphere. The solution was then filtered and the filtrate was concentrated under reduced vacuum to yield 694 mg as an oil. This two spot material was separated and purified via silica gel chromatography employing the Chromatotron® and using a 4000 micron rotor while eluting with a solvent of methylene chloride/ethyl acetate 9:1 to yield the intermediate title compound (390 mg, 54%) as a white foam (top spot by TLC). Ion Spray M.S. 337.2 (M*-1) Calculated for $C_{16}H_{22}N_2O_4S$: Theory: C, 56.79; H, 6.55; N, 8.28. Found: C, 56.51; H, 6.46; N, 8.24.

Preparation of {2-[4-(2-Aminoethoxy)phenyl]-2-hydroxycyclopentyl}[(methylethyl)sulfonyl]amine

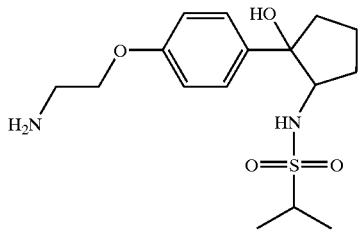

Into a 50 mL 3 neck flask with stirrer, borane-THF complex (2 mL, 1M solution) was added syringe wise to 2-[4-(1-hydroxy-2-{[(methylethyl)sulfonyl]amino}cyclopentyl)phenoxy]ethanenitrile (125 mg, 0.37 mmol) in THF (10 mL) while stirring at room temperature under a nitrogen atmosphere. The reaction mixture was then stirred overnight. 3 mL of 1:1 THF/Methanol solution was then added by syringe with severe foaming. After the foaming subsided, the solution was concentrated under reduced vacuum to yield 85 mg as an oil. This material was purified via silica gel chromatography employing the Chromatotron® and using a 2000 micron rotor while eluting with a solvent of methylene chloride/ethyl acetate 9:1 to yield the intermediate title compound (35 mg) as an oil. Ion spray M.S. 341.4 (M*−1).

Alternative Preparation

Into a 100 mL, 3 neck flask with stirrer 2-[4-(1-hydroxy-2-{[(methylethyl)sulfonyl]amino}cyclopentyl)phenoxy]ethanenitrile (125 mg, 0.37 mmol) in toluene (10 mL) is added dropwise to Red-Al (3 mL, 65% solution in toluene) while stirring at room temperature under a nitrogen atmosphere. The reaction mixture is then stirred for two hours at this temperature. The mixture is poured into water and the desired material is extracted with ethyl acetate. The organic layer is washed once with water, dried over potassium carbonate, filtered, and concentrated under reduced vacuum to yield the crude product. This material is purified by silica gel chromatography with elution of a suitable solvent such as hexane/ethyl acetate to provide the pure desired material.

Preparation of Final Title Compound

In a 100 mL 3 neck flask fitted with a stirrer and thermometer, methanesulfonyl chloride (95 mg, 1.2 eq) is added dropwise to {2-[4-(2-aminoethoxy)phenyl]-2-hydroxycyclopentyl}[(methylethyl)sulfonyl]amine (230 mg, 0.67 mmol) and DBU (153 mg, 1.5 eq) in CH$_2$Cl$_2$ (40 mL) while stirring at 0° C. under a nitrogen atmosphere. The reaction is allowed to warm to room temperature and stirred overnight at this temperature. The reaction is then diluted with CH$_2$Cl$_2$ (50 mL) and the organic layer is washed two times with H$_2$O, dried over Na$_2$SO$_4$, filtered, and concentrated under reduced vacuum to yield the product. This material is then purified via silica gel chromatography employing the Chromatotron® and using 2000 micron rotor while eluting with a suitable eluent, such as hexane/ethyl acetate to provide the final title compound.

EXAMPLE 52

Preparation of {2-Hydroxy-2-[4-(2-{[(methylethyl)sulfonyl]amino}ethoxy)phenyl]cyclopentyl}[(methylethyl)sulfonyl]amine

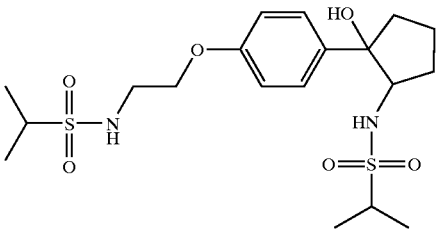

The title compound is prepared in a manner analogous to the procedure set forth in example 51 from 2-propanesulfonyl chloride and {2-[4-(2-aminoethoxy)phenyl]-2-hydroxycyclopentyl}[(methylethyl)sulfonyl]amine.

EXAMPLE 53

Preparation of N-{2-[4-(1-Hydroxy-2-{[(methylethyl)sulfonyl]amino}cyclopentyl)phenoxy]ethyl}acetamide

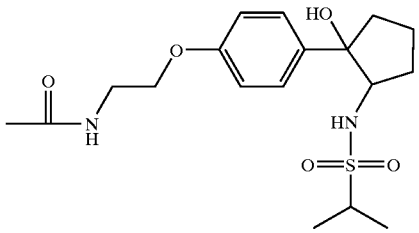

In a 100 mL 3 neck flask fitted with a stirrer and thermometer, acetyl chloride (63 mg, 1.2 eq) is added dropwise to {2-[4-(2-aminoethoxy)phenyl]-2-hydroxycyclopentyl}[(methylethyl)sulfonyl]amine (230 mg, 0.67 mmol) and triethylamine (102 mg, 1.5 eq) in CH$_2$Cl$_2$ (40 mL) while stirring at 0° C. under a nitrogen atmosphere. The reaction is allowed to warm to room temperature and stirred for 2 hours. The reaction is then diluted with CH$_2$Cl$_2$ (50 mL) and the organic layer is washed two times with H$_2$O, dried over Na$_2$SO$_4$, filtered, and concentrated under reduced vacuum to yield the product. This material is purified via silica gel chromatography employing the Chromatotron® and using 2000 micron rotor while eluting with a suitable eluent, such as hexanes/ethyl acetate to provide the title compound.

EXAMPLE 54

Preparation of [2-Fluoro-2-(4-{2-[(methylsulfonyl)amino]ethoxy}phenyl)cyclopentyl][(methylethyl)sulfonyl]amine

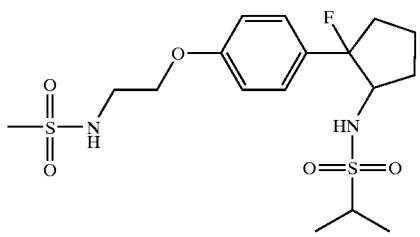

Into a 50 mL 3 neck flask fitted with a stirrer and thermometer, [2-hydroxy-2-(4-{2-[(methylsulfonyl)amino]ethoxy}phenyl)cyclopentyl][(methylethyl)sulfonyl]amine (150 mg, 0.36 mmol) in $CH_2Cl_2$ (5 mL) is added dropwise to 0.01 mL DAST in $CH_2CL_2$ (15 mL) while stirring at $-78°$ C. under a nitrogen atmosphere. The reaction is allowed to warm to room temperature and diluted with $CH_2Cl_2$ (20 mL). This organic layer is washed with $H_2O$, dried over $Na_2SO_4$, filtered, and concentrated under reduced vacuum to yield the product. This material is purified via silica gel chromatography employing the Chromatotron® and using 2000 micron rotor while eluting with a suitable eluent, such as hexanes/ethyl acetate to provide the final title compound.

EXAMPLE 55

Preparation of {2-Fluoro-2-[4-(2-{[(methylethyl)sulfonyl]amino}ethoxy)phenyl]cyclopentyl}[(methylethyl)sulfonyl]amine

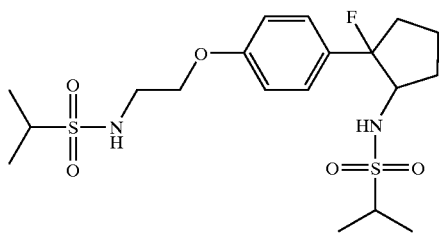

The title compound is prepared in a manner analogous to the procedure set forth in example 54 from {2-hydroxy-2-[4-(2-{[(methylethyl)sulfonyl]amino}ethoxy)phenyl]cyclopentyl}[(methylethyl)sulfonyl]amine.

EXAMPLE 56

Preparation of N-{2-[4-(1-Fluoro-2-{[(methylethyl)sulfonyl]amino}cyclopentyl)phenoxy]ethyl}acetamide

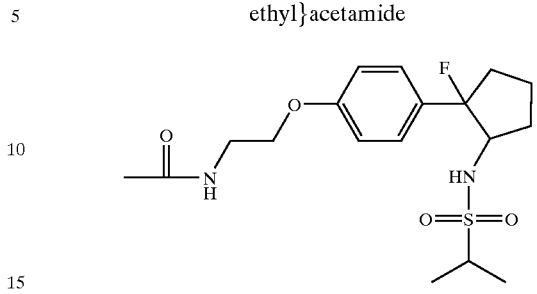

The title compound is prepared in a manner analogous to the procedure set forth in example 54 from N-{2-[4-(1-hydroxy-2-{[(methylethyl)sulfonyl]amino}cyclopentyl)phenoxy]ethyl}acetamide.

EXAMPLE 57

Preparation of 2-[4-(1-Fluoro-2-{[(methylethyl)sulfonyl]amino}cyclopentyl)phenoxy]ethanenitrile

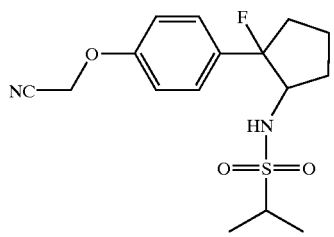

The title compound was prepared in a manner analogous to the procedure set forth in example 54 from 2-[4-(1-hydroxy-2-{[(methylethyl)sulfonyl]amino}cyclopentyl)phenoxy]ethanenitrile (90 mg, 0.27 mmol) and DAST (0.01 mL) to yield the title compound (95 mg) as an oil. This material was purified by silica gel chromatography employing the Chromatotron® and using a 1000 micron rotor while eluting with a solvent methylene chloride/ethyl acetate 19:1 to yield the title compound (80 mg, 87%) as an oil. Ion Spray M.S. 339.1 (M*–1) Calculated for $C_{16}H_{21}N_2O_3SF$: Theory: C, 56.45; H, 6.22; N, 8.23. Found: C, 56.18; H, 6.06; N, 8.13.

EXAMPLE 58

Preparation of [2-(4-Fluorophenyl)-2-hydroxycyclohexyl][(methylethyl)sulfonyl]amine

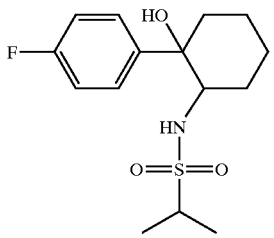

Preparation of [(methylethyl)sulfonyl][2-(phenylmethoxy)cyclohexyl]amine

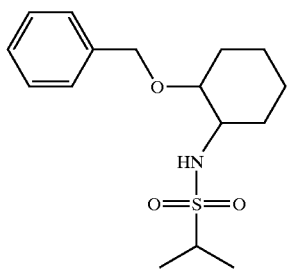

In a 500 mL 3 neck flask fitted with a stirrer and thermometer, 2-propanesulfonyl chloride (7.61 g, 1.1 eq) was added dropwise to (1S,2S)-benzoxycyclohexylamine (10.0 g, 0.05 mol) and DBU (8.89 g, 1.2 eq) in $CH_2Cl_2$ (200 mL) while stirring at 0° C. under a nitrogen atmosphere. The reaction was allowed to warm to room temperature and stirred overnight at this temperature. In the morning, reaction was diluted with $CH_2Cl_2$ (200 mL) and the organic layer was washed two times with $H_2O$, dried over $Na_2SO_4$, filtered, and concentrated under reduced vacuum to yield 15.0 g as a viscous oil. This material was purified via silica gel chromatography employing the Water's Prep. 2000 and eluting with a solvent of methylene chloride to yield the intermediate title compound (12.46 g, 80%) as a slowly crystallizing oil. (FD) M.S. 311.3 (M*).

Preparation of (2-hydroxycyclohexyl)[(methylethyl)sulfonyl]amine

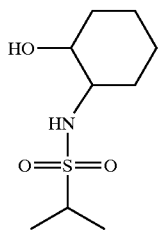

[(Methylethyl)sulfonyl][2-(phenylmethoxy)cyclohexyl]amine (11.41 g, 36.6 mmol) and 10% palladium on carbon (1.40 g) were combined in ethanol (300 mL) and placed on the power shaker under a hydrogen atmosphere at 60 psi's overnight. The solution was then filtered over a Celite® mat and the resulting filtrate was concentrated under reduced vacuum to yield the intermediate title compound (6.78 g, 84%) as a white solid. Ion Spray M.S. 222.1 (M*+1). Calculated for $C_9H_{19}NO_3S$: Theory: C 48.84, H 8.65, N 6.32. Found: C 49.10, H 8.84, N 6.42.

Preparation of 2-{[(methylethyl)sulfonyl]amino}cyclohexan-1-one

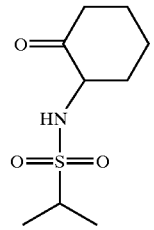

Into a 500 mL single neck flask (2-hydroxycyclohexy)[(methylethyl)sulfonyl]amine (6.78 g, 30.6 mmol) was combined with pyridinium chlorochromate (7.92 g, 1.2 eq) in methylene chloride (300 mL) and stirred at room temperature under a nitrogen atmosphere for 4 hours. The solution was then filtered over a Celite® mat and the organic layer was washed once with water, dried over potassium carbonate, filtered, and concentrated under reduced vacuum to yield 13.42 g as a dark oil. This material was purified via silica gel chromatography employing the Water's Prep. 2000 and eluting with a solvent of methylene chloride/ethyl acetate 19:1 to yield the intermediate title compound (3.95 g, 59%). as a white solid. Ion Spray M.S. 218 (M*-1). Calculated for $C_9H_{17}NO_3S$: Theory: C 49.29, H 7.81, N 6.39. Found: C 49.25, H 7.58, N 6.32.

Alternative preparation of 2-{[(methylethyl)sulfonyl]amino}cyclohexan-1one

Into a flame dried 250 mL 3 neck flask fitted with a thermometer and magnetic stirrer, DMSO (2.61 mL) in methylene chloride (10 mL) was added dropwise to oxalyl chloride (1.60 mL) in methylene chloride (50 mL) while stirring at −55° C. under a nitrogen atmosphere. After 2 minutes, (2-hydroxycyclohexyl)[(methylethyl)sulfonyl]amine (3.60 g, 16.3 mmol) in methylene chloride (10 mL) was added dropwise at this temperature and the reaction was stirred for an additional 15 minutes. Triethylamine (10.8 mL) was then added dropwise and the reaction was allowed to warm to room temperature. Water (76 mL) was added at room temperature and the layers were separated. The organic layer was washed once with water, dried over potassium carbonate filtered, and concentrated under reduced vacuum to yield 3.90 g as an orange solid. This material was purified via silica gel chromatography employing the Water's Prep. 2000 and eluting with a solvent of methylene chloride/ethyl acetate 19:1 to yield the intermediate title compound (2.94 g, 82%) as a white solid. FD M.S. 219.2 (M*). Calculated for $C_9H_{17}NO_3S$: Theory: C 49.29, H 7.81, N 6.39. Found: C 49.18, H 7.84, N 6.39.

Preparation of Final Title Compound

Into a flame dried 100 mL 3 neck flask that was fitted with a thermometer and condenser, and while stirring at room temperature under a nitrogen atmosphere, 2-{[(methylethyl)sulfonyl]amino}cyclohexan-1-one (1.18 g, 13.2 mmol) in THF (25 mL) was added dropwise to 4-fluorophenylmagnesium bromide (3 mL, 17.5 mmol, 2 M solution). The addition of 2-{[(methylethyl)sulfonyl]amino}cyclohexan-1-one was continued dropwise, keeping the temperature above 35 C. After the addition of 2-{[(methylethyl)sulfonyl]amino}cyclohexan-1-one, the reaction was stirred overnight at room temperature. Enough saturated ammonium chloride in water was then added to precipitate salts and the organic layer was decanted off. The remaining salts were washed two times with ether and the combined organic layers were concentrated under reduced vacuum. The resulting semi-solid was taken into ethyl acetate, washed once with water, dried over potassium carbonate, filtered, and concentrated under reduced vacuum to yield 1.30 g as a semi-solid. This material was purified via silica gel chromatography employing the Chromatotron® while using a 4000 micron rotor and eluting with a gradient solvent of methylene chloride to methylene chloride/ethyl acetate 9:1 to yield the final title compound (430 mg, 25%) as a slowly crystallizng oil. Ion Spray M.S. 314.0 (M*−1). Calculated for $C_{15}H_{22}NO_3SF \cdot \frac{1}{2}H_2O$: Theory: C 55.52, H7.14, N 4.32. Found: C 55.78, H 6.88, N 4.45.

EXAMPLE 59

Preparation of trans-[2-fluoro-2-(4-fluorophenyl) cyclohexyl][(methylethyl)sulfonyl]amine and cis-[2-fluoro-2-(4-fluorophenyl)cyclohexyl][(methylethyl) sulfonyl]amine

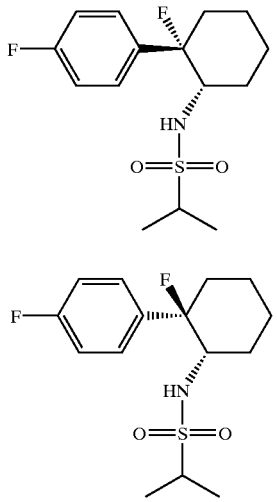

Into a 50 mL 3 neck flask fitted with a stirrer and thermometer, [2-(4-fluorophenyl)-2-hydroxycyclohexyl] [(methylethyl)sulfonyl]amine (200 mg, 0.63 mmol) in $CH_2Cl_2$ (5 mL) was added dropwise to 0.1 mL DAST in $CH_2CL_2$ (15 mL) while stirring at −78° C. under a nitrogen atmosphere. The reaction was allowed to warm to room temperature and diluted with $CH_2Cl_2$ (20 mL). This organic layer was washed with $H_2$ O, dried over $Na_2SO_4$, filtered, and concentrated under reduced vacuum to yield 220 mg of a 2 spot material (by TLC) as an oil. This material was separated and purified via silica gel chromatography employing the Chromoatotron® and using a 4000 micron rotor while eluting with a solvent of methylene chloride/ ethyl acetate 19:1 to yield the trans title compound (80 mg) as a white foam (top spot by TLC). Ion spray M.S. 316.1 (M*−1). Calculated for $C_{15}H_{21}NO_2SF_2$: Theory: C 56.76, H6.71, N 4.41. Found: C 56.43, H 6.69, N 4.21. Continued elution afforded 62 mg of the 2 spot mixture as an oil. Fd M.S. 316.1 (M*−1). Calculated for $C_{15}H_{21}NO_2SF_2$: Theory: C 56.76, H 6.71, N 4.41. Found: C 57.46, H 7.09, N 4.35. Final elution afforded the cis title compound (26 mg) as a white solid (bottom spot by TLC). Ion spray M.S. 316.1 (M*−1). Calculated for $C_{15}H_{21}NO_2SF_2$: Theory: C 56.76, H 6.71, N 4.41. Found: C 56.60, H 6.89, N 4.35.

EXAMPLE 60

Preparation of cis-[2-hydroxy-2-(4-methoxyphenyl) cyclohexyl][(methylethyl)sulfonyl]amine and trans-[2-hydroxy-2-(4-methoxyphenyl)cyclohexyl] [(methylethyl)sulfonyl]amine

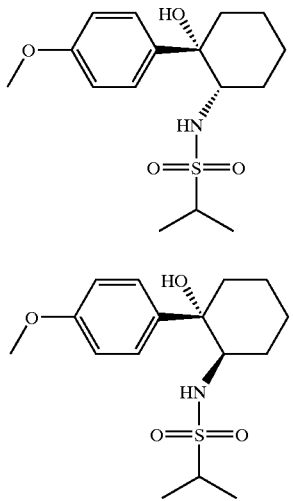

Into a frame dried 250 mL 3 neck flask that was fitted with a thermometer and condenser, and while stirring at room temperature under a nitrogen atmosphere, 2-{[(methylethyl) sulfonyl]amino}cyclohexan-1-one (2.90 g, 13.2 mmol) in THF (50 mL) was added dropwise to 4-methoxyphenylmagnesium bromide (35 mL, 17.5 mmol, 0.5 M solution). The addition of 2-{[(methylethyl)sulfonyl] amino}cyclohexan-1-one was continued dropwise, keeping the temperature above 35° C. After the addition of 2-{ [(methylethyl)sulfonyl]amino}cyclohexan-1-one, the reaction was stirred overnight at room temperature. Enough saturated ammonium chloride in water was added to precipitate salts and the organic layer was decanted off. The remaining salts were washed two times with ether and the combined organic layers were concentrated under reduced vacuum. The resulting semi-solid was taken into ethyl acetate, washed once with water, dried over potassium carbonate and concentrated under reduced vacuum to yield 3.02 g as a dark semi-solid. This material was purified via silica gel chromatography employing the Water's Prep 2000 and eluting with a gradient solvent of methylene chloride/ ethyl acetate 19:1 to methylene chloride/ethyl acetate 9:1 to yield a mixture of the cis and trans isomers of the title compound (1.03 g) as a white solid Ion Spray M.S. 326.1 (M*−1). Calculated for $C_{16}H_{25}NO_4S \cdot \frac{1}{2}H_2O$: Theory: C 57.11, H7.74, N 4.16. Found: C 57.69, H 7.49, N 3.76.

This isomeric two spot material (400 mg) was further separated via silica gel chromatography using the Chromatotron® and employing a 4000 micron plate and eluting with a solvent of hexane/ethyl acetate 7:3 to yield the title compound (40 mg) as a white solid (top spot by TLC, cis isomer). Ion Spray M.S. 326.1 (M*−1).

Continued elution afforded the title compound (10 mg) as a white solid (bottom spot by TLC, trans isomer). Ion Spray M.S. 326.1 (M*−1)

EXAMPLE 61

Preparation of trans-{2-hydroxy-2-[4-(phenylmethoxy)phenyl]cyclohexyl}[(methylethyl)sulfonyl]amine and cis-{2-hydroxy-2-[4-(phenylmethoxy)phenyl]cyclohexyl}[(methylethyl)sulfonyl]amine

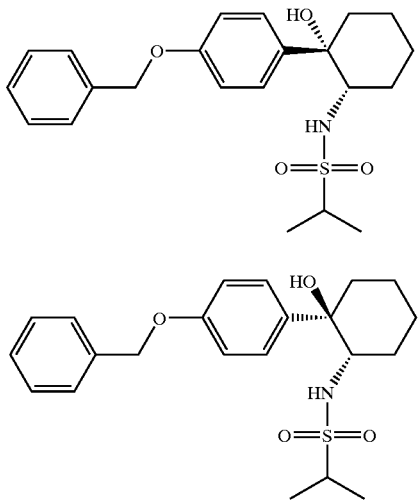

Into a flame dried 250 mL 3 neck flask that was fitted with a thermometer and condenser, magnesium turnings (370 mg, 15.2 mmol) was placed in 10 mL anhydrous THF. While stirring at room temperature under a nitrogen atmosphere, a small amount of 4-benzoxyphenyl bromide was added dropwise along with one iodine crystal and 0.01 mL of dibromoethane. This mixture was stirred vigorously and heated with a heat gun. Grignard was initiated as foaming was observed from metal turnings. The addition of 4-benzoxyphenyl bromide was continued dropwise, keeping the temperature above 50° C. After the addition of 4-benzoxyphenyl bromide (4.00 g, 15.2 mmol), the reaction was heated at reflux for 45 minutes to insure complete Grignard formation. The reaction was allowed to cool to room temperature, and 2-{[(methylethyl)sulfonyl]amino}cyclohexan-1-one (1.50 g, 6.84 mmol) in THF (50 mL) was added dropwise. After addition, the reaction was refluxed for an additional 2 hours and then stirred overnight at room temperature. Enough saturated ammonium chloride in water was then added to precipitate salts and the organic layer was decanted off. The remaining salts were washed two times with ether and the combined organic layers were concentrated under reduced vacuum. The resulting semi-solid was taken into ethyl acetate, washed once with water, dried over potassium carbonate, filtered, and concentrated under reduced vacuum to yield 4.73 g as a dark oil. This material was purified via silica gel chromatography employing the Water's Prep 2000 and eluting with a gradient solvent of hexane/ethyl acetate 4:1 to hexane/ethyl acetate 1:1 to provide a cis/trans mixture of the title compound (1.21 g) as an oil. Ion Spray M.S. 402.1 (M*−1). This isomeric 2 spot material (1 g) was separated via silica gel chromatography employing the Water's Prep 2000 and eluting with a gradient solvent of hexane/ethyl acetate 4:1 to hexane/ethyl acetate 1:1 to provide the cis isomer of the title compound (130 mg, top spot by TLC) as a slowly crystallizing oil. Ion Spray M.S. 402.1 (M*−1). Calculated for $C_{22}H_{29}NO_4S \cdot \frac{1}{2}H_2O$: Theory: C 64.00, H 7.33, N 3.40. Found: C 64.26, H 6.93, N 2.91.

Further elution yielded the trans isomer of the title compound (70 mg, bottom spot by TLC) as a slowly crystallizing oil. Ion Spray M.S. 402.1 (M*−1). Calculated for $C_{22}H_{29}NO_4S$: Theory: C 65.48, H 7.24, N 3.47. Found: C 64.84, H 6.99, N 2.90.

EXAMPLE 62

Preparation of trans-[2-hydroxy-2-(4-phenoxyphenyl)cyclohexyl][(methylethyl)sulfonyl]amine and cis-[2-hydroxy-2-(4-phenoxyphenyl)cyclohexyl][(methylethyl)sulfonyl]amine

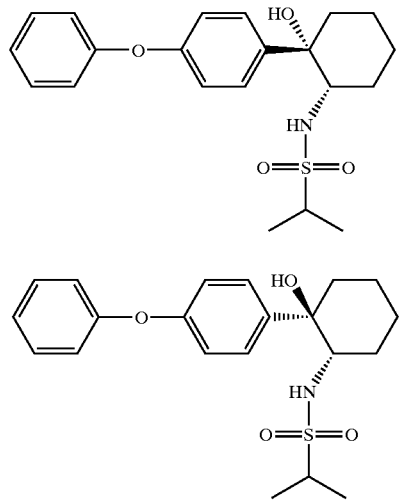

The title compounds were prepared in a manner analogous to the procedure set forth in Example 60 from 4-phenoxyphenylmagnesium bromide (17 mL, 1.1 eq., 0.5 M solution) and 2-{[(methylethyl)sulfonyl]amino}cyclohexan-1-one (1.70 g, 7.8 mmol) to provide a cis/trans mixture of the title compound (3.24 g) as a dark semi-solid. This material was separated and purified via silica gel chromatography employing the Water's Prep. 2000 while eluting with a solvent of hexane/ethyl acetate 3:2 to yield the cis isomer of the title compound (70 mg, top spot by TLC) as a white solid. Ion spray M.S. 388.1 (M*−1). Calculated for $C_{21}H_{27}NO_4S$: Theory: C 64.76, H 6.99, N 3.60. Found: C 63.98, H 7.07, N 3.42.

Continued elution afforded the trans isomer of the title compound (91 mg, bottom spot by TLC) as a semi-solid. Fd M.S. 388.2 (M*−1). Calculated for $C_{21}H_{27}NO_4S \cdot \frac{1}{2}H_2O$: Theory: C 63.23, H 7.08, N 3.52. Found: C 62.81, H 6.93, N 3.29.

EXAMPLE 63

Preparation of trans-[2-fluoro-2-(4-methoxyphenyl)cyclohexyl][(methylethyl)sulfonyl]amine and cis-[2-fluoro-2-(4-methoxyphenyl)cyclohexyl][(methylethyl)sulfonyl]amine

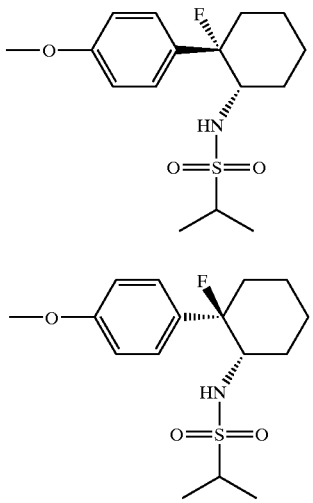

The title compounds were prepared in a manner analogous to the procedure set forth in Example 59 from a cis/trans mixture of [2-hydroxy-2-(4-methoxyphenyl)cyclohexyl][(methylethyl)sulfonyl]amine (200 mg, 0.61 mmol) to provide a cis/trans mixture of the title compounds (220 mg) as an oil. This material was separated and purified via silica gel chromatography employing the Chromatotron® and using a 4000 micron rotor while eluting with a solvent of methylene chloride to yield the trans isomer of the title compound (120 mg, top spot by TLC) as an oil. Ion spray M.S. 309.1 (M*-Fluorine). Calculated for $C_{16}H_{24}NO_3SF$: Theory: C 58.34, H 7.34, N 4.25. Found: C 57.69, H 7.39, N 4.19.

Continued elution afforded a cis/trans mixture (60 mg) as an oil. Fd M.S. 329.4 (M*). Final elution afforded the cis isomer of the title compound (13 mg, bottom spot by TLC) as a semi solid material. Ion spray M.S. 301.1 (M*-Fluorine). Calculated for $C_{16}H_{24}NO_3SF$: Theory: C 58.34, H 7.34, N 4.25. Found: C 58.76, H 7.73, N 3.92.

EXAMPLE 64

Preparation of trans-(2-fluoro-2-[4-(phenylmethoxy)phenyl]cyclohexyl}[(methylethyl)sulfonyl]amine and cis-[2-fluoro-2-[4-(phenylmethoxy)phenyl]cyclohexyl}[(methylethyl)sulfonyl]amine

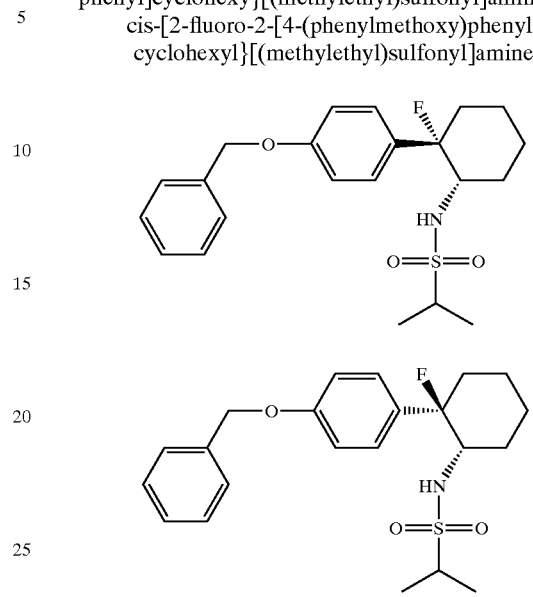

The title compounds were prepared in a manner analogous to the procedure set forth in Example 59 from a cis/trans mixture of trans-{2-hydroxy-2-[4-(phenylmethoxy)phenyl]cyclohexy}[(methylethyl)sulfonyl]amine (2.20 g, 5.45 mmol) to yield a cis/trans mixture of the title compounds (2.45 g) as an oil. This material was separated and purified in 3 lots via silica gel chromatography employing the Chromatotron® and using a 4000 micron rotor while eluting with a solvent of hexane/tetrahydrofuran 4:1 to yield the trans isomer of the title compound (1.31 g, top spot by TLC) as an oil. Ion spray M.S. 404.1 (M*-1).

Continued elution afforded the cis isomer of the title compound (80 mg, bottom spot by TLC) as a viscous oil. Ion spray M.S. 404.1 (M*-1). Calculated for $C_{22}H_{28}NO_3SF\cdot\frac{1}{2}H_2$): Theory: C 63.76, H 7.05, N 3.38. Found: C 63.80, H 7.30, N 3.61.

EXAMPLE 65

Preparation of trans-[2-fluoro-2-(4-phenoxyphenyl)cyclohexyl][(methylethyl)sulfonyl]amine and cis-[2-fluoro-2-(4-phenoxyphenyl)cyclohexyl][(methylethyl)sulfonyl]amine

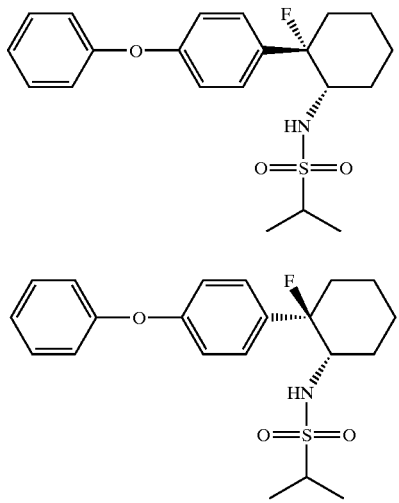

The title compounds are prepared in a manner analogous to the procedure set forth in Example 59 from [2-hydroxy-2-(4-phenoxyphenyl)cyclohexyl][(methylethyl)sulfonyl]amine to provide a cis/trans mixture of the title compounds (212 mg) as an oil. This material was separated and purified via silica gel chromatography employing the Chromatotron® and using a 4000 micron rotor while eluting with a solvent of hexane/ethyl acetate 4:1 to yield the trans isomer of the title compound (35 mg, top spot by TLC) as an oil. Ion spray M.S. 390.1 (M*-1). Calculated for $C_{21}H_{26}NO_3SF$: Theory: C 64.43, H 6.70, N 3.58. Found: C 64.26, H 6.64, N 3.50.

Continued elution afforded a cis/trans mixture (133 mg) as an oil. Fd M.S. 390.1 (M*-1). Final elution afforded the cis isomer of the title compound (20 mg, bottom spot by TLC) as an oil. Ion spray M.S. 390.1 (M*-1).

EXAMPLE 66

Preparation of [2-hydroxy-2-(4-hydroxyphenyl)cyclohexyl][(methylethyl)sulfonyl]amine

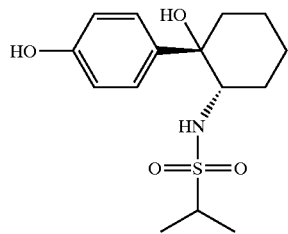

{2-Hydroxy-2-[4-(phenylmethoxy)phenyl]cyclohexyl}[(methylethyl)sulfonyl]amine (5.00 g, 12.8 mmol) was combined with 5% palladium on carbon in ethyl acetate (200 mL) mixed together and placed on the power shaker under a hydrogen atmosphere at 45 psl's overnight. The solution was filtered over a Celite® mat and the resulting filtrate was concentrated under reduced vacuum to yield 4.1 g as a white solid. This material was purified via silica gel chromatography employing the Water's prep. 2000 while eluting with a solvent of methylene chloride/methanol 9:1 to provide the title compound (3.75 g 94%) as a white solid. Ion Spray M.S. 312.1 (M*-1). Calculated for $C_{15}H_{23}NO_4S$: Theory: C 57.48, H 7.40, N 4.47. Found: C 57.11, H 7.40, N 4.65.

EXAMPLE 67

Preparation of cis-[2-fluoro-2-(4-hydroxyphenyl)cyclohexyl][(methylethyl)sulfonyl]amine and trans-[2-fluoro-2-(4-hydroxyphenyl)cyclohexyl][(methylethyl)sulfonyl]amine

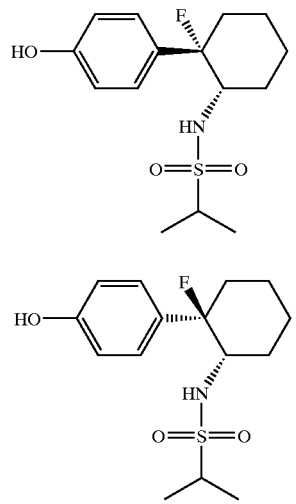

The title compound are prepared in a manner analogous to the procedure set forth in Example 59 from [2-hydroxy-2-(4-hydroxyphenyl)cyclohexyl][(methylethyl)sulfonyl]amine (250 mg, 0.83 mmol) to provide 262 mg of a 2 spot material as a yellow solid. This material was separated and purified via silica gel chromatography employing the Chromatotron® and using a 4000 micron rotor while eluting with a solvent of hexane/ethyl acetate 3:2 to yield the trans isomer of the title compound (110 mg, top spot by TLC) as a white solid. Ion spray M.S. 296.1 (M*-fluorine). Calculated for $C_{15}H_{22}NO_3SF$: Theory: C 57.12, H 7.03, N 4.44. Found: C 57.08, H 7.08, N 4.47.

Continued elution afforded 100 mg of a cis/trans mixture of the title compound as an oil. Fd M.S. 315.1.1 (M*).

EXAMPLE 68

Preparation of }2-hydroxy-2-[4-(2-{[(methylethyl)suflonyl]amino}ethoxy)phenyl]cyclohexyl}[(methylethyl)sulfonyl]amine

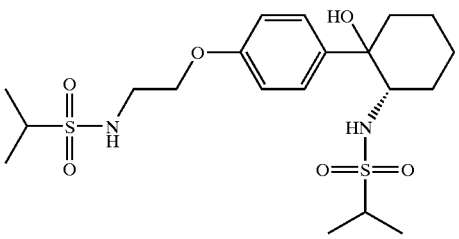

Preparation of 2-[4-(1-hydroxy-2-{[(methylethyl)sulfonyl]amino}cyclohexyl)phenoxy]ethanenitrile

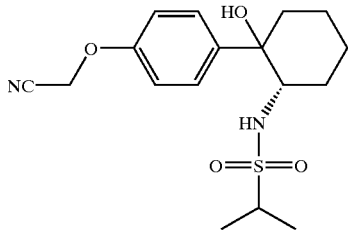

[2-hydroxy-2-(4-hydroxyphenyl)cyclohexyl][(methylethyl)sulfonyl]amine (3.40 g, 10.9 mmol), bromoacetonitrile (1.44 g, 1.1 eq) and potassium carbonate (1.80 g, 1.2 eq) were combined in acetone (20 mL) and stirred overnight at room temperature under a nitrogen atmosphere. The solution was then filtered and the filtrate was concentrated under reduced vacuum to yield 3.71 g as a brown oil. This material was purified via silica gel chromatography employing the Water's Prep. 200 while eluting with a solvent of hexane/ethyl acetate 3:2 to yield the intermediate title compound (2.52 g, 67%) as a tan solid. Ion spray M.S. 351.2 (M*−1). Calculated for $C_{17}H_{24}N_2O_4S$: Theory: C 57.93, H 6.86, N 7.95. Found: C 57.61, H 6.84, N 8.12.

Preparation of {2-[4-(2-aminoethoxy)phenyl]-2-hydroxycyclohexyl}[(methylethyl)sulfonyl]amine

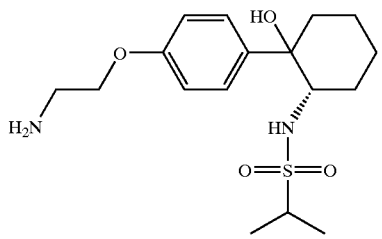

Into a 100 mL, 3 neck flask with stirrer, 2-[4-(1-hydroxy-2-{[(methylethyl)sulfonyl]amino}cyclohexyl)phenoxy]ethanenitrile (400 mg) in THF-toluene 1:1 (30 mL) was added dropwise to Red-Al® (3 mL, 65% solution in toluene) while stirring at room temperature under a nitrogen atmosphere. The reaction mixture was then stirred for two hours at this temperature. The mixture was poured into water and the desired material was extracted with ethyl acetate. The organic layer was washed once with water, dried over potassium carbonate, filtered, and concentrated under reduced vacuum to yield the intermediate title compound (478 mg, 89%) as a white foam. This material was used without further purification. Ion spray M.S. 355.2 (M*−1). Calculated for $C_{17}H_{28}N_2O_4S \cdot H_2O$: Theory: C 54.51, H 8.07. Found: C 54.20, H 8.29.

Preparation of Final Title Compound

The final title compound was prepared in a manner analogous to the procedure set forth in Example 51 from {2-[4-(2-aminoethoxy)phenyl]-2-hydroxycyclohexyl}[(methylethyl)sulfonyl]amine (230 mg, 0.65 mmol), 2-propanesulfonyl chloride (111 mg, 1.2 Equiv.), and DBU (148 mg, 1.5 Equiv.), to yield the crude final product (257 mg) as an oil. This material was purified via silica gel chromatography employing the Chromatotron® using a 2000 micron rotor while eluting with a solvent of methylene chloride/ethyl acetate 7:3 to yield the title compound (91 mg, 31%) as an oil. Ion spray M.S. 461.3 (M*−1). Calculated for $C_{20}H_{34}N_2O_6S_2 \cdot \tfrac{1}{2}H_2O$: Theory: C 50.92, H 7.48, N 5.94. Found: C 51.19, H 7.39, N 5.39.

EXAMPLE 69

Preparation of [2-hydroxy-2-(4-(2-{(methylsulfonyl)amino]ethoxy}phenyl)cyclohexyl][(methylethyl)suflonyl]amine

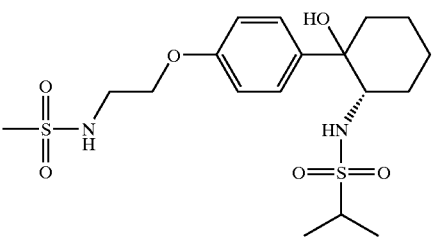

The title compound was prepared in a manner analogous to the procedure set forth in Example 51 from {2-[4-(2-aminoethoxy)phyenyl]-2-hydroxycyclohexyl}[(methylethyl)sulfonyl]amine (230 mg, 0.65 mmol), 2-methanesulfonyl chloride (93 mg, 1.2 Equiv.), and DBU (148 mg, 1.5 Equiv.), to yield the crude final product (302 mg) as an oil. This material was purified via silica gel chromatography employing the Chromatotron® using a 2000 micron rotor while eluting with a solvent of methylene chloride/ethyl acetate 7:3 to yield the title compound (167 mg, 59%) as an oil. Ion spray M.S. (M*−1). Calculated for $C_{18}H_{30}N_2O_6S_2 \cdot \tfrac{1}{2}H_2O$: Theory: C 48.73 H 7.04, N 6.32. Found: C 49.05, H 6.82, N 6.26.

EXAMPLE 70

Preparation of N-[2-[4-(1-hydroxy-2-{[(methylethyl)sulfonyl]amino}cyclohexyl)phenoxy]ethyl}acetamide

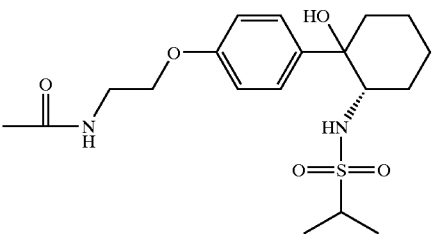

The title compound is prepared in a manner analogous to the procedure set forth in Example 53 from {2-[4-(2-aminoethoxy)phenyl -2-hydroxycyclohexyl}[(methylethyl)sulfonyl]amine and acetyl chloride.

EXAMPLE 71

Preparation of [2-fluoro-2-(4-(2-[(methylsulfonyl)amino]ethoxy}phenyl)cyclohexyl][(methylethyl)sulfonyl]amine

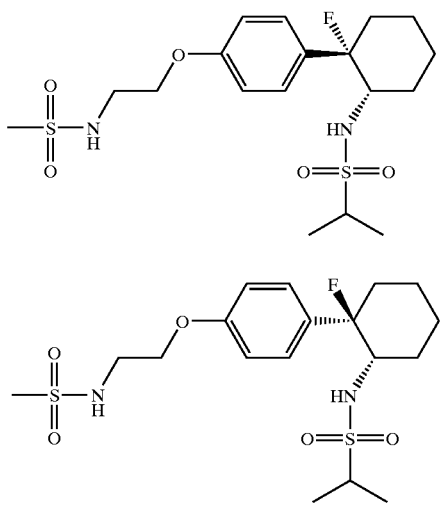

The title compound was prepared in a manner analogous to the procedure set forth in Example 59 from [2-hydroxy-2-(4-{2-[(methylsulfonyl)amino]ethoxy}phenyl)cyclohexyl][(methylethyl)sulfonyl]amine (155 mg, 0.36 mmol) and DAST (0.01 mL) to provide a cis/trans mixture of the title compounds (141 mg) as a foam. This material was separated and purified via silica gel chromatography employing the Chromatotron® and using a 4000 micron rotor while eluting with a solvent of methylene chloride/ethyl acetate 4:1 to yield the trans isomer of the title compound (80 mg, top spot by TLC) as a white solid. Ion spray M.S. 435.3 (M*−1) Calculated for $C_{18}H_{29}N_2O_5S_2F$-½$H_2O$: Theory: C 47.55, H 6.84, N 6.16. Found: C 47.58, H 6.89, N 5.65. Continued elution afforded a cis/trans mixture (61 mg) as a foam. Fd M.S. 435.3 (M*−1). Calculated for $C_{18}H_{29}N_2O_5S_2F$-½$H_2O$: Theory: C 49.52, H 6.70, N 6.42. Found: C 49.17, H 6.64, N 6.22.

EXAMPLE 72

Preparation of {2-fluoro-2-[4-(2-{[(methylethyl)sulfonyl][amino)ethoxy)phenyl]cyclohexyl}[(methylethyl)sulfonyl]amine

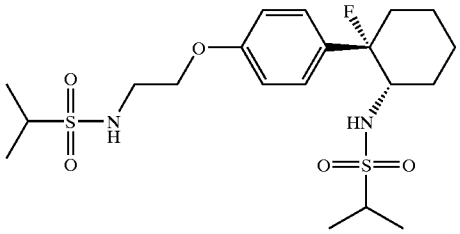

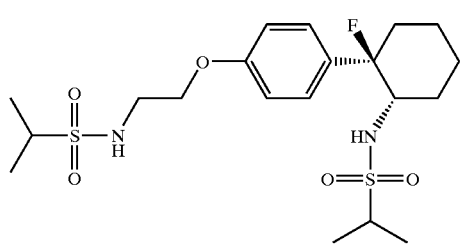

The title compound was prepared in a manner analogous to the procedure set forth in Example 59 from {2-hydroxy-2-[4-(2-{[(methylethyl)sulfonyl]amino}ethoxy)phenyl]cyclohexyl}[(methylethyl)sulfonyl]amine (80 mg, 0.17 mmol) and DAST (0.05 mL) to provide a cis/trans mixture of the title compounds (81 mg) as an oil. This material was separated and purified via silica gel chromatography employing the Chromatotron® and using a 2000 micron rotor while eluting with a solvent of methylene chloride/ethyl acetate 4:1 to yield the trans isomer of the title compound (30 mg, top spot by TLC) as an oil. Ion spray M.S. 463.3 (M*−1). Calculated for $C_{20}H_{33}N_2O_5S_2F$: Theory: C 51.70, H 7.16, N 6.03. Found: C 51.43, H 7.16, N 5.89. Continued elution afforded a cis/trans mixture (11 mg) as a foam. Fd M.S. 463.3 (M*−1).

EXAMPLE 73

Preparation of N-(2-[4-(1-fluoro-2-{[(methylethyl)sulfonyl]amino}cyclohexyl)phenoxy]ethyl}acetamide

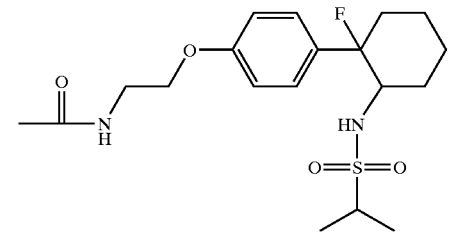

The title compounds is prepared in a manner analogous to the procedure set forth in Example 59 from N-{2-[4-(1-hydroxy-2-{[(methylethyl)sulfonyl]amino}cyclohexyl)phenoxy]ethyl}acetamide

EXAMPLE 74

Preparation of (2-{4-[(3,5-difluorophenyl)methoxy]phenyl]-2-hydroxycyclohexyl)[(methylethyl)sulfonyl]amine

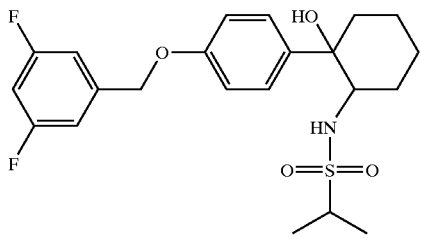

The title compound is prepared in a manner analogous to the procedure set forth in Example 48 from 3,5-difluorobenzyl bromide and [2-hydroxy-2-(4-hydroxyphenyl)cyclohexyl][(methylethyl)sulfonyl]amine to provide 511 mg as a brown oil. This material was purified via silica gel chromatography employing the Chromatotron® using a 4000 micron rotor while eluting with a solvent of methylene chloride/ethyl acetate 4:1 to yield the title compound (360 mg, 85%) as a white solid. Ion spray M.S. 438.3 (M*−1). Calculated for $C_{22}H_{27}NO_4SF_2$: Theory: C 60.12, H 6.19, N 3.19. Found: C 59.32, H 6.14, N 3.26.

EXAMPLE 75

Preparation of 2-{[4-(1-hydroxy-2-{[(methylethyl)sulfonyl]amino}cyclohexyl)phenoxy]methyl}benzenecarbonitrile

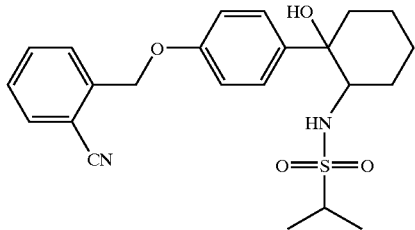

The title compound is prepared in a manner analogous to the procedure set forth in Example 48 from 2-cyanobenzyl bromide and [2-hydroxy-2-(4-hydroxyphenyl)cyclohexyl][(methylethyl)sulfonyl]amine to provide 501 mg as a brown oil. This material was purified via silica gel chromatography employing the Chromatotron® using a 4000 micron rotor while eluting with a solvent of methylene chloride/ethyl acetate 9:1 to yield the title compound (291 mg, 71%) as a white solid. Ion spray M.S. 427.4 (M*−1). Calculated for $C_{23}H_{28}N_2O_4S$-½$H_2O$: Theory: C 63.12, H 6.70, N 6.40. Found: C 63.20, H 6.64, N 6.28.

EXAMPLE 76

Preparation of cis-(2{4-[(3,5-difluorophenyl)methoxy]phenyl}-2-fluorocyclohexyl)[(methylethyl)sulfonyl]amine and trans-(2-[4-[(3,5-difluorophenyl)methoxy]phenyl}-2-fluorocyclohexyl)[(methylethyl)sulfonyl]amine

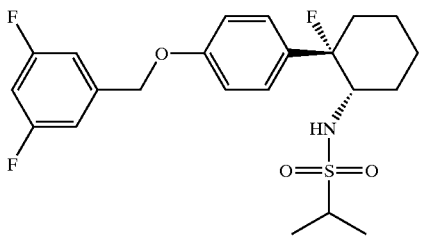

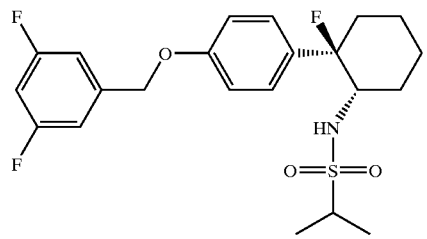

Into a 50 mL 3 neck flask fitted with a stirrer and thermometer, (2-{4-[(3,5-difluorophenyl)methoxy]phenyl}-2-hydroxycyclohexyl)[(methylethyl)sulfonyl]amine (350 mg, 0.80 mmol) In $CH_2Cl_2$ (5 mL) was added dropwise to 0.01 mL DAST in $CH_2CL_2$(15 mL) while stirring at −78° C. under a nitrogen atmosphere. The reaction was allowed to warm to room temperature and diluted with $CH_2Cl_2$ (20 mL). This organic layer was washed with $H_2O$, dried over $Na_2SO_4$, filtered, and concentrated under reduced vacuum to yield 351 mg of an oil (2 spots by TLC). This material was separated and purified via silica gel chromatography employing the Chromatotron® and using a 4000 micron rotor while eluting with a solvent of hexane/ethyl acetate 9:1 to yield the trans isomer of the title compound (27 mg, top spot by TLC) as a white solid. Ion Spray M.S. 440.2 (M*−1). Calculated for $C_{22}H_{26}NO_3SF_3$: Theory: C 59.85, H 5.94, N 3.17. Found: C 59.02, H 5.96, N 3.38.

Continued elution afforded a cis/trans mixture of the title compound (254 mg) as a semi-solid. Fd M.S. 440.2 (M*−1).

EXAMPLE 77

Preparation of cis-2-{[(4-(1-fluoro-2-{
[(methylethyl)sulfonyl]amino}cyclohexyl(phenoxy]
methyl}benzenecarbonitrile and trans -2-{[4-(1-
fluoro-2-{[(methylethyl)sulfonyl]amino}cyclohexyl)
phenoxy]methyl}benzenecarbonitrile

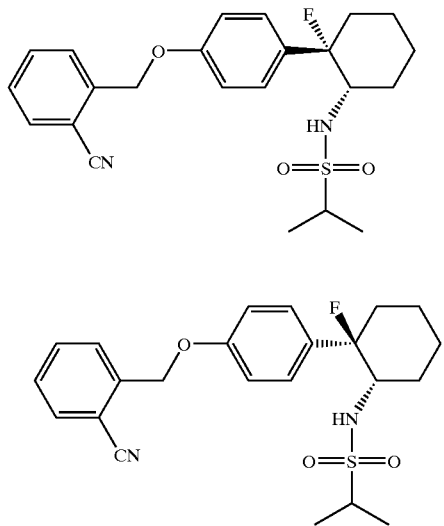

Into a 50 mL 3 neck flask fitted with a stirrer and thermometer, 2-{[4-(1-hydroxy-2-{[(methylethyl)sulfonyl]amino}cyclohexyl)phenoxy]methyl}benzenecarbonitrile (200 mg, 0.47 mmol) in $CH_2Cl_2$ (5 mL) was added dropwise to 0.05 mL DAST in $CH_2CL_2$ (15 mL) while stirring at −78° C. under a nitrogen atmosphere. The reaction was allowed to warm to room temperature and diluted with $CH_2Cl_2$ (20 mL). This organic layer was washed with $H_2O$, dried over $Na_2SO_4$, filtered, and concentrated under reduced vacuum to yield 178 mg of an oil (2 spots by TLC) This material was separated and purified via silica gel chromatography employing the Chromatotron® and using a 4000 micron rotor while eluting with a solvent of methylene chloride/ethyl acetate 9:1 to yield the trans isomer of the title compound (17 mg, top spot by TLC) as a white foam. Ion spray M.S. 429.2 (M*−1). Continued elution afforded a cis/trans mixture of the title compound (151 mg) as a semi-solid.

The ability of compounds of formula I to potentiate glutamate receptor-mediated response may be determined using fluorescent calcium indicator dyes (Molecular Probes, Eugene, Oreg., Fluo-3) and by measuring glutamate-evoked efflux of calcium into GluR4 transfected HEK293 cells, as described in more detail below.

In one test, 96 well plates containing confluent monolayers of HEK 293 cells stably expressing human GluR4B (obtained as described in European Patent Application Publication Number EP-A1-583917) are prepared. The tissue culture medium in the wells is then discarded, and the wells are each washed once with 200 μl of buffer (glucose, 10 mM, sodium chloride, 138 mM, magnesium chloride, 1 mM, potassium chloride, 5 mM, calcium chloride, 5 mM, N-[2-hydroxyethyl]-piperazine-N-[2-ethanesulfonic acid], 10 mM, to pH 7.1 to 7.3). The plates are then incubated for 60 minutes in the dark with 20 μM Fluo3-AM dye (obtained from Molecular Probes Inc., Eugene, Oreg.) in buffer in each well. After the incubation, each well is washed once with 100 μl buffer, 200 μl of buffer is added and the plates are incubated for 30 minutes. Solutions for use in the test are also prepared as follows. 30 μM, 10 μM, 3 μM and 1 μM dilutions of test compound are prepared using buffer from a 10 mM solution of test compound in DMSO. 100 μM cyclothiazide solution is prepared by adding 3 μl of 100 mM cyclothiazide to 3 mL of buffer. Control buffer solution is prepared by adding 1.5 μl DMSO to 498.5 μl of buffer. Each test is then performed as follows. 200 μl of control buffer in each well is discarded and replaced with 45 μl of control buffer solution. A baseline fluorescent measurement is taken using a FLUOROSKAN II fluorimeter (Obtained from Labsystems, Needham Heights, Mass., USA, a Division of Life Sciences International Plc). The buffer is then removed and replaced with 45 μl of buffer and 45 μl of test compound in buffer in appropriate wells. A second fluorescent reading is taken after 5 minutes incubation. 15 μl of 400 μM glutamate solution is then added to each well (final glutamate concentration 100 μM), and a third reading is taken. The activities of test compounds and cyclothiazide solutions are determined by subtracting the second from the third reading (fluorescence due to addition of glutamate in the presence or absence of test compound or cyclothiazide) and are expressed relative to enhance fluorescence produced by 100 μM cyclothiazide.

In another test, HEK293 cells stably expressing human GluR4 (obtained as described in European Patent Application Publication No. EP-A1-0583917) are used in the electrophysiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm kg-1. The intracellular recording solution contains (in mM): 140 CsCl, 1 $MgCl_2$, 10 HEPES, (N-[2-hydroxyethyl]piperazine-N1-[2-ethanesulfonic acid]) 10 EGTA (ethylene-bis(oxyethylene-nitrilo)tetraacetic acid), pH=7.2 with CsOH, 295 mOsm kg-1. With these solutions, recording pipettes have a resistance of 2–3 MΩ. Using the whole-cell voltage clamp technique (Hamill et al.(1981)Pflüugers Arch., 391:85–100), cells are voltage-clamped at −60 mV and control current responses to 1 mM glutamate are evoked. Responses to 1 mM glutamate are then determined in the presence of test compound. Compounds are deemed active in this test if, at a test concentration of 10 μM or less, they produce a greater than 10% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 μM cyclothiazide is determined by its inclusion in both the bathing solution and the glutamate-containing solution. In this manner, the efficacy of the test compound relative to that of cyclothiazide can be determined.

According to another aspect, the present invention provides a pharmaceutical composition, which comprises a compound of formula I or a pharmaceutically acceptable salt thereof and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1
Hard gelatin capsules are prepared using the following ingredients:

| | Quantify (mg/capsule) |
|---|---|
| Active Ingredient | 250 |
| Starch, dried | 200 |
| Magnesium Stearate | 10 |
| Total | 460 |

The above ingredients are mixed and filled into hard gelatin capsules in 460 mg quantities.

Formulation 2
Tablets each containing 60 mg of active ingredient are made as follows:

| | Quantity (mg/tablet) |
|---|---|
| Active Ingredient | 60 |
| Starch | 45 |
| Microcrystalline Cellulose | 35 |
| Polyvinylpyrrolidone | 4 |
| Sodium Carboxymethyl Starch | 4.5 |
| Magnesium Stearate | 0.5 |
| Talc | 1 |
| Total | 150 |

As used herein the term "active ingredient" refers to a compound of formula I. The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

As used herein the term "patient" refers to a mammal, such as a mouse, guinea pig, rat, dog or human. It is understood that the preferred patient is a human.

As used herein, the terms "treating" or "treat" each mean to alleviate symptoms, eliminate the causation either on a temporary or permanent basis, or to prevent or slow the appearance of symptoms of the named disorder. As such, the methods of this invention encompass both therapeutic and prophylactic administration.

As used herein, the term "effective amount" refers to the amount of a compound of formula I which is effective, upon single or multiple dose administration to a patient, in treating the patient suffering from the named disorder.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds can be administered by a variety of routes including oral, rectal, transdermal, subcutaneous, intravenous, intramuscular, bucal or intranasal routes. Alternatively, the compound may be administered by continuous. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

We claim:

1. A compound of the formula:

$$\text{R}^1\text{-G cyclopentane-(CH}_2)_p\text{-NH-S(=O)}_2\text{-R}^2$$

wherein
- G represents F or OH;
- $R^1$ represents an unsubstituted or substituted aromatic group, an unsubstituted or substituted heteroaromatic group, or an unsubstituted or substituted (5–8C) cycloalkyl group;
- $R^2$ represents (1–6C)alkyl, (2–6C)alkenyl, or a group of formula $R^3R^4N$ in which $R^3$ and $R^4$ each independently represent (1–4C)alkyl; and
- p represents the integer 1 or 2;

or a pharmaceutically acceptable salt thereof.

2. A compound according to claim 1 wherein $R^2$ represents (1–6C)alkyl.

3. A compound according to claim 2 wherein $R^2$ represents 2-propyl.

4. A compound according to claim 3 wherein p represents 1.

5. A compound according to claim 3 wherein p represents 2.

6. A compound according to claim 4 wherein G represents F.

7. A compound according to claim 4 wherein G represents OH.

8. A compound according to claim 6 wherein $R^1$ represents an unsubstituted or substituted aromatic group.

9. A compound according to claim 8 wherein the substituted aromatic group is a substituted phenyl.

10. A compound according to claim 9 wherein the phenyl is substituted with halogen; nitro; cyano; (1–10C)alkyl; (2–10C)alkenyl; (2–10C)alkynyl; (3–8C)cycloalkyl; hydroxy(3–8C)cycloalkyl; oxo(3–8C)cycloalkyl; halo (1–10C)alkyl; —O—$(CH_2)_t$CN, —O—$(CH_2)_t$NH$_2$, —O—$(CH_2)_t$NHCOR$^{10a}$, —O—$(CH_2)_t$NHSO$_2$R$^{10a}$ in which t is an integer of from 1 to 4; $(CH_2)_y$X$^1$R$^9$ in which y is 0 or an integer of from 1 to 4, X$^1$ represents O, S, NR$^{10}$, CO, COO, OCO, CONR$^{11}$, NR$^{12}$CO, NR$^{12}$COCOO, OCONR$^{13}$, R$^9$ represents hydrogen, (1–10C)alkyl, (3–10C)alkenyl, (3–10C)alkynyl, pyrrolidinyl, tetrahydrofuryl, morpholino or (3–8C)cycloalkyl and R$^{10}$, R$^{10a}$, R$^{11}$, R$^{12}$ and R$^{13}$ each independently represents hydrogen or (1–10C)alkyl, or R$^9$ and R$^{10}$, R$^{11}$, R$^{12}$ or R$^{13}$ together with the nitrogen atom to which they are attached form an azetidinyl, pyrrolidinyl, piperidinyl or morpholino group N-(1–4C)alkylpiperazinyl; N-phenyl(1–4C)alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyl dihydrothiazolyl; (1–4C) alkoxycarbonyl dimethyl-dihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula R$^{14}$-(L$^a$)$_n$-X$^2$-(L$^b$)$_m$ in which X$^2$ represents a bond, O, NH, S, SO, SO$_2$, CO, CH(OH), CONH, NHCO, NHCONH, NHCOO, COCONH, OCH$_2$CONH, or CH=CH, L$^a$ and L$^b$ each represent (1–4C)alkylene, one of n and m is 0 and the other is 0, and R$^{14}$ represents a phenyl or heteroaromatic group which is unsubstituted or substituted by one or two of halogen; nitro; cyano; (1–10C) alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; and $(CH_2)_z$X$^3$R$^{15}$ in which z is 0 or an integer of from 1 to 4, X$^3$ represents O, S, NR$^{16}$, CO, CH(OH), COO, OCO, CONR$^{17}$, NR$^{18}$CO, NHSO$_2$, SO$_2$NH, NHSO$_2$NR$^{17}$, OCONR$^{19}$ or NR$^{19}$COO, R$^{15}$ represents hydrogen, (1–10C)alkyl, phenyl(1–4C)alkyl, halo (1–10C)alkyl, (1–4C)alkoxycarbonyl(1–4C)alkyl, (1–4C) alkylsulfonylamino(1–4C)alkyl, N-(1–4C)alkoxycarbonyl) (1–4C) alkylsulfonylamino(1–4C)alkyl, (3–10C)alkenyl, (3–10C)alkynyl, (3–8C)cycloalkyl, camphoryl, or an aromatic or heteroaromatic group which is unsubstituted or substituted by one or two of halogen, (1–4C)alkyl, halo (1–4C)alkyl, di(1–4C)alkylamino and (1–4C)alkoxy, and R$^{16}$, R$^{17}$, R$^{18}$ and R$^{19}$ each independently represents hydrogen or (1–10C)alkyl, or R$^{15}$ and R$^{16}$, R$^{17}$, R$^{18}$ or R$^{19}$ together with the nitrogen atom to which they are attached form an azetidinyl, pyrrolidinyl, piperidinyl or morpholino group.

11. A compound according to claim 10 wherein the substituted phenyl is substituted with a group of formula R$^{14}$-(L$^a$)$_n$-X$^2$-(L$^b$)$_m$ in which X$^2$ represents a bond, O, NH, S, SO, SO$_2$, CO, CH(OH), CONH, NHCO, NHCONH, NHCOO, COCONH, OCH$_2$CONH, or CH=CH, L$^a$ and L$^b$ each represent (1–4C)alkylene, one of n and m is 0 or 1 and the other is 0, and R$^{14}$ represents a phenyl or heteroaromatic group which is unsubstituted or substituted by one or two of halogen; nitro; cyano; (1–10C)alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; and $(CH_2)_z$X$^3$R$^{15}$ in which z is 0 or an integer of from 1 to 4, X$^3$ represents O, S, NR$^{16}$, CO, CH(OH), COO, OCO, CONR$^{17}$, NR$^{18}$CO, NHSO$_2$, SO$_2$NH, NHSO$_2$NR$^{17}$, OCONR$^{19}$ or NR$^{19}$COO, R$^{15}$ represents hydrogen, (1–10C) alkyl, phenyl(1–4C)alkyl, halo(1–10C)alkyl, (1–4C) alkoxycarbonyl(1–4C)alkyl, (1–4C)alkylsulfonylamino) 1–4C)alkyl, N-(1–4C)alkoxycarbonyl)(1–4C) alkylsulfonylamino(1–4C)alkyl, (3–10C)alkenyl, (3–10C) alkynyl, (3–8C)cycloalkyl, camphoryl, or an aromatic or heteroaromatic group which is unsubstituted or substituted by one or two of halogen, (1–4C)alkyl, halo(1–4C)alkyl, di(1–4C)alkylamino and (1–4C)alkoxy, and R$^{16}$, R$^{17}$, R$^{18}$ and R$^{19}$ each independently represents hydrogen or (1–10C) alkyl, or R$^{15}$ and R$^{16}$, R$^{17}$, R$^{18}$ or R$^{19}$ together with the nitrogen atom to which they are attached form an azetidinyl, pyrrolidinyl, piperidinyl or morpholino group.

12. A compound according to claim 10 wherein (L$^a$)$_n$-X$^2$-(L$^b$)$_m$ represents a bond, CONH, or CH$_2$O.

13. A compound according to claim 12 wherein R$^{14}$ represents a phenyl which is unsubstituted or substituted by one or two of halogen; nitro; cyano; (1–10C)alkyl; (2–10C) alkenyl; (2–10C)alkynyl; (3–8C)cycloalkyl; 4-(1,1-dioxotetrahydro-1,2-thiazinyl); halo(1–10C)alkyl; cyano (2–10C)alkenyl; phenyl; and $(CH_2)_z$X$^3$R$^{15}$ in which z is 0 or an integer of from 1 to 4, X$^3$ represents O, S, NR$^{16}$, CO, CH(OH), COO, OCO, CONR$^{17}$, NR$^{18}$CO, NHSO$_2$, SO$_2$NH, NHSO$_2$NR$^{17}$, OCONR$^{19}$ or NR$^{19}$COO, R$^{15}$ represents hydrogen, (1–10C)alkyl, phenyl(1–4C)alkyl, halo(1–10C) alkyl, (1–4C)alkoxycarbonyl(1–4C)alkyl, (1–4C) alkylsulfonylamino(1–4C)alkyl, N-(1–4C)alkoxycarbonyl) (1–4C) alkylsulfonylamino(1–4C)alkyl, (3–10C)alkenyl, (3–10C)alkynyl, (3–8C)cycloalkyl, camphoryl, or an aromatic or heteroaromatic group which is unsubstituted or substituted by one or two of halogen, (1–4C)alkyl, halo (1–4C)alkyl, di(1–4C)alkylamino and (1–4C)alkoxy, and R$^{16}$, R$^{17}$, R$^{18}$ and R$^{19}$ each independently represent hydrogen or (1–10C)alkyl, or R$^{15}$ and R$^{16}$, R$^{17}$, R$^{18}$ or R$^{19}$ together with the nitrogen atom to which they are attached form an azetidinyl, pyrrolidinyl, piperidinyl or morpholino group.

14. A compound according to claim 13 wherein $R^{14}$ represents a phenyl which is substituted by one or two of halogen; nitro; cyano; (1–10C)alkyl; halo(1–10C)alkyl; and $(CH_2)_zX^3R^{15}$ in which z is 0, 1 or 2, $X^3$ represents O, $NR^{16}$, CO, COO, $CONR^{17}$, $NR^{18}CO$, $NHSO_2$, $SO_2NH$, $NHSO_2NR^{17}$, $OCONR^{19}$ or $NR^{19}COO$, $R^{15}$ represents hydrogen, (1–10C)alkyl, phenyl(1–4C)alkyl, halo(1–10C) alkyl, or (3–10C)alkenyl, and $R^{16}$, $R^{17}$, $R^{18}$ and $R^{19}$ each independently represent hydrogen or (1–10C)alkyl.

15. A compound according to claim 14 wherein $R^{14}$ represents a phenyl which is substituted by one or two of fluoro; chloro, cyano; (1–4C)alkyl; trifluoromethyl; and $(CH_2)_zX^3R^{15}$ in which z is 0, or 2, $X^3$ represents $NR^{16}$, CO, COO, $CONR^{17}$, $NR^{18}CO$, $NHSO_2$, $R^{15}$ represents hydrogen, (1–4C)alkyl, phenyl(1–4C)alkyl, or halo(1–4C) alkyl, and $R^{16}$, $R^{17}$, $R^{18}$ and $R^{19}$ each independently represent hydrogen or (1–4C)alkyl.

16. A compound according to claim 10 wherein the phenyl is substituted with $-O-(CH_2)_tNHCOR^{10a}$, or $-O-(CH_2)_tNHSO_2R^{10a}$ in which t is an integer of from 1 to 4, and $R^{10a}$ represents (1–10C)alkyl.

17. A compound according to claim 16 wherein t is 2.

18. A compound according to claim 17 wherein $R^{10a}$ is (1–4C)alkyl.

19. A compound according to claim 18 wherein $-O-(CH_2)_tNHCOR^{10a}$ and $-O-(CH_2)_tNHSO_2R^{10a}$ are at the 4-position on the phenyl ring.

20. A compound according to claim 19 wherein $R^{10a}$ is methyl or 2-propyl.

21. A compound which is selected from the group consisting of: trans-[2-fluoro-2-(4-phenylphenyl)cyclohexy] [(methylethyl)sulfonyl]amine; cis-[2-fluoro-2-(4-phenylphenyl)cyclohexyl][(methylethyl)sulfonyl]amine; trans-[2-fluoro-2-(4-phenylphenyl)cyclopentyl][) methylethyl)sulfonyl]amine; trans-[(dimethylamino) sulfonyl][2-fluoro-2-(4-phenylphenyl)cyclopentyl]amine; trans-(2-fluoro-2-phenylcyclohexyl)[(methylethyl)sulfonyl] amine; [2-fluoro-2-(4-nitrophenyl)cyclohexyl] [(methylethyl)sulfonyl]amine; [2-fluoro-2-(4-aminophenyl) cyclohexyl][(methylethyl)sulfonyl]amine; (3,5-difluorophenyl)-N-[4-(1-fluoro-2-{[(methylethyl)sulfonyl] amino}cyclohexyl)phenyl]carboxamide; [2-fluoro-2-(4-bromophenyl)cyclohexyl][(methylethyl)sulfonyl]amine; {2-fluoro-2-[4-(4-{2-](methylsulfonyl)amino]ethyl}phenyl) phenyl]cyclohexyl}[(methylethyl)sulfonyl]-amine; ]2-fluoro-2-(4-phenylphenyl)cyclopentyl][(methylethyl) sulfonyl]amine; [2-(4-fluorophenyl)-2-hydroxycyclopentyl] [(methylethyl)sulfonyl]amine; 2fluoro-2-(4-fluorophenyl) cyclopentyl][(methylethyl)sulfonyl]amine; trans-{2-hydroxy-2-[4-(phenylmethoxy)phenyl]cyclopentyl} [(methylethyl)sulfonyl]amine; cis-{2-hydroxy-2-[4-(phenylmethoxy)phenyl]cyclopentyl}[(methylethyl) sulfonyl]amine; [2-hydroxy-2-(4-hydroxyphenyl) cyclopentyl][(methylethyl)sulfonyl]amine; trans-(2-{4-[(3, 5-difluorophenyl)methoxy]phenyl}-2-hydroxycyclopentyl) [(methylethyl)sulfonyl]amine; cis-(2-{4-[(3,5-difluorophenyl)methoxy]phenyl}-2-hydroxycyclopentyl) [(methylethyl)sulfonyl]amine; [2-hydroxy-2-(4-phenoxyphenyl)cyclopentyl][(methylethyl)sulfonyl]amine; trans-[2-fluoro-2-(4-phenoxyphenyl)cyclopentyl] [(methylethyl)sulfonyl]amine; cis-[2-fluoro-2-(4-phenoxyphenyl)cyclopentyl])methylethyl)sulfonyl]amine; [2-hydroxy-2-(4-{2-[(methylsulfonyl)amino] ethoxy}phenyl)cyclopentyl][(methylethyl)sulfonyl]amine; {2-hydroxy-2-[4-(2-{[(methylethyl)sulfonyl] amino}ethoxy)phenyl]cyclopentyl}[(methylethyl)sulfonyl] amine; N-{2-[4-(1-hydroxy-2-{[(methylethyl)sulfonyl] amino}cyclopentyl)phenoxy]ethyl}acetamide; [2-fluoro-2-(4-{2-[(methylsulfonyl)amino[ethoxy}phenyl)cyclopentyl] [(methylethyl)sulfonyl]amine; {2-fluoro-2-[4-(2-{[(methylethyl)sulfonyl]amino}ethoxy)phenyl]cyclopentyl} [(methylethyl)sulfonyl]amine; N-{2-[4-(1-fluoro-2-{[(methylethyl)sulfonyl]amino}cyclopentyl)phenoxy] ethyl}acetamide; 2-[4-(1-fluoro-2-{[(methylethyl)sulfonyl] amino}cyclopentyl)phenoxy]ethaneitrile; [2-(4-fluorophenyl)-2-hydroxycyclohexyl][(methylethyl) sulfonyl]amine; trans-[2-fluoro-2-(4-fluorophenyl) cyclohexyl][(methylethyl)sulfonyl]amine; cis-[2-fluoro-2-(4-fluorophenyl)cyclohexyl][(methylethyl)sulfonyl]amine; trans-[2-hydroxy-2-(4-methoxyphenyl)cyclohexyl] [(methylethyl)sulfonyl]amine; cis-[2-hydroxy-2-(4-methoxyphenyl)cyclohexyl][(methylethyl)sulfonyl]amine; trans-{2-hydroxy-2-[4-(phenylmethoxy)phenyl] cyclohexyl}[(methylethyl)sulfonyl]amine; cis-{2-hydroxy-2-[4-(phenylmethoxy)phenyl]cyclohexyl}[(methylethyl) sulfonyl]amine; trans-[2-hydroxy-2-(4-phenoxyphenyl) cyclohexyl][(methylethyl)sulfonyl]amine; cis-[2-hydroxy-2-(4-phenoxyphenyl)cyclohexyl][(methylethyl)sulfonyl] amine; trans-[2-fluoro-2-(4-methoxyphenyl)cyclohexyl][) methylethyl)sulfonyl]amine; cis-[2-fluoro-2-(4-methoxyphenyl)cyclohexyl][(methylethyl)sulfonyl]amine; trans-{2-fluoro-2-[4-(phenylmethoxy)phenyl]cyclohexyl} [(methylethyl)sulfonyl]amine; cis-{2-fluoro-2-[4-(phenylmethoxy)phenyl]cyclohexyl}[(methylethyl) sulfonyl]amine; trans-[2-fluoro-2-(4-phenoxyphenyl) cyclohexy][(methylethyl)sulfonyl]amine; cis-[2-fluoro-2-(4-phenoxyphenyl)cyclohexyl])methylethyl)sulfonyl] amine; [2-hydroxy-2-(4-hydroxyphenyl)cyclohexyl] [(methylethyl)sulfonyl]amine; cis-[2-fluoro-2-(4-hydroxyphenyl)cyclohexyl])methylethyl)sulfonyl]amine; trans-[2-fluoro-2-(4-hydroxyphenyl)cyclohexyl][) methylethyl)sulfonyl]amine; {2-hydroxy-2-[4-(2-{[(methylethyl)sulfonyl]amino}ethoxy)phenyl]cyclohexyl} [(methylethyl)sulfonyl]amine; [2-hydroxy-2-(4-{2-[(methylsulfonyl)amino]ethoxy}phenyl)cyclohexyl][) methylethyl)sulfonyl]amine; N-{2-[4-(1-hydroxy-2-{[(methylethyl)sulfonyl]amino}cyclohexyl)phenoxy] ethyl}acetamide; [2-fluoro-2-(4-{2-[(methylsulfonyl) amino]ethoxy}phenyl)cyclohexyl][(methylethyl)sulfonyl] amine; {2-fluoro-2-[4-(2-{[(methylethyl)sulfonyl] amino}ethoxy)phenyl]cyclohexyl][(methylethyl)sufonyl] amine; N-{2-[4-(1-fluoro-2{[(methylethyl)sulfonyl] amino}cyclohexyl)phenoxy]ethyl}acetamide; (2-{4-[(3,5-difluorophenyl)methoxy]phenyl}-2-hydroxycyclohexy) [(methylethyl)sulfonyl]amine; 2-{[4-(1-hydroxy-2-{[(methylethyl)sulfonyl[amino}cyclohexyl)phenoxy] methyl}benzenecarbonitrile; cis-(2-{4-[(3,5-difluorophenyl)methoxy]phenyl}-2-fluorocyclohexyl) [(methylethyl)sulfonyl]amine; trans-(2-{4-[(3,5-difluorophenyl)methoxy]phenyl}-2-fluorocyclohexyl) [(methylethyl)sulfonyl]amine; cis-2-{[4-(1-fluoro-2-{[(methylethyl)sulfonyl]amino}cyclohexyl)phenoxy] methyl}benzenecarbonitrile; and trans-2{[4-(1-fluoro-2-{[(methylethyl)sulfonyl]amino}cyclohexyl)phenoxy] methyl}benzenecarbonitrile; and the pharmaceutically acceptable salts thereof.

22. A pharmaceutical composition, which comprises a compound as claimed in any one of claims 1 to 21 and a pharmaceutically acceptable diluent or carrier.

23. A method of potentiating glutamate receptor function in a patient, which comprises administering to said patient an effective amount of a compound according to claim 1.

24. A method of treating a cognitive disorder; Alzheimer's disease, a neuro-degenerative disorder; age-related dementia; age-induced memory impairment; movement disorder; reversal of a drug-induced state; depression; attention deficit disorder; attention deficit hyperactivity disorder; psychosis; cognitive deficits associated with psychosis; drug-induced psychosis, or stroke in a patient, which comprises administering to a patient an effective amount of a compound according to claim 1.

25. A compound according to claim 5 wherein G represents F.

26. A compound according to claim 5 wherein G represents OH.

27. A compound according to claim 5 wherein $R^1$ represents an unsubstituted or substituted aromatic group.

28. A compound according to claim 27 wherein the substituted aromatic group is a substituted phenyl.

* * * * *